(12) United States Patent
Firooznia et al.

(10) Patent No.: US 8,188,090 B2
(45) Date of Patent: May 29, 2012

(54) NAPHTHYLACETIC ACIDS

(75) Inventors: Fariborz Firooznia, Florham Park, NJ (US); Tai-An Lin, Pequannock, NJ (US); Sung-Sau So, Verona, NJ (US); Baoxia Wang, Shanghai (CN); HongYing Yun, Shanghai (CN)

(73) Assignee: Hoffman-La Roche Inc., Nutley, NJ (US)

( * ) Notice: Subject to any disclaimer, the term of this patent is extended or adjusted under 35 U.S.C. 154(b) by 346 days.

(21) Appl. No.: 12/614,497

(22) Filed: Nov. 9, 2009

(65) Prior Publication Data

US 2010/0125061 A1 May 20, 2010

Related U.S. Application Data

(60) Provisional application No. 61/115,145, filed on Nov. 17, 2008, provisional application No. 61/222,262, filed on Jul. 1, 2009.

(51) Int. Cl.
A61K 31/445 (2006.01)
A61K 31/4965 (2006.01)
A01N 43/40 (2006.01)
C07D 241/04 (2006.01)
C07D 295/00 (2006.01)
C07D 205/00 (2006.01)

(52) U.S. Cl. .................. 514/255.01; 514/330; 544/391; 546/189; 548/953

(58) Field of Classification Search ............. 514/255.01, 514/330; 544/391; 546/189; 548/953
See application file for complete search history.

(56) References Cited

U.S. PATENT DOCUMENTS

| | | | |
|---|---|---|---|
| 3,899,529 | A | 8/1975 | Witzel |
| 4,371,537 | A | 2/1983 | Markley et al. |
| 4,443,462 | A | 4/1984 | Carr et al. |
| 4,868,331 | A | 9/1989 | Niewöhner et al. |
| 4,921,998 | A | 5/1990 | Niewöhner et al. |
| 5,424,481 | A | 6/1995 | Hagen et al. |
| 7,226,951 | B2 | 6/2007 | Vasudevan et al. |
| 2005/0014749 | A1 | 1/2005 | Chen et al. |
| 2006/0154965 | A1 | 7/2006 | Harris et al. |
| 2007/0161698 | A1 | 7/2007 | Chien et al. |
| 2010/0016368 | A1 | 1/2010 | Chen et al. |
| 2010/0016369 | A1 | 1/2010 | Chen et al. |
| 2010/0041713 | A1 | 2/2010 | Firooznia et al. |
| 2010/0041714 | A1 | 2/2010 | Blanc et al. |
| 2010/0041760 | A1 | 2/2010 | Blanc et al. |
| 2010/0125058 | A1 | 5/2010 | Firooznia et al. |
| 2010/0137250 | A1 | 6/2010 | Firooznia et al. |

FOREIGN PATENT DOCUMENTS

| | | |
|---|---|---|
| DE | 4411856 | 1/1994 |
| EP | 0242518 | 10/1987 |
| EP | 0253257 | 1/1988 |
| EP | 0 405 602 A1 * | 6/1990 |
| EP | 0405602 | 1/1991 |
| EP | 0657422 | 6/1995 |
| EP | 1505061 | 2/2005 |
| EP | 1939175 | 7/2008 |
| WO | 92/01675 | 2/1992 |
| WO | 00/16798 | 3/2000 |
| WO | 2005/040114 | 5/2005 |
| WO | 2005/054232 | 6/2005 |
| WO | 2006/034418 | 3/2006 |
| WO | 2006/036664 | 4/2006 |
| WO | 2006/091674 | 8/2006 |
| WO | 2007/028132 | 3/2007 |
| WO | 2007/146136 | 12/2007 |

OTHER PUBLICATIONS

Feixas J et al., "Naphthalene Derivatives; a New Series of Selective Cycloxygenase-2 Inhibitors" Bioorganic & Medicinal Chemistry Letters, 11:20 (2001) 2687-2690 XP0029995309.

(Continued)

*Primary Examiner* — Andrew D Kosar
*Assistant Examiner* — Erich A Leeser
(74) *Attorney, Agent, or Firm* — George W. Johnston; Dennis P. Tramaloni; Brian C. Remy

(57) ABSTRACT

The invention is concerned with the compounds of formula I:

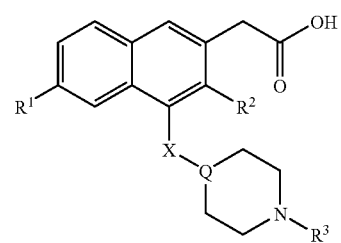

and pharmaceutically acceptable salts and esters thereof, wherein X, Q and $R^1$-$R^3$ are defined in the detailed description and claims. The invention is also concerned with the compounds of formula Z:

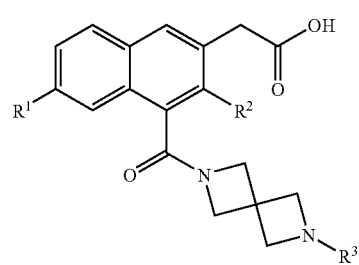

and pharmaceutically acceptable salts and esters thereof, wherein $R^1$-$R^3$ are defined in the detailed description and claims. In addition, the present invention relates to methods of manufacturing and using the compounds of formula I and Z as well as pharmaceutical compositions containing such compounds. The compounds of formula I and Z are antagonists or partial agonists at the CRTH2 receptor and may be useful in treating diseases and disorders associated with that receptor such as asthma.

34 Claims, No Drawings

OTHER PUBLICATIONS

Nagata et al., FEBS Lett 459: 195-199, 1999.
Hirai et al., J Exp Med 193: 255-261, 2001.
Gervais et al., J Allergy Clin Immunol 108: 982-988 (2001).
Xue et al., J Immunol 175: 6531-6536.
Yoshimura-Uchiyama et al., Clin Exp Allergy 34:1283-1290.
Huang et al., Hum Mol Genet 13, 2691-2697, 2004.
Cosmi et al., Eur J. Immunol 30, 2972-2979, 2000.
Lee et al., Tetrahedron Lett., 32 (1991) 5255.
Boger, D. L. et al., J. Org. Chem. 61 (1996) 4894-4912.
Kim, M. et al., J. Org. Chem. 69 (2004) 6945-6948.
Chan W. K., et al., J. Med. Chem. 39 (1996) 3756-3768.
Kozhinov, D. V., et al., J. Org. Chem. 69 (2004) 1378-1379.
Liu, J., et al., Org. Lett. 4 (2002) 3521-3524.
Bloomer, J. L. et al., J. Org. Chem. 58 (1993) 7906-7912.
Fuganti, C. et al., J. Chem. Res (S) 1998, 638-639.
Uno, H., et al., J. Chem. Soc., Perkin Trans. 1, 2001, 229.
Wallace, D. J. et al., Tetrahedron Lett. 43 (2002) 6987-6990.
Zupan M. et al., Bull. Chem. Soc. Jpn., 68 (1995) 1655-1660.
Wu G., et al., Synthesis 11 (2003) 1657-1660.
Thibault, M. E. et al., J. Org. Chem. 68 (2003), 8373-8378.
Schön, U. et al., Tetrahedron Lett. 46 (2005) 7111-7115.
Moseley, J. D. et al., Tetrahedron 62 (2006) 4685-4689.
Baldwin, K. P. et al., Synlett 11 (1993) 853.
Hayashi, N., et al., Org. Lett. 6 (2004) 4981-4983.
Hayashi, N. et al., Org. Lett. 7 (2005) 3093-3096.
Staas, D. D. et al., Bioorg. Med. Chem. 14 (2006) 6900.
Testaferri, L. et al., Tetrahedron 41 (1985) 1373-1384.
Li J. et al., Bioorg. Med. Chem. 13 (2005) 1805-1809.
Bargar, T. M. et al., J. Heterocyclic Chem. 22 (1985) 1583-1592.
Blizzard T. A. et al., Bioorg. Med. Chem. Lett. 14 (2004) 3861-3864.
Arnold et al., Org. Lett, 6 (2004) 3005-3007.
Ulven et al., "Targeting the prostaglandin D2 receptors DP and CRTH2 for treatment of inflammation" Current Topics in Medicinal Chemistry 6:13 (2006) 1427-1444 XP008104082.
Database Registry (online) RN 1026178-75-5 (2008) XP00254729.
Pettipher et al., "Antagonism of the prostaglandin D2 receptors DP1 and CRTH2 as an approach to treat allergic diseases." Nature Reviews Drug Discovery, vol. 6 (Apr. 2007) pp. 313-325, Nature Publishing Group.
Kostenis et al., "Emerging roles of DP and CRTH2 in allergic inflammation" Science Direct, TRENDS in Molecule Medicine vol. 12 No. 4, Apr. 2006, pp. 148-158, Elsevier.

* cited by examiner

NAPHTHYLACETIC ACIDS

PRIORITY TO RELATED APPLICATIONS

This application claims the benefit of U.S. Provisional Application No. 61/115,145, filed Nov. 17, 2008 and U.S. Provisional Application No. 61/222,262, filed Jul. 1, 2009. The entire contents of the above-identified applications are hereby incorporated by reference.

BACKGROUND OF THE INVENTION

The present invention relates to novel substituted naphthalene-2-yl acetic acids, their manufacture, pharmaceutical compositions containing them and their use as CRTH2 antagonists or partial agonists.

Prostaglandin $D_2$ (PGD2) is the major prostanoid produced by activated mast cells and has been implicated in the pathogenesis of allergic diseases such as allergic asthma and atopic dermatitis. Chemoattractant Receptor-homologous molecule expressed on T-helper type cells (CRTH2) is one of the prostaglandin $D_2$ receptors and is expressed on the effector cells involved in allergic inflammation such as T helper type 2 (Th2) cells, eosinophils, and basophils (Nagata et al., *FEBS Lett* 459: 195-199, 1999). It has been shown to mediate PGD2-stimulated chemotaxis of Th2 cells, eosinophils, and basophils (Hirai et al., *J Exp Med* 193: 255-261, 2001). Moreover, CRTH2 mediates the respiratory burst and degranulation of eosinophils (Gervais et al., *J Allergy Clin Immunol* 108: 982-988, 2001), induces the production of proinflammatory cytokines in Th2 cells (Xue et al., *J Immunol* 175: 6531-6536), and enhances the release of histamine from basophils (Yoshimura-Uchiyama et al., *Clin Exp Allergy* 34:1283-1290). Sequence variants of the gene encoding CRTH2, which differentially influence its mRNA stability, are shown to be associated with asthma (Huang et al., *Hum Mol Genet* 13, 2691-2697, 2004). Increased numbers of circulating T cells expressing CRTH2 have also been correlated with severity of atopic dermatitis (Cosmi et al., *Eur J Immunol* 30, 2972-2979, 2000). These findings suggest that CRTH2 plays a proinflammatory role in allergic diseases. Therefore, antagonists or partial agonists of CRTH2 are believed to be useful for treating disorders such as asthma, allergic inflammation, COPD, allergic rhinitis, and atopic dermatitis.

SUMMARY OF THE INVENTION

The invention is concerned with the compounds of formula I:

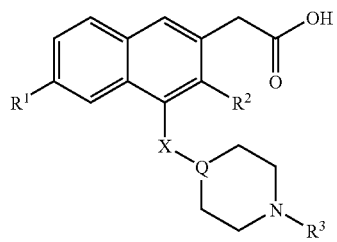

and pharmaceutically acceptable salts and esters thereof, wherein X, Q and $R^1$-$R^3$ are defined in the detailed description and claims. The invention is also concerned with the compounds of formula Z:

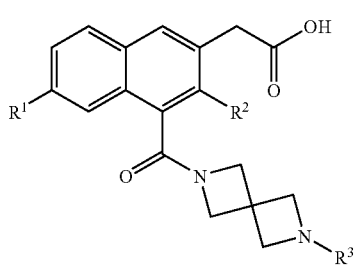

and pharmaceutically acceptable salts and esters thereof, wherein $R^1$-$R^3$ are defined in the detailed description and claims. In addition, the present invention relates to methods of manufacturing and using the compounds of formula I and Z as well as pharmaceutical compositions containing such compounds. The compounds of formula I and Z are antagonists or partial agonists at the CRTH2 receptor and may be useful in treating diseases and disorders associated with that receptor such as asthma.

DETAILED DESCRIPTION OF THE INVENTION

Unless otherwise indicated, the following specific terms and phrases used in the description and claims are defined as follows:

The term "moiety" refers to an atom or group of chemically bonded atoms that is attached to another atom or molecule by one or more chemical bonds thereby forming part of a molecule. For example, the variables $R^1$, $R^2$ and $R^3$ of formula I refer to moieties that are attached to the core structure of formula I by a covalent bond.

In reference to a particular moiety with one or more hydrogen atoms, the term "substituted" refers to the fact that at least one of the hydrogen atoms of that moiety is replaced by another substituent or moiety. For example, the term "lower alkyl substituted by halogen" refers to the fact that one or more hydrogen atoms of a lower alkyl (as defined below) is replaced by one or more halogen atoms (i.e, trifluoromethyl, difluoromethyl, fluoromethyl, chloromethyl, etc.).

The term "optionally substituted" refers to the fact that one or more hydrogen atoms of a moiety (with one or more hydrogen atoms) can be, but does not necessarily have to be, substituted with another substituent.

The term "alkyl" refers to an aliphatic straight-chain or branched-chain saturated hydrocarbon moiety having 1 to 20 carbon atoms. In particular embodiments the alkyl has 1 to 10 carbon atoms.

The term "lower alkyl" refers to an alkyl moiety having 1 to 7 carbon atoms. In particular embodiments the lower alkyl has 1 to 4 carbon atoms and in other particular embodiments the lower alkyl has 1 to 3 carbon atoms. Examples of lower alkyls include methyl, ethyl, propyl, isopropyl, butyl, isobutyl, sec-butyl and tert-butyl.

The term "lower cycloalkyl" refers to a saturated or partly unsaturated non-aromatic hydrocarbon ring moiety having 3 to 7 carbon atoms bonded together to form a ring structure. Examples of cycloalkyls include cyclopropyl, cyclobutyl, cyclopentyl, cyclohexyl and cycloheptyl.

The term "lower alkoxy" refers to the moiety —O—R, wherein R is lower alkyl as defined previously. Examples of lower alkoxy moieties include methoxy, ethoxy, n-propoxy, isopropoxy, n-butoxy, isobutoxy, sec-butoxy and tert-butoxy.

The term "lower alkylsulfonyl" refers to the moiety —S(O)$_2$—R, wherein R is lower alkyl as defined previously. Examples of lower alkylsulfonyls include methylsulfonyl and ethylsulfonyl.

The term "lower alkoxycarbonyl" refers to the moiety —C(O)—O—R, wherein R is lower alkyl as defined previously. An example of a lower alkoxycarbonyl is tert-butoxycarbonyl.

The term "halogen" refers to a moiety of fluoro, chloro, bromo or iodo.

Unless otherwise indicated, the term "hydrogen" or "hydro" refers to the moiety of a hydrogen atom (—H) and not H$_2$.

Unless otherwise indicated, the term "a compound of the formula" or "a compound of formula" or "compounds of the formula" or "compounds of formula" refers to any compound selected from the genus of compounds as defined by the formula (Including any pharmaceutically acceptable salt or ester of any such compound if not otherwise noted).

The term "pharmaceutically acceptable salts" refers to those salts which retain the biological effectiveness and properties of the free bases or free acids, which are not biologically or otherwise undesirable. Salts may be formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxalic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, N-acetylcystein and the like. In addition, salts may be prepared by the addition of an inorganic base or an organic base to the free acid. Salts derived from an inorganic base include, but are not limited to, the sodium, potassium, lithium, ammonium, calcium, and magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like.

The compounds of the present invention can be present in the form of pharmaceutically acceptable salts. The compounds of the present invention can also be present in the form of pharmaceutically acceptable esters (i.e., the methyl and ethyl esters of the acids of formula I to be used as prodrugs). The compounds of the present invention can also be solvated, i.e. hydrated. The solvation can be effected in the course of the manufacturing process or can take place i.e. as a consequence of hygroscopic properties of an initially anhydrous compound of formula I (hydration).

Compounds that have the same molecular formula but differ in the nature or sequence of bonding of their atoms or the arrangement of their atoms in space are termed "isomers." Isomers that differ in the arrangement of their atoms in space are termed "stereoisomers." Diastereomers are stereoisomers with opposite configuration at one or more chiral centers which are not enantiomers. Stereoisomers bearing one or more asymmetric centers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, 1 mg to about 1,000 mg, or 1 mg to 100 mg may be appropriate, although the lower and upper limits may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention is contemplated. Supplementary active compounds can also be incorporated into the compositions.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

In the practice of the method of the present invention, an effective amount of any one of the compounds of this invention or a combination of any of the compounds of this invention or a pharmaceutically acceptable salt or ester thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form of solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

In detail, the present invention relates to the compounds of formula I:

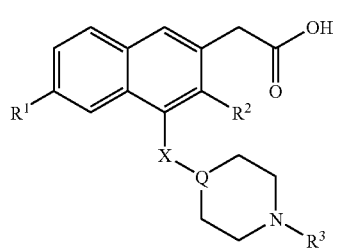

and pharmaceutically acceptable salts and esters thereof, wherein:

X is O and Q is C(H); or alternatively, X is C(O) and Q is N;

$R^1$ is selected from the group consisting of:
  (a) hydrogen,
  (b) halogen,
  (c) lower alkyl optionally substituted by fluoro,
  (d) lower alkoxy optionally substituted by fluoro,
  (e) lower alkylsulfonyl, and
  (f) cyano;

$R^2$ is hydrogen or lower alkyl; and $R^3$ is selected from the group consisting of:
  (a) phenyl, pyridinyl, or pyrimidinyl, wherein said phenyl, pyridinyl, or pyrimidinyl is optionally substituted by one or more substituents independently selected from the group consisting of: (1) halogen, (2) lower alkyl optionally substituted by fluoro; (3) lower alkoxy optionally substituted by fluoro, and (4) cyano;
  (b) lower alkoxycarbonyl; and
  (c) $S(O)_2$—$R^4$, C(O)—$R^4$, or C(O)—N(H)—$R^4$ wherein $R^4$ is selected from the group consisting of:
    (1) lower alkyl optionally substituted by fluoro,
    (2) lower cycloalkyl,
    (3) phenyl optionally substituted by: (i) halogen or (ii) lower alkyl optionally substituted by fluoro,
    (4) benzyl or phenylethyl, and
    (5) pyridinyl.

Unless indicated otherwise, the genus of formula I and any subgenera thereof encompass all possible stereoisomers (i.e., (R)-enantiomers, (S)-enantiomers, diastereomers) as well as racemic and scalemic mixtures thereof.

In one embodiment, the present invention is directed to the compounds of formula I or pharmaceutically acceptable salts or esters thereof wherein X is O and Q is C(H) as shown below in formula IA (a subgenus of formula I):

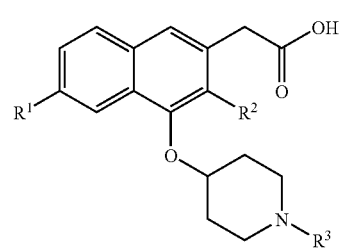

wherein $R^1$-$R^3$ are defined as in formula I.

In another embodiment, the present invention is directed to the compounds of formula I or pharmaceutically acceptable salts or esters thereof wherein X is C(O) and Q is N as shown below in formula IB (a subgenus of formula I):

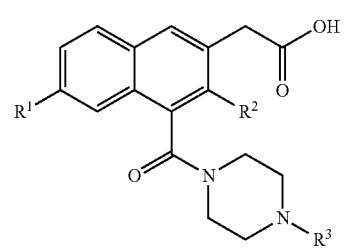

wherein $R^1$-$R^3$ are defined as in formula I.

In another embodiment, the present invention is directed to the compounds of formula I or pharmaceutically acceptable salts or esters thereof wherein $R^1$ is hydrogen.

In another embodiment, the present invention is directed to the compounds of formula I or pharmaceutically acceptable salts or esters thereof wherein $R^1$ is fluoro.

In another embodiment, the present invention is directed to the compounds of formula I or pharmaceutically acceptable salts or esters thereof wherein $R^1$ is methyl.

In another embodiment, the present invention is directed to the compounds of formula I or pharmaceutically acceptable salts or esters thereof wherein $R^1$ is methoxy.

In another embodiment, the present invention is directed to the compounds of formula I or pharmaceutically acceptable salts or esters thereof wherein $R^1$ is methylsulfonyl.

In another embodiment, the present invention is directed to the compounds of formula I or pharmaceutically acceptable salts or esters thereof wherein $R^1$ is cyano.

In another embodiment, the present invention is directed to the compounds of formula I or pharmaceutically acceptable salts or esters thereof wherein $R^2$ is hydrogen.

In another embodiment, the present invention is directed to the compounds of formula I or pharmaceutically acceptable salts or esters thereof wherein $R^2$ is methyl.

In another embodiment, the present invention is directed to the compounds of formula I or pharmaceutically acceptable salts or esters thereof wherein $R^3$ is phenyl.

In another embodiment, the present invention is directed to the compounds of formula I or pharmaceutically acceptable salts or esters thereof wherein $R^3$ is phenyl substituted once or twice with fluoro.

In another embodiment, the present invention is directed to the compounds of formula I or pharmaceutically acceptable salts or esters thereof wherein $R^3$ is phenyl substituted once or twice with chloro.

In another embodiment, the present invention is directed to the compounds of formula I or pharmaceutically acceptable salts or esters thereof wherein $R^3$ is phenyl substituted once or twice with trifluoromethyl.

In another embodiment, the present invention is directed to the compounds of formula I or pharmaceutically acceptable salts or esters thereof wherein $R^3$ is phenyl substituted once or twice with methoxy.

In another embodiment, the present invention is directed to the compounds of formula I or pharmaceutically acceptable salts or esters thereof wherein $R^3$ is phenyl substituted at the 4 position on the phenyl ring where such positions are indicated below in formula IC (a subgenus of formula I):

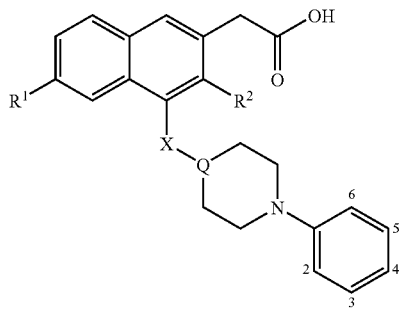

IC wherein X, Q, $R^1$ and $R^2$ are defined as in formula I.

In a more specific embodiment, the present invention is directed to the compounds of formula I or pharmaceutically acceptable salts or esters thereof wherein $R^3$ is phenyl substituted at the 4 position on the phenyl ring with chloro, fluoro, methyl, trifluoromethyl, or methoxy.

In another embodiment, the present invention is directed to the compounds of formula I or pharmaceutically acceptable salts or esters thereof wherein $R^3$ is phenyl substituted at the 3 or 5 positions on the phenyl ring with chloro, fluoro, methyl, trifluoromethyl, or methoxy.

In another embodiment, the present invention is directed to the compounds of formula I or pharmaceutically acceptable salts or esters thereof wherein $R^3$ is phenyl substituted at the 3 and 5 positions on the phenyl ring with chloro, fluoro, methyl, trifluoromethyl, or methoxy.

In another embodiment, the present invention is directed to the compounds of formula I or pharmaceutically acceptable salts or esters thereof wherein $R^3$ is —S(O)$_2$—$R^4$ and $R^4$ is lower cycloalkyl or lower alkyl optionally substituted by halogen.

In a more specific embodiment, the present invention is directed to the compounds of formula I or pharmaceutically acceptable salts or esters thereof wherein $R^3$ is —S(O)$_2$—$R^4$ and $R^4$ is methyl, ethyl, propyl, isopropyl, cyclopropyl, cyclopentyl, or trifluoromethyl.

In another embodiment, the present invention is directed to the compounds of formula I or pharmaceutically acceptable salts or esters thereof wherein $R^3$ is —S(O)$_2$—$R^4$ and $R^4$ is phenyl optionally substituted by halogen or lower alkyl.

In another embodiment, the present invention is directed to the compounds of formula I or pharmaceutically acceptable salts or esters thereof wherein $R^4$ is —S(O)$_2$—$R^4$ and $R^4$ is phenyl optionally substituted once or twice by fluoro.

In another embodiment, the present invention is directed to the compounds of formula I or pharmaceutically acceptable salts or esters thereof wherein $R^3$ is —C(O)—$R^4$ and $R^4$ is lower cycloalkyl or lower alkyl optionally substituted by halogen.

In a more specific embodiment, the present invention is directed to the compounds of formula I or pharmaceutically acceptable salts or esters thereof wherein $R^3$ is —C(O)—$R^4$ and $R^4$ is methyl, ethyl, propyl, isopropyl, cyclopropyl, cyclopentyl, or trifluoromethyl.

In another embodiment, the present invention is directed to the compounds of formula I or pharmaceutically acceptable salts or esters thereof wherein $R^3$ is —C(O)—$R^4$ and $R^4$ is phenyl optionally substituted by halogen or lower alkyl.

In a more specific embodiment, the present invention is directed to the compounds of formula I or pharmaceutically acceptable salts or esters thereof wherein $R^3$ is —C(O)—$R^4$ and $R^4$ is phenyl optionally substituted once or twice by fluoro.

In another embodiment, the present invention is directed to the compounds of formula I or pharmaceutically acceptable salts or esters thereof wherein $R^3$ is —C(O)—N(H)—$R^4$ and $R^4$ is lower cycloalkyl or lower alkyl optionally substituted by halogen.

In a more specific embodiment, the present invention is directed to the compounds of formula I or pharmaceutically acceptable salts or esters thereof wherein $R^3$ is —C(O)—N(H)—$R^4$ and $R^4$ is methyl, ethyl, propyl, isopropyl, cyclopropyl, cyclopentyl, or trifluoromethyl.

In another embodiment, the present invention is directed to the compounds of formula I or pharmaceutically acceptable salts or esters thereof wherein $R^3$ is —C(O)—N(H)—$R^4$ and $R^4$ is phenyl optionally substituted by halogen or lower alkyl.

In a more specific embodiment, the present invention is directed to the compounds of formula I or pharmaceutically acceptable salts or esters thereof wherein $R^3$ is —C(O)—N(H)—$R^4$ and $R^4$ is phenyl optionally substituted once or twice by fluoro.

In a more specific embodiment, the present invention is directed to the compounds of formula I or pharmaceutically acceptable salts or esters thereof wherein $R^3$ is pyridinyl.

In a more specific embodiment, the present invention is directed to the compounds of formula I or pharmaceutically acceptable salts or esters thereof wherein $R^3$ is acetyl.

In a more specific embodiment, the present invention is directed to the compounds of formula I or pharmaceutically acceptable salts or esters thereof wherein $R^3$ is tert-butoxycarbonyl.

In another independent embodiment, the present invention also relates to the compounds of formula Z:

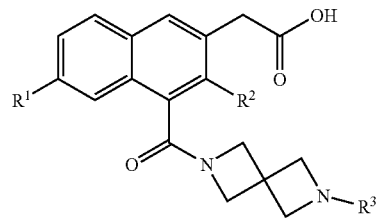

Z and pharmaceutically acceptable salts and esters thereof, wherein:
$R^1$ is selected from the group consisting of:
 (a) hydrogen,
 (b) halogen,
 (c) lower alkyl optionally substituted by fluoro, (d) lower alkoxy optionally substituted by fluoro,
(e) lower alkylsulfonyl, and
(f) cyano;

$R^2$ is hydrogen or lower alkyl; and
$R^3$ is $S(O)_2$—$R^4$ wherein $R^4$ is selected from the group consisting of:
(a) phenyl or benzyl, wherein said phenyl or benzyl is optionally substituted by one or more substituents of: (1) halogen or (2) lower alkyl optionally substituted by fluoro; and
(b) lower alkyl optionally substituted by fluoro.

Unless indicated otherwise, the genus of formula Z and any subgenera thereof encompass all possible stereoisomers (i.e., (R)-enantiomers, (S)-enantiomers, diastereomers) as well as racemic and scalemic mixtures thereof.

The present invention also relates to methods of manufacturing and using the compounds of formula Z as well as pharmaceutical compositions containing such compounds. The compounds of formula Z are also antagonists or partial agonists at the CRTH2 receptor and may be useful in treating diseases and disorders associated with that receptor such as asthma.

In one embodiment, the present invention is directed to the compounds of formula Z or pharmaceutically acceptable salts or esters thereof wherein $R^1$ is hydrogen.

In another embodiment, the present invention is directed to the compounds of formula Z or pharmaceutically acceptable salts or esters thereof wherein $R^1$ is fluoro.

In another embodiment, the present invention is directed to the compounds of formula Z or pharmaceutically acceptable salts or esters thereof wherein $R^1$ is methyl.

In another embodiment, the present invention is directed to the compounds of formula Z or pharmaceutically acceptable salts or esters thereof wherein $R^2$ is hydrogen.

In another embodiment, the present invention is directed to the compounds of formula Z or pharmaceutically acceptable salts or esters thereof wherein $R^2$ is methyl.

In another embodiment, the present invention is directed to the compounds of formula Z or pharmaceutically acceptable salts or esters thereof wherein $R^3$ is phenyl.

In another embodiment, the present invention is directed to the compounds of formula Z or pharmaceutically acceptable salts or esters thereof wherein $R^3$ is benzyl.

In a more specific embodiment, the present invention is directed to a compound of formula I or Z selected from the group consisting of:

[4-(4-Ethanesulfonyl-piperazine-1-carbonyl)-6-fluoro-3-methyl-naphthalen-2-yl]-acetic acid;
[4-(4-Ethanesulfonyl-piperazine-1-carbonyl)-6-fluoro-naphthalen-2-yl]-acetic acid;
[6-Fluoro-4-(4-methanesulfonyl-piperazine-1-carbonyl)-3-methyl-naphthalen-2-yl]-acetic acid;
{6-Fluoro-3-methyl-4-[4-(propane-2-sulfonyl)-piperazine-1-carbonyl]-naphthalen-2-yl}-acetic acid;
[6-Fluoro-3-methyl-4-(4-trifluoromethanesulfonyl-piperazine-1-carbonyl)-naphthalen-2-yl]-acetic acid;
[4-(4-Cyclopropanesulfonyl-piperazine-1-carbonyl)-6-fluoro-3-methyl-naphthalen-2-yl]-acetic acid;
{6-Fluoro-4-[4-(propane-1-sulfonyl)-piperazine-1-carbonyl]-naphthalen-2-yl}-acetic acid;
[4-(4-Cyclopentanesulfonyl-piperazine-1-carbonyl)-6-fluoro-3-methyl-naphthalen-2-yl]-acetic acid;
[4-(4-Benzenesulfonyl-piperazine-1-carbonyl)-6-fluoro-3-methyl-naphthalen-2-yl]-acetic acid;
[4-(6-Benzenesulfonyl-2,6-diaza-spiro[3.3]heptane-2-carbonyl)-6-fluoro-3-methyl-naphthalen-2-yl]-acetic acid;
[6-Fluoro-3-methyl-4-(6-phenylmethanesulfonyl-2,6-diaza-spiro[3.3]heptane-2-carbonyl)-naphthalen-2-yl]-acetic acid;
{6-Fluoro-4-[4-(4-fluoro-benzenesulfonyl)-piperazine-1-carbonyl]-3-methyl-naphthalen-2-yl}-acetic acid;
[6-Fluoro-3-methyl-4-(4-phenylmethanesulfonyl-piperazine-1-carbonyl)-naphthalen-2-yl]-acetic acid;
{6-Fluoro-4-[4-(2-fluoro-benzenesulfonyl)-piperazine-1-carbonyl]-3-methyl-naphthalen-2-yl}-acetic acid;
{4-[4-(3,4-Difluoro-benzenesulfonyl)-piperazine-1-carbonyl]-6-fluoro-3-methyl-naphthalen-2-yl}-acetic acid;
{6-Fluoro-4-[4-(3-fluoro-benzenesulfonyl)-piperazine-1-carbonyl]-3-methyl-naphthalen-2-yl}-acetic acid;
{4-[4-(2,4-Difluoro-benzenesulfonyl)-piperazine-1-carbonyl]-6-fluoro-3-methyl-naphthalen-2-yl}-acetic acid;
[4-(4-Benzenesulfonyl-piperazine-1-carbonyl)-6-trifluoromethyl-naphthalen-2-yl]-acetic acid;
[4-(4-Benzenesulfonyl-piperazine-1-carbonyl)-6-trifluoromethoxy-naphthalen-2-yl]-acetic acid;
{6-Fluoro-4-[4-(4-fluoro-phenyl)-piperazine-1-carbonyl]-3-methyl-naphthalen-2-yl}-acetic acid;
[6-Fluoro-3-methyl-4-(4-pyridin-2-yl-piperazine-1-carbonyl)-naphthalen-2-yl]-acetic acid;
{6-Fluoro-4-[4-(2-fluoro-phenyl)-piperazine-1-carbonyl]-3-methyl-naphthalen-2-yl}-acetic acid;
[6-Fluoro-3-methyl-4-(4-phenyl-piperazine-1-carbonyl)-naphthalen-2-yl]-acetic acid;
[6-Fluoro-3-methyl-4-(4-pyrimidin-2-yl-piperazine-1-carbonyl)-naphthalen-2-yl]-acetic acid;
[6-Fluoro-3-methyl-4-(4-m-tolyl-piperazine-1-carbonyl)-naphthalen-2-yl]-acetic acid;
{6-Fluoro-3-methyl-4-[4-(3-trifluoromethyl-phenyl)-piperazine-1-carbonyl]-naphthalen-2-yl}-acetic acid;
{6-Fluoro-4-[4-(2-methoxy-phenyl)-piperazine-1-carbonyl]-3-methyl-naphthalen-2-yl}-acetic acid;
{6-Fluoro-4-[4-(3-methoxy-phenyl)-piperazine-1-carbonyl]-3-methyl-naphthalen-2-yl}-acetic acid;
{4-[4-(2-Ethyl-phenyl)-piperazine-1-carbonyl]-6-fluoro-3-methyl-naphthalen-2-yl}-acetic acid;
{4-[4-(3,5-Bis-trifluoromethyl-phenyl)-piperazine-1-carbonyl]-6-fluoro-3-methyl-naphthalen-2-yl}-acetic acid;
{6-Fluoro-4-[4-(4-methoxy-phenyl)-piperazine-1-carbonyl]-3-methyl-naphthalen-2-yl}-acetic acid;
{4-[4-(2,4-Difluoro-phenyl)-piperazine-1-carbonyl]-6-fluoro-3-methyl-naphthalen-2-yl}-acetic acid;
{4-[4-(3,5-Dimethoxy-phenyl)-piperazine-1-carbonyl]-6-fluoro-3-methyl-naphthalen-2-yl}-acetic acid;
{6-Fluoro-3-methyl-4-[4-(2-trifluoromethyl-phenyl)-piperazine-1-carbonyl]-naphthalen-2-yl}-acetic acid;
[6-Fluoro-3-methyl-4-(4-p-tolyl-piperazine-1-carbonyl)-naphthalen-2-yl]-acetic acid;
{4-[4-(3,5-Dichloro-phenyl)-piperazine-1-carbonyl]-6-fluoro-3-methyl-naphthalen-2-yl}-acetic acid;
{4-[4-(4-Chloro-phenyl)-piperazine-1-carbonyl]-6-fluoro-3-methyl-naphthalen-2-yl}-acetic acid;
{6-Fluoro-3-methyl-4-[4-(4-trifluoromethyl-phenyl)-piperazine-1-carbonyl]-naphthalen-2-yl}-acetic acid;
{4-[4-(2-Chloro-phenyl)-piperazine-1-carbonyl]-6-fluoro-3-methyl-naphthalen-2-yl}-acetic acid;
{4-[4-(3-Chloro-phenyl)-piperazine-1-carbonyl]-6-fluoro-3-methyl-naphthalen-2-yl}-acetic acid;
{6-Fluoro-3-methyl-4-[4-(5-trifluoromethyl-pyridin-2-yl)-piperazine-1-carbonyl]-naphthalen-2-yl}-acetic acid;
{4-[4-(3,5-Dichloro-pyridin-4-yl)-piperazine-1-carbonyl]-6-fluoro-3-methyl-naphthalen-2-yl}-acetic acid;
{4-[4-(4-Cyano-phenyl)-piperazine-1-carbonyl]-6-fluoro-3-methyl-naphthalen-2-yl}-acetic acid, 4-(3-Carboxymethyl-7-fluoro-naphthalen-1-yloxy)-piperidine-1-carboxylic acid tert-butyl ester;
[6-Fluoro-4-(1-methanesulfonyl-piperidin-4-yloxy)-naphthalen-2-yl]-acetic acid;
[4-(1-Ethanesulfonyl-piperidin-4-yloxy)-6-fluoro-naphthalen-2-yl]-acetic acid;
{6-Fluoro-4-[1-(propane-2-sulfonyl)-piperidin-4-yloxy]-naphthalen-2-yl}-acetic acid;
[4-(1-Cyclopropanesulfonyl-piperidin-4-yloxy)-6-fluoro-naphthalen-2-yl]-acetic acid;
[4-(1-Cyclopentanesulfonyl-piperidin-4-yloxy)-6-fluoro-naphthalen-2-yl]-acetic acid;
[4-(1-Benzenesulfonyl-piperidin-4-yloxy)-6-fluoro-naphthalen-2-yl]-acetic acid;
{6-Fluoro-4-[1-(3-fluoro-benzenesulfonyl)-piperidin-4-yloxy]-naphthalen-2-yl}-acetic acid;
{6-Fluoro-4-[1-(4-fluoro-benzenesulfonyl)-piperidin-4-yloxy]-naphthalen-2-yl}-acetic acid;
{6-Fluoro-4-[1-(pyridine-3-sulfonyl)-piperidin-4-yloxy]-naphthalen-2-yl}-acetic acid;
[6-Fluoro-4-(1-phenylmethanesulfonyl-piperidin-4-yloxy)-naphthalen-2-yl]-acetic acid;
[4-(1-Acetyl-piperidin-4-yloxy)-6-fluoro-naphthalen-2-yl]-acetic acid;
[6-Fluoro-4-(1-propionyl-piperidin-4-yloxy)-naphthalen-2-yl]-acetic acid;
[6-Fluoro-4-(1-isobutyryl-piperidin-4-yloxy)-naphthalen-2-yl]-acetic acid;
[4-(1-Cyclopropanecarbonyl-piperidin-4-yloxy)-6-fluoro-naphthalen-2-yl]-acetic acid;
[4-(1-Cyclopentanecarbonyl-piperidin-4-yloxy)-6-fluoro-naphthalen-2-yl]-acetic acid;
[4-(1-Benzoyl-piperidin-4-yloxy)-6-fluoro-naphthalen-2-yl]-acetic acid;
{6-Fluoro-4-[1-(2-fluoro-benzoyl)-piperidin-4-yloxy]-naphthalen-2-yl}-acetic acid;
{6-Fluoro-4-[1-(3-fluoro-benzoyl)-piperidin-4-yloxy]-naphthalen-2-yl}-acetic acid;
{6-Fluoro-4-[1-(4-fluoro-benzoyl)-piperidin-4-yloxy]-naphthalen-2-yl}-acetic acid;
[6-Fluoro-4-(1-phenylacetyl-piperidin-4-yloxy)-naphthalen-2-yl]-acetic acid;
[4-(1-Ethylcarbamoyl-piperidin-4-yloxy)-6-fluoro-naphthalen-2-yl]-acetic acid;
{6-Fluoro-4-[1-(2-fluoro-phenylcarbamoyl)-piperidin-4-yloxy]-naphthalen-2-yl}-acetic acid;
{6-Fluoro-4-[1-(3-fluoro-phenylcarbamoyl)-piperidin-4-yloxy]-naphthalen-2-yl}-acetic acid;
{6-Fluoro-4-[1-(4-fluoro-phenylcarbamoyl)-piperidin-4-yloxy]-naphthalen-2-yl}-acetic acid;
[6-Fluoro-4-(1-phenethylcarbamoyl-piperidin-4-yloxy)-naphthalen-2-yl]-acetic acid and any pharmaceutically acceptable salt or ester thereof.

General Synthesis of Compounds According to the Invention

Generally, compounds of formula I and Z can be prepared according to the schemes illustrated below. Unless otherwise indicated, the variables such as X, Q, $R^1$, $R^2$, $R^3$, and $R^4$ with respect to synthesizing the compounds of formula I are defined in the same manner as defined previously for the genus of formula I. Likewise, unless otherwise indicated, the variables such as $R^1$, $R^2$, $R^3$, and $R^4$ with respect to synthesizing the compounds of formula Z are defined in the same manner as defined previously for the genus of formula Z. The compounds of the present invention may also be prepared by any conventional means and suitable processes for synthesizing specific compounds are additionally provided in the examples.

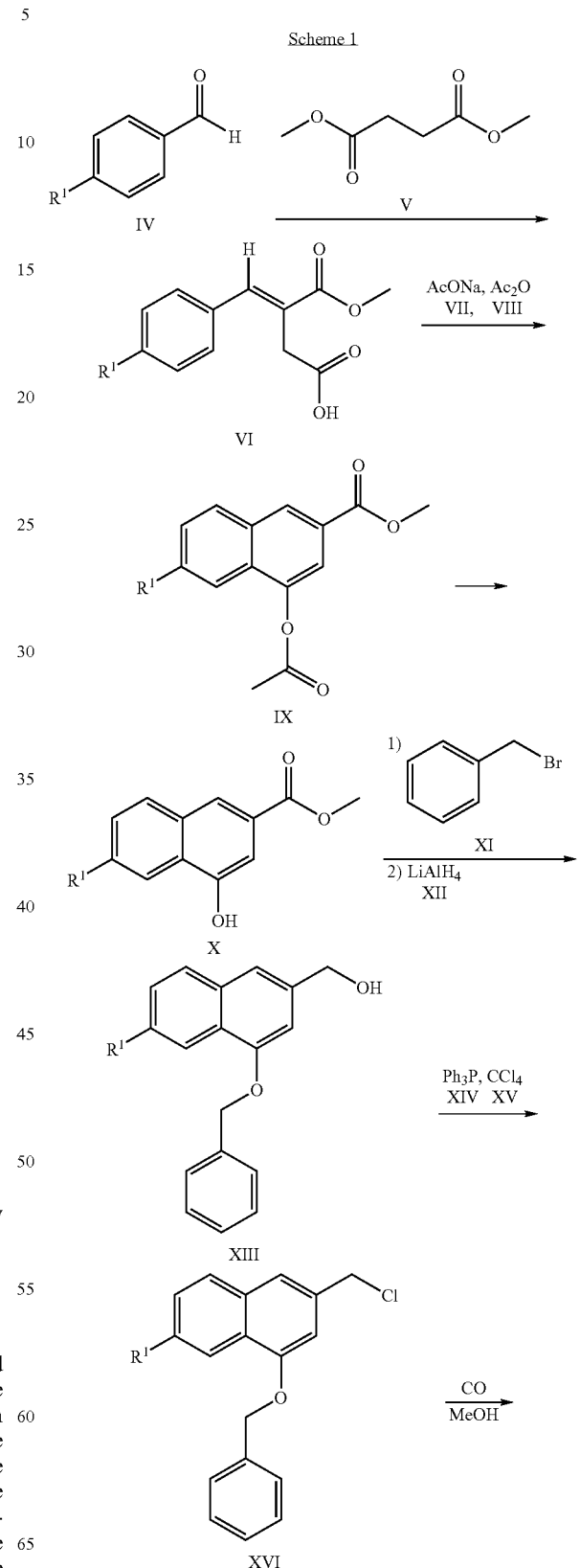

Scheme 1

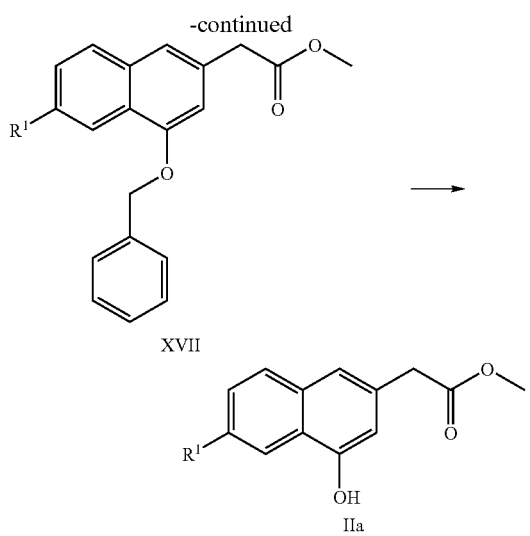

The key intermediates of formula IIa can be prepared according to Scheme 1. In this process, the Stobbe condensation between the para-substituted benzaldehydes IV and dimethyl succinate (V) gives the unsaturated acids VI, which subsequently undergo cyclization in the presence of sodium acetate (VII) and acetic anhydride (VIII) to produce the naphthalene derivatives IX. The acetates IX are then converted to the corresponding hydroxyl analogues X by a deacetylation reaction. A nucleophilic substitution reaction of the hydroxyl compounds X with benzyl bromide (XI), followed by reduction of the resulting products with lithium aluminum hydride (XII) affords the alcohols XIII. The alcohols XIII are then converted to the chlorides XVI by treatment with carbon tetrachloride (XV) and triphenylphosphine (XIV). Conversion of the chlorides XVI to the methyl esters XVII can be accomplished by a palladium catalyzed carbonylation reaction in methanol. Hydrogenolysis of benzyl ethers XVII affords the intermediates IIa.

In the first step outlined in Scheme 1, the unsaturated acids VI can be prepared by a condensation between the para-substituted benzaldehydes IV and dimethyl succinate (V). The reaction can be carried out in the presence of a base such as sodium methoxide, lithium methoxide, sodium tert-butoxide, sodium hydride or potassium tert-butoxide, in an organic solvent such as methanol, tert-butanol, toluene, or mixtures thereof, at a temperature between room temperature and 90° C. for several hours (reference: Dian, Y. L. et al., *Tetrahedron Lett.*, 32 (1991) 5255).

Cyclization of the unsaturated acids VI to generate the naphthalene derivatives IX can be achieved by treatment of the unsaturated acids VI with sodium acetate (VII) and acetic anhydride (VIII) at a temperature between room temperature and 140° C. for 0.5 to 12 hours (references: Boger, D. L. et al., *J. Org. Chem.* 61 (1996) 4894-4912; Kim, M. et al., *J. Org. Chem.* 69 (2004) 6945-6948).

The acetates IX can be converted to the corresponding hydroxyl compounds X in the presence of a base such as sodium methoxide, potassium tert-butoxide, potassium carbonate, or sodium bicarbonate, in a solvent such as methanol, water, or mixtures thereof, at a temperature between room temperature and 80° C. for 10 minutes to several hours (reference: Kim, M. et al., *J. Org. Chem.* 69 (2004) 6945-6948).

Treatment of the hydroxyl compounds X with benzyl bromide (XI) affords the corresponding benzyl ethers. The reaction can be carried out in the presence of a base such as potassium carbonate, or cesium carbonate, in a solvent such as acetone, acetonitrile, or N,N-dimethylformamide at a temperature between room temperature and 60° C. for several hours.

Reduction of the above benzyl ethers with lithium aluminum hydride (XII) affords the alcohols XIII. The reaction can be carried out in an inert solvent such as tetrahydrofuran, diethyl ether, toluene or mixtures thereof, at a temperature between room temperature and 80° C. for several hours (reference: Chan W. K. et al., *J. Med. Chem.* 39 (1996) 3756-3768).

The chlorides XVI can be prepared by treatment of the alcohols XIII with carbon tetrachloride (XV) and triphenylphosphine (XIV) in an inert organic solvent such as toluene, acetonitrile, dichloromethane, N,N-dimethylformamide, or tetrahydrofuran, at a temperature between 0° C. and 120° C. for several hours (reference: Kozhinov, D. V. et al., *J. Org. Chem.* 69 (2004) 1378-1379).

Conversion of the chlorides XVI to the methyl esters XVII can be accomplished by a palladium catalyzed carbonylation reaction under an atmospheric pressure of carbon monoxide in methanol. The reaction can be carried out in the presence of a palladium catalyst such as bis(triphenylphosphine)dichloropalladium(II) (Pd(PPh$_3$)$_2$Cl$_2$), palladium(II) acetate (Pd(OAc)$_2$), tetrakis(triphenylphosphine)palladium(0) (Pd(PPh$_3$)$_4$), or tris(dibenzylideneacetone)dipalladium(0) (Pd$_2$(dba)$_3$), in the presence or absence of a phosphine ligand such as tricyclohexylphosphine, or triphenylphosphine, at a temperature between room temperature and 90° C. for 10 minutes to several hours (reference: Kozhinov, D. V. et al., *J. Org. Chem.* 69 (2004) 1378-1379).

Hydrogenolysis of benzyl ethers XVII affords the intermediates IIa. The reaction can be carried out in the presence of 10% palladium on carbon under an atmospheric pressure of hydrogen, in an organic solvent such as ethyl acetate, methanol, or ethanol, at room temperature for several hours.

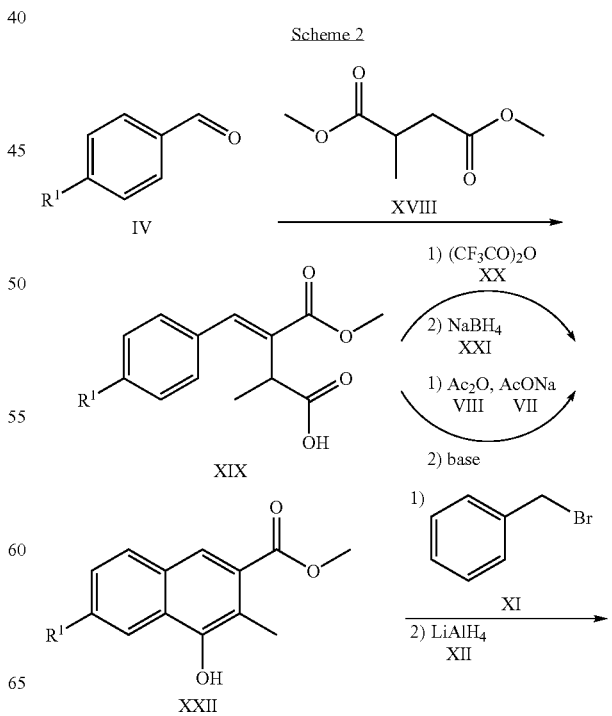

Scheme 2

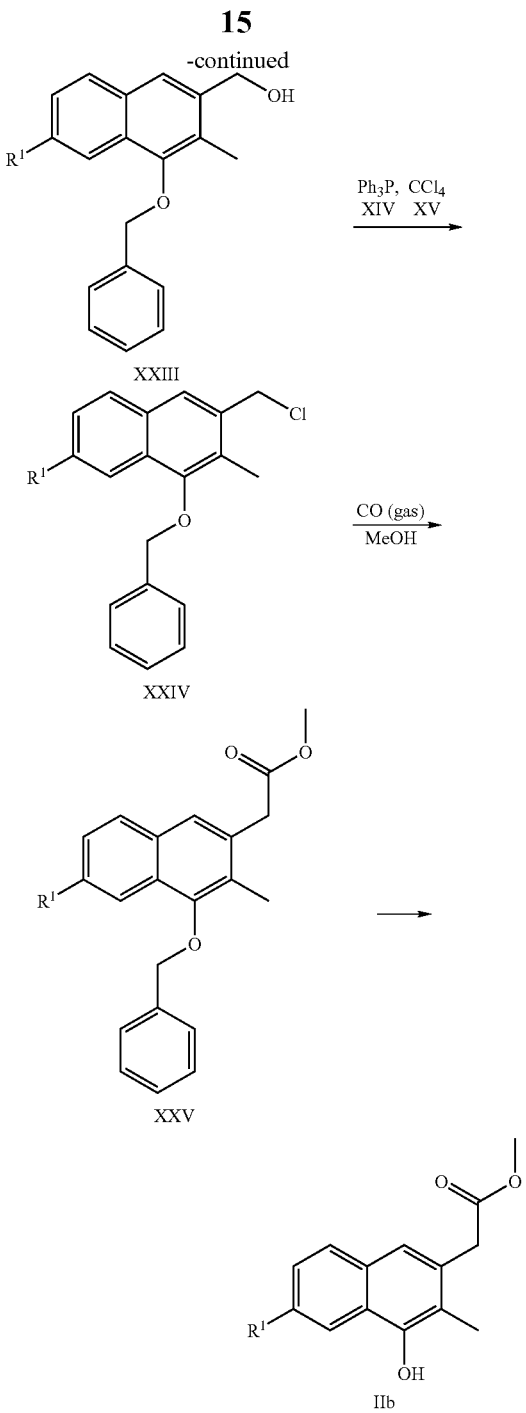

with triphenylphosphine (XIV) and carbon tetrachloride (XV). The chlorides XXIV can be converted to the methyl esters XXV by a palladium catalyzed carbonylation reaction in methanol. Hydrogenolysis of the methyl esters XXV affords the intermediate IIb.

In the first step outlined in Scheme 2, the unsaturated acids XIX can be prepared by a condensation between the para-substituted benzaldehydes IV and dimethyl 2-methyl-succinate (XVIII). The reaction can be carried out in the presence of a base such as sodium methoxide, lithium methoxide, sodium tert-butoxide, sodium hydride, or potassium tert-butoxide, in an organic solvent such as methanol, tert-butanol, toluene, or mixtures thereof, at a temperature between room temperature and 90° C. for several hours (references: Liu, J. et al., *Org. Lett.* 4 (2002) 3521-3524; Bloomer, J. L. et al., *J. Org. Chem.* 58 (1993) 7906-7912).

The naphthalen-1-ol derivatives XXII can be prepared by a cyclization reaction of the intermediates XIX followed by reduction. Cyclization of the unsaturated acids XIX can be achieved by treatment with trifluoroacetic anhydride (XX) and triethylamine in an inert organic solvent such as tetrahydrofuran, or dichloromethane at room temperature. The subsequent reduction with sodium borohydride (XXI) can be carried out in an alcoholic solvent such as methanol at a temperature between 0° C. and room temperature (reference: Fuganti, C. et al., *J. Chem. Res.* (S) 1998, 638-639).

Alternatively, the naphthalen-1-ol derivatives XXII can be prepared in a manner analogous to the one described in Scheme 1. Cyclization of the unsaturated acids XIX can be achieved by treatment with sodium acetate (VII) and acetic anhydride (VIII) at a temperature between room temperature and 140° C. for 0.5 to 12 hours. The resulting acetates can be converted to the corresponding hydroxyl analogues XXII by treatment with a base such as sodium methoxide, potassium tert-butoxide, potassium carbonate, or sodium bicarbonate, in a solvent such as methanol, water or mixtures thereof, at a temperature between room temperature and 80° C. for 10 minutes to several hours (references: Boger, D. L. et al., *J. Org. Chem.* 61 (1996) 4894-4912; Kim, M. et al., *J. Org. Chem.* 69 (2004) 6945-6948).

Treatment of the hydroxyl compounds XXII with benzyl bromide (XI) affords the corresponding benzyl ethers. The reaction can be carried out in the presence of a base such as potassium carbonate, or cesium carbonate, in a solvent such as acetone, acetonitrile, or N,N-dimethylformamide at a temperature between room temperature and 60° C. for several hours.

Reduction of the ester moieties in the above benzyl ethers with lithium aluminum hydride (XII) affords the alcohols XXIII. The reaction can be carried out in an inert solvent such as tetrahydrofuran, diethyl ether, toluene or mixtures thereof, at a temperature between room temperature and 80° C. for several hours.

The reaction of the alcohols XXIII with carbon tetrachloride (XV) in the presence of triphenylphosphine (XIV) can be carried out in an inert organic solvent such as tetrahydrofuran, acetonitrile, toluene, N,N-dimethylformamide, or dichloromethane, at a temperature between 0° C. and 120° C. for several hours (reference: Kozhinov, D. V. et al., *J. Org. Chem.* 69 (2004) 1378-1379).

The key intermediates of formula IIb can be prepared according to Scheme 2. In this process, the Stobbe condensation between the para-substituted benzaldehydes IV and dimethyl 2-methyl-succinate (XVIII) affords the unsaturated acids XIX. Cyclization of the unsaturated acids XIX using trifluoroacetic anhydride (XX) followed by reduction with sodium borohydride (XXI) affords the naphthalen-1-ol derivatives XXII. Alternatively, the naphthalen-1-ol derivatives XXII can be obtained by treatment with sodium acetate (VII) and acetic anhydride (VIII) followed by a base. Treatment of compounds XXII with benzyl bromide (XI), followed by reduction with lithium aluminum hydride (XII) affords the alcohols XXIII. The alcohols XXIII are then converted to the corresponding chlorides XXIV by treatment Conversion of the chlorides XXIV to the methyl esters XXV can be accomplished by a palladium catalyzed carbonylation reaction under an atmospheric pressure of carbon monoxide in methanol. The reaction can be carried out in the presence of a palladium catalyst such as bis(triphenylphosphine)dichloropalladium(II) (Pd(PPh$_3$)$_2$Cl$_2$), palladium(II) acetate (Pd(OAc)$_2$), tetrakis(triphenylphosphine)palladium (0) (Pd(PPh$_3$)$_4$), or tris(dibenzylideneacetone)dipalladium (0) (Pd$_2$(dba)$_3$), in the presence or absence of a phosphine ligand such as tricyclohexylphosphine or triphenylphosphine at a temperature between room temperature and 90° C. for 10 minutes to several hours (reference: Kozhinov, D. V. et al., *J. Org. Chem.* 69 (2004) 1378-1379).

Hydrogenolysis of benzyl ethers XXV affords the intermediates IIb. The reaction can be conveniently accomplished in the presence of 10% palladium on carbon under an atmospheric pressure of hydrogen, in an organic solvent such as ethyl acetate, methanol, or ethanol, at room temperature for several hours.

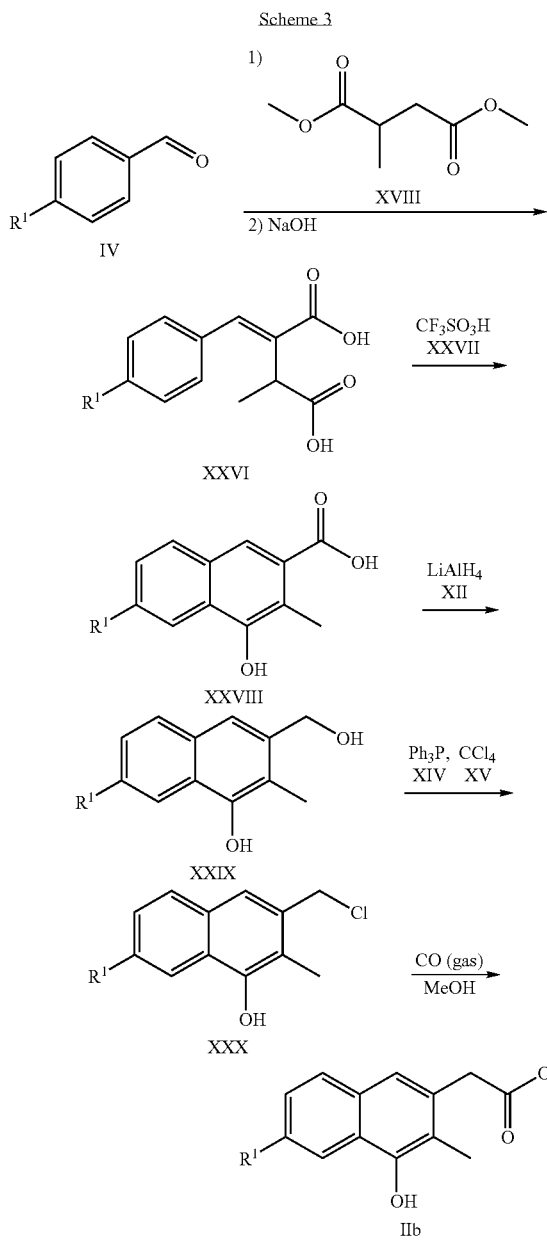

Alternatively, the hydroxyl intermediates IIb can be prepared according to Scheme 3. In this process, the Stobbe condensation reaction between the benzaldehydes IV and dimethyl 2-methyl-succinate (XVIII) followed by hydrolysis affords the unsaturated diacids XXVI. Cyclization of the unsaturated diacids XXVI followed by reduction affords compounds XXIX. Treatment of compounds XXIX with carbon tetrachloride (XV) and triphenylphosphine (XIV) affords the corresponding chlorides XXX. The chlorides XXX can be converted to the methyl esters IIb by a palladium catalyzed carbonylation reaction.

In this process, the Stobbe condensation can be carried out in the presence of a base such as sodium hydride, in an organic solvent such as toluene, at room temperature for several hours. The unsaturated diacids XXVI can be formed by treatment of the products of condensation with an aqueous inorganic base such as sodium hydroxide, in an organic solvent such as toluene, at a temperature between room temperature and 100° C. for several hours.

Cyclization of the diacids XXVI can be achieved by treatment of the diacids with trifluoromethanesulfonic acid (XXVII), at room temperature for several hours.

Reduction of the carboxyl moieties in the intermediates XXVIII with lithium aluminum hydride (XII) affords the alcohols XXIX. The reaction can be carried out in an inert organic solvent such as tetrahydrofuran, diethyl ether, toluene or mixtures thereof, at a temperature between room temperature and 80° C. for several hours.

The reaction of the alcohols XXIX with carbon tetrachloride (XV) in the presence of triphenylphosphine (XIV) can be carried out in an inert organic solvent such as tetrahydrofuran, acetonitrile, toluene, N,N-dimethylformamide, or dichloromethane, at a temperature between 0° C. and 120° C. for several hours.

Conversion of the chlorides XXX to the intermediates IIb can be accomplished by a carbonylation reaction, in a manner analogous to the one described in Scheme 1 for the preparation of the methyl esters XVII.

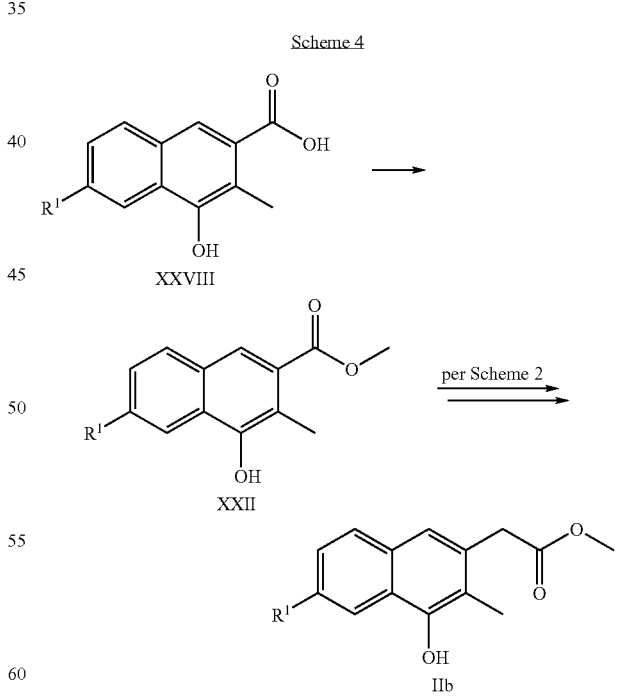

Alternatively, intermediates IIb may be prepared according to Scheme 4 starting from the 4-hydroxy-naphthalene carboxylic acid compounds XXVIII (prepared as described above in Scheme 3). Esterification of XXVIII forms the naphthalene carboxylic acid methyl esters XXII, (previously described in Scheme 2. Conversion of XXII to intermediates IIb can occur using the methods described in Scheme 2.

Intermediates XXVIII can be readily converted to the 4-hydroxy-naphthalene carboxylic acid methyl ester intermediates XXII in the presence of a catalytic amount of concentrated sulfuric acid and an excess of methanol at temperatures between room temperature and 80° C. for several hours. Alternatively, the esterification reaction can be carried out in the presence of thionyl chloride and an excess of methanol at temperatures between 65° C. and 80° C. for several hours. Compounds of type XXII thus formed can be transformed into intermediates IIb using the process described above in Scheme 2.

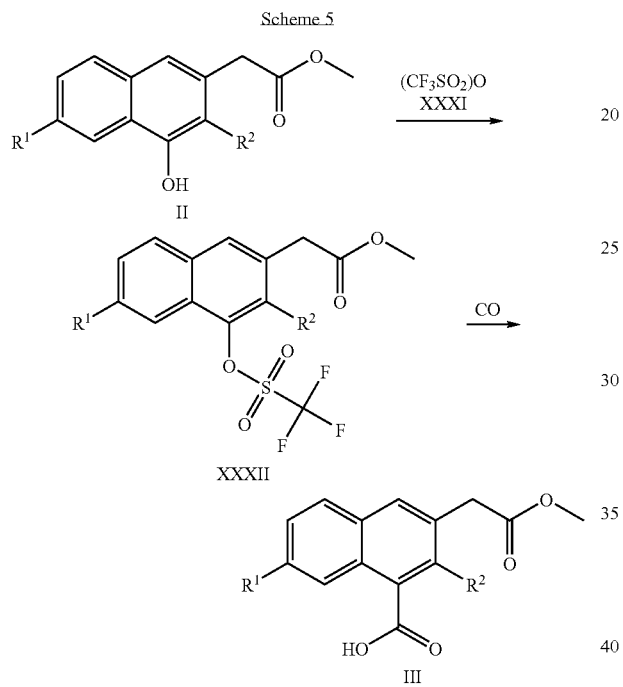

The key intermediates III can be prepared according to Scheme 5. In this process, treatment of the hydroxyl compounds II [which encompasses the above compounds IIa ($R^2$=hydrogen) and IIb ($R^2$=methyl)] with trifluoromethanesulfonic anhydride (XXXI) affords the triflates XXXII, which are then converted to the carboxylic acids III by a palladium catalyzed carbonylation reaction.

The hydroxyl compounds II can be converted to the triflates XXXII by treatment with trifluoromethanesulfonic anhydride (XXXI). The reaction can be carried out in the presence of a base such as pyridine, triethylamine, N,N-diisopropylethylamine, 2,6-dimethylpyridine, 4-dimethylaminopyridine, 2,4,6-trimethylpyridine, or potassium carbonate, in a suitable solvent such as dichloromethane, chloroform or acetonitrile, at a temperature between −78° C. and room temperature for 30 minutes to several hours (reference: Chan W. K. et al., *J. Med. Chem.* 39 (1996) 3756-3768).

Conversion of the triflates XXXII to the acids III can be accomplished by a palladium catalyzed carbonylation reaction under carbon monoxide (15-30 psi) in a mixture of water and an organic solvent such as N,N-dimethylformamide, or dimethyl sulfoxide. The reaction can be carried out in the presence of a palladium catalyst such as palladium(II) acetate ($Pd(OAc)_2$), in the presence or absence of a phosphine ligand such as 1,3-diphenylphosphinopropane, or 1,1'-bis(diphenylphosphino)ferrocene, and a base such as triethylamine, or potassium carbonate at a temperature between room temperature and 65° C. for several hours (references: Chen L. et al., *Bioorg. Med. Chem. Lett.* 12 (2002) 137-140; Cai C. et al., *Tetrahedron* 61 (2005) 6836-6838).

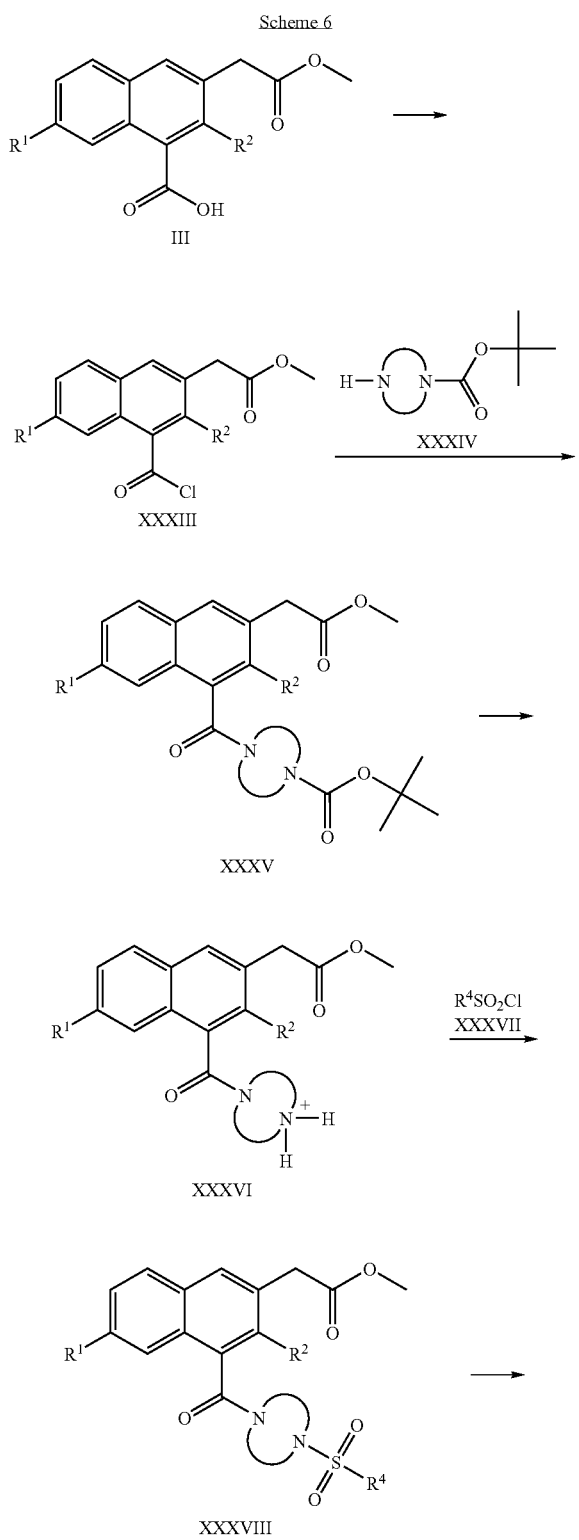

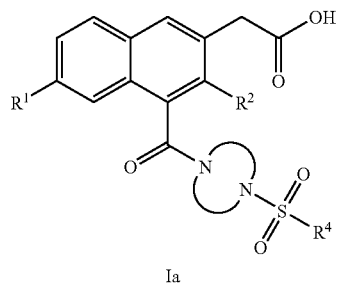

Ia

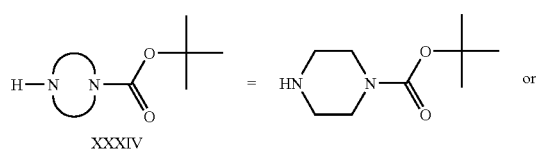

XXXIV

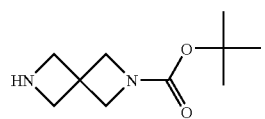

The compounds of interest of formula Ia can be prepared according to Scheme 6. In this process, treatment of the acids III with oxalyl chloride or thionyl chloride affords the carbonyl chlorides XXXIII. The reactions of the carbonyl chlorides XXXIII with the amines XXXIV affords the amides XXXV. The protected amides MOW can be converted to the corresponding amine salts XXXVI under acidic conditions. Sulfonylation of the amine salts XXXVI with the sulfonyl chlorides XXXVII, followed by a hydrolysis reaction, affords the compounds of interest of formula Ia.

In the first step of this process, conversion of the acids III to the carbonyl chlorides XXXIII can be achieved by treatment of the acids III with oxalyl chloride or thionyl chloride in the presence or absence of N,N-dimethylformamide, in an inert organic solvent such as dichloromethane, tetrahydrofuran, or toluene, at a temperature between room temperature and 110° C. for several hours.

The reactions of the carbonyl chlorides XXXIII with the amines XXXIV generate the amides XXXV. The reactions can be carried out in the presence of a base such as triethylamine, pyridine, or 4-dimethylaminopyridine, in a suitable inert solvent such as dichloromethane, acetonitrile, 1,4-dioxane, or tetrahydrofuran and mixtures thereof, at room temperature for several hours.

The protected amides XXXV can be converted to the corresponding amine salts XXXVI under acidic conditions. The reaction can be carried out in a solution of hydrogen chloride in methanol or a solution of trifluoroacetic acid in dichloromethane at room temperature for several hours.

Sulfonylation of the amine salts XXXVI with sulfonyl chlorides XXXVII affords the sulfonamides XXXVIII. The reaction can be carried out in the presence of a base such as triethylamine, pyridine, or 4-dimethylaminopyridine in a suitable inert solvent such as dichloromethane, acetonitrile, 1,4-dioxane, tetrahydrofuran or mixtures thereof, at room temperature for several hours.

Hydrolysis of the sulfonamides XXXVIII affords the compounds of interest of formula Ia. The reaction can be carried out in the presence of an aqueous inorganic base such as lithium hydroxide, sodium hydroxide, or potassium hydroxide in an inert solvent such as 1,4-dioxane or tetrahydrofuran at room temperature for several hours.

Scheme 7

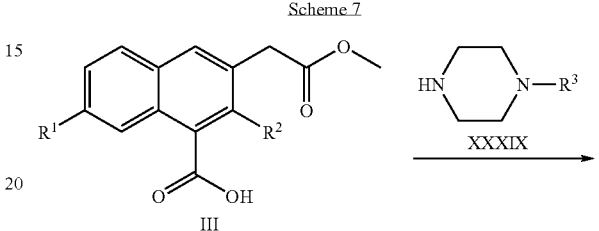

III

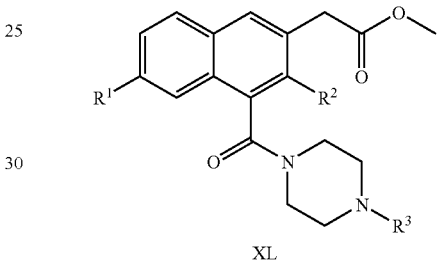

XL

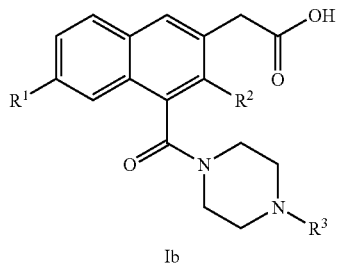

Ib

The compounds of interest of formula Ib can be prepared according to Scheme 7. Coupling of the acids III with the amines XXXIX, followed by a hydrolysis reaction of the resulting esters XL, affords the compounds of interest of formula Ib.

The amides XL can be prepared by coupling of the acids III with the amines XXXIX. The reaction can be carried out in the presence of bromo-tris-pyrrolidino phosphonium hexafluorophosphate (PyBrop) and N,N-diisopropylethylamine in an organic solvent such as N,N-dimethylformamide, at room temperature for several hours.

Hydrolysis of the methyl ester moieties of the amides XL affords the compounds of interest of formula Ib. The reaction can be carried out in the presence of an aqueous inorganic base such as lithium hydroxide, sodium hydroxide, or potassium hydroxide in an inert solvent such as 1,4-dioxane or tetrahydrofuran at room temperature for several hours.

Scheme 8

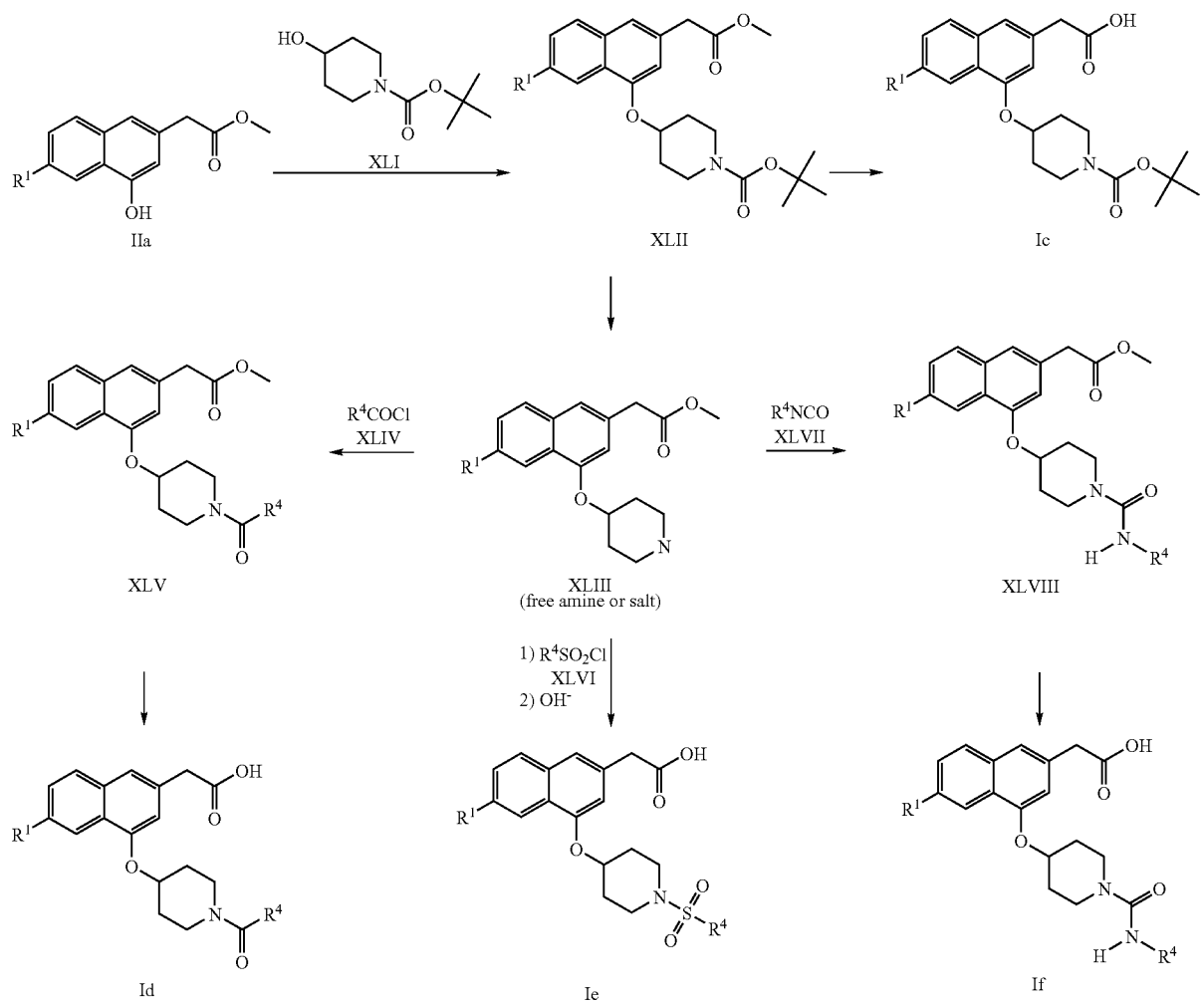

The compounds of interest of formula Ic, Id, Ie and If can be prepared according to Scheme 8. In this process, the intermediates IIa can be converted to the ethers XLII by a Mitsunobu reaction. Hydrolysis of the methyl ester moieties of the ethers XLII affords the compounds of interest of formula Ic. The protected amine groups in XLII are converted to the corresponding amines XLIII under acidic conditions, followed by treatment with a base to generate the free amines. Reaction of the amines XLIII with the carbonyl chlorides XLIV, followed by a hydrolysis reaction affords the compounds of interest of formula Id. Sulfonylation of the amines XLIII with the sulfonyl chlorides XLVI, followed by a hydrolysis reaction affords the compounds of interest of formula Ie. Treatment of the amines XLIII with the isocyanates XLVII, followed by a hydrolysis reaction affords the compounds of interest of formula If.

The intermediates IIa can be converted to the ethers XLII by a Mitsunobu reaction with 4-hydroxy-piperidine-1-carboxylic acid tert-butyl ester (XLI). The reaction can be carried out in the presence of diethyl azodicarboxylate (DEAD), diisopropyl azodicarboxylate (DIAD), or di-p-chlorobenzyl azodicarboxylate (DCAD) and triphenylphosphine, in an inert organic solvent such as toluene, dichloromethane, tetrahydrofuran, or acetonitrile, at a temperature between room temperature and 70° C. for 20 minutes to several hours (Lizarzaburu M. E. et al., *Tetrahedron Lett.* 43 (2002) 2157-2159).

The intermediates XLII can be converted to the corresponding amine salts by treatment under acidic conditions The reaction can be carried out in a solution of hydrogen chloride in methanol or a solution of trifluoroacetic acid in dichloromethane at room temperature for several hours.

The amine salts can be converted the corresponding amines XLIII by treatment with a base. The generation of the free amines can be carried out in an organic solvent such as dichloromethane or ethyl acetate, by treatment with an aqueous solution of a base such as sodium hydroxide, sodium carbonate, or sodium bicarbonate at room temperature.

Reaction of the amines XLIII with the carbonyl chlorides XLIV affords the amides XLV. The reaction can be carried out in the presence of a base such as triethylamine, pyridine, or 4-dimethylaminopyridine, in a suitable inert solvent such as dichloromethane, acetonitrile, 1,4-dioxane, tetrahydrofuran or mixtures thereof, at room temperature for several hours.

Sulfonylation of the amines XLIII with the sulfonyl chlorides XLVI affords the corresponding sulfonamides. The reaction can be carried out in the presence of a base such as triethylamine, pyridine, or 4-dimethylaminopyridine in a suitable inert solvent such as dichloromethane, acetonitrile, 1,4-dioxane, tetrahydrofuran or mixtures thereof, at room temperature for several hours.

The ureas XLVIII can be formed by treatment of the amines XLIII with the isocyanates XLVII. The reaction can be carried out in an organic solvent such as dichloromethane, acetonitrile or mixtures thereof, at room temperature for several hours.

Hydrolysis of the methyl ester moieties of the amides XLV, the sulfonamides and the ureas XLVIII affords the compounds of interest of formula Id, Ie and If separately. The reaction can be carried out in the presence of an aqueous inorganic base such as lithium hydroxide, sodium hydroxide, or potassium hydroxide in an inert solvent such as 1,4-dioxane, or tetrahydrofuran at room temperature for several hours.

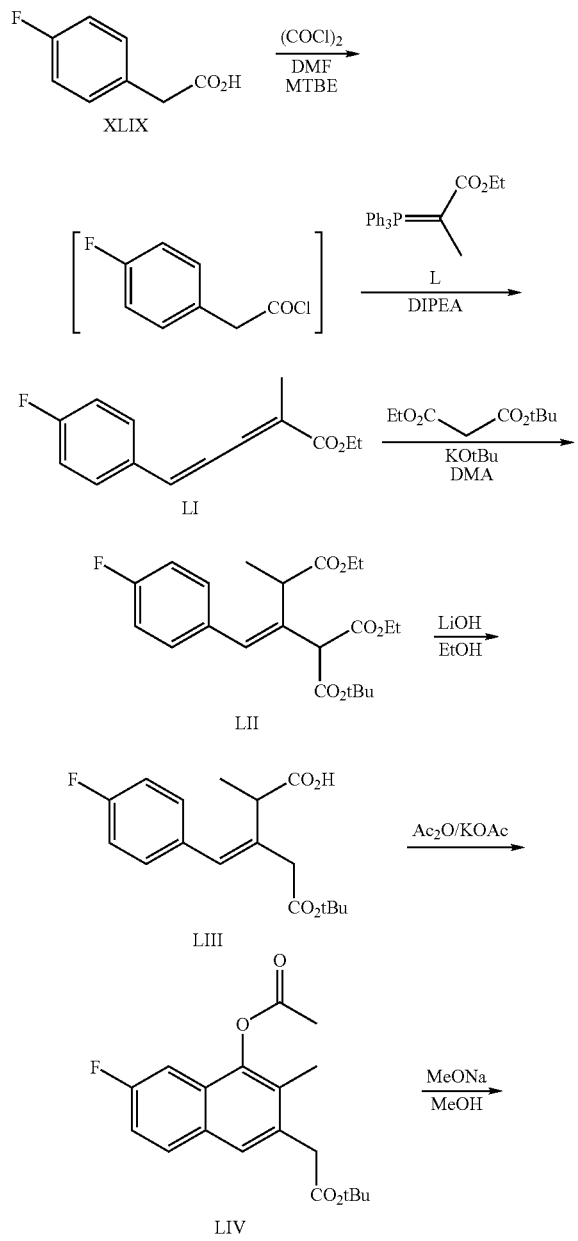

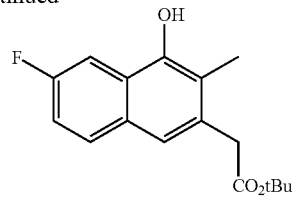
IIb-1

The key intermediate IIb-1 (which can be used as a replacement for intermediate II in scheme 5 to make the compounds of formula III) can be prepared as described in Scheme 9. Treatment of (4-fluoro-phenyl)-acetic acid (XLIX) with oxalyl chloride generates the corresponding acid chloride in situ, which is not isolated, but treated with the Wittig-type reagent L in the presence of a base to produce the allene derivative LI. A conjugate addition reaction of the allene with malonic acid tert-butyl ester ethyl ester produces the tri-ester derivative LII, which upon hydrolysis and subsequent decarboxylation generates the acid derivative LIII. Acetic anhydride-promoted cyclization of LIII furnishes the naphthalene derivative LIV, which upon hydrolysis of the acetyl group produces the key intermediate IIb-1.

The conversion of (4-fluorophenyl)-acetic acid to its corresponding acid chloride derivatives can be accomplished by methods known in the art. For example, the reaction can be carried out with oxalyl chloride and a catalytic amount of N,N-dimethylformamide (DMF), in an ether solvent, at room temperature. Subsequent treatment of the in situ generated acid chloride with a base such as N,N-diisopropylethylamine will lead to the generation of the corresponding ketene, which upon treatment with a Wittig type reagent such as L in an ether solvent at a temperature between 0-10° C. produces the allene derivative LI.

The conjugate addition reaction between the allene derivative LI and malonic acid tert-butyl ester ethyl ester to produce the tri-ester derivative LII is conducted in the presence of a base such as potassium tert-butoxide, in a solvent such as N,N-dimethyl acetamide at room temperature.

The ester hydrolysis of the two ethyl esters in LII can be accomplished using methods known in the art. For example, the reaction can be conducted using an aqueous base such as lithium hydroxide, in the presence of a solvent such as ethanol, at room temperature overnight. The subsequent decarboxylation reaction can then be carried out by heating the solution of the resulting diacid at reflux for several hours, to produce LIII.

The cyclization of the unsaturated acid derivative LIII to the naphthalene LIV is accomplished as previously described (similar to Scheme 2), in the presence of acetic anhydride and potassium acetate or sodium acetate, at a temperature of about 85° C., for several hours.

The acetate derivative LIV then undergoes a hydrolysis, upon treatment with a base such as sodium methoxide, in a solvent such as methanol, at room temperature, to produce the desired key intermediate IIb-1.

EXAMPLES

Materials and Instrumentation

Intermediates and final compounds were purified by either flash chromatography and/or preparative HPLC (high performance liquid chromatography). Flash chromatography was performed using (1) the Biotage SP1™ system and the Quad 12/25 Cartridge module from Biotage AB) or (2) the ISCO CombiFlash® chromatography instrument (from Teledyne Isco, Inc.); unless otherwise noted. The silica gel brand and pore size utilized were: (1) KP-SIL™ 60 Å, particle size: 40-60 micron (from Biotage AB); (2) Silica Gel CAS registry No: 63231-67-4, particle size: 47-60 micron; or (3) ZCX from Qingdao Haiyang Chemical Co., Ltd, pore size: 200-300 mesh or 300-400 mesh. Preparative HPLC was performed on a reversed phase column using an Xbridge™ Prep $C_{18}$ (5 μm, OBD™ 30×100 mm) column (from Waters Corporation), or a SunFire™ Prep $C_{18}$ (5 μm, OBD™ 30×100 mm) column (from Waters Corporation).

Mass spectrometry (MS) was performed using a Waters® Alliance® 2795-ZQ™ 2000 (from Waters Corporation. Mass spectra data generally only indicates the parent ions unless otherwise stated. MS data is provided for a particular intermediate or compound where indicated.

Nuclear magnetic resonance spectroscopy (NMR) was performed using a Bruker Avance 400 MHZ Digital NMR Spectrometer (for the HNMR spectrum acquired at 400 MHz) (from Bruker BioSpin). NMR data is provided for a particular intermediate or compound where indicated.

The microwave assisted reactions were carried out in a Biotage Initiator™ Sixty (from Biotage AB).

All reactions involving air-sensitive reagents were performed under an inert atmosphere. Reagents were used as received from commercial suppliers unless otherwise noted.

Part I: Preparation of Preferred Intermediates

Preparation of
(6-fluoro-4-hydroxy-naphthalen-2-yl)-acetic acid methyl ester

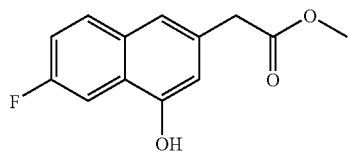

2-(4-Fluoro-benzylidene)-succinic acid 1-methyl ester

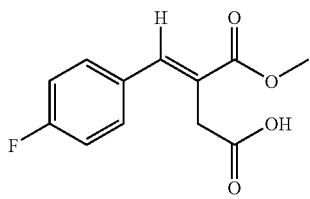

To a refluxing mixture of potassium tert-butoxide (27 g, 242 mmol) and tert-butanol (150 mL) was added a solution of 4-fluoro-benzaldehyde (20 g, 161 mmol) and dimethyl succinate (28 g, 193.2 mmol) in tert-butanol (100 mL) dropwise. After being stirred at reflux for 3 hours, the mixture was concentrated in vacuo to remove tert-butanol. The residue was dissolved in 1 N hydrochloric acid (180 mL). The resulting aqueous solution was extracted with ethyl acetate (100 mL×3). The combined organic layers were dried over sodium sulfate, filtered, and concentrated in vacuo. The residue was purified by column chromatography (elution with 30% ethyl acetate in petroleum ether) to afford 2-(4-fluoro-benzylidene)-succinic acid 1-methyl ester (25.5 g, 66%) as a light yellow solid. $^1$H NMR (400 MHz, CD$_3$OD) δ ppm 7.84 (s, 1H), 7.41-7.46 (m, 2H), 7.13-7.20 (m, 2H), 3.81 (s, 3H), 3.49 (s, 2H).

4-Acetoxy-6-fluoro-naphthalene-2-carboxylic acid methyl ester

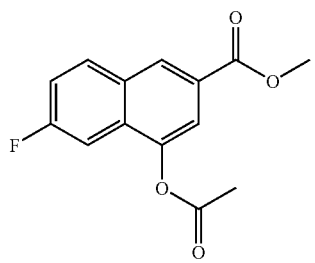

To a stirred solution of 2-(4-fluoro-benzylidene)-succinic acid 1-methyl ester (2 g, 8.4 mmol) in acetic anhydride (10 mL) was added sodium acetate (0.83 g, 10.1 mmol). After being heated at reflux for 6 hours, the mixture was concentrated in vacuo. The residue was dissolved in 1 N hydrochloric acid (20 mL). The aqueous solution was extracted with ethyl acetate (15 mL×3). The combined organic layers were dried over sodium sulfate, filtered, and concentrated in vacuo. The residue was purified by column chromatography (gradient elution with 10-20% ethyl acetate in petroleum ether) to afford 4-acetoxy-6-fluoro-naphthalene-2-carboxylic acid methyl ester (1.1 g, 50%) as a white solid. $^1$H NMR (400 MHz, CDCl$_3$) δ ppm 8.52 (s, 1H), 8.00 (dd, J=9.09, 5.56 Hz, 1H), 7.89 (s, 1H), 7.50 (dd, J=9.85, 2.53 Hz, 1H), 7.37 (td, J=8.59, 2.53 Hz, 1H), 3.99 (s, 3H), 2.49 (s, 3H).

6-Fluoro-4-hydroxy-naphthalene-2-carboxylic acid methyl ester

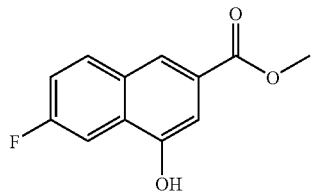

To a solution of 4-acetoxy-6-fluoro-naphthalene-2-carboxylic acid methyl ester (1 g, 3.8 mmol) in methanol (20 mL) was added sodium methoxide (309 mg, 5.7 mmol). After being stirred at room temperature for 1 hour, the reaction mixture was acidified to pH 3 with 1N hydrochloric acid. The resulting precipitate was collected by filtration and dissolved in ethyl acetate. The organic solution was dried over sodium sulfate, and concentrated in vacuo to afford 900 mg of crude 6-fluoro-4-hydroxy-naphthalene-2-carboxylic acid methyl ester as a pale yellow solid, which was used in the next step without further purification.

4-Benzyloxy-6-fluoro-naphthalene-2-carboxylic acid methyl ester

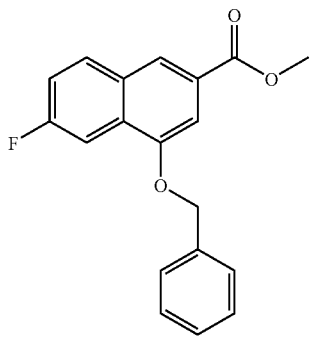

To a mixture of 6-fluoro-4-hydroxy-naphthalene-2-carboxylic acid methyl ester (4.6 g, 21 mmol) and potassium carbonate (5.8 g, 42 mmol), was added benzyl bromide (5.47 mL, 32 mmol) in acetone (100 mL). After being stirred vigorously at reflux for 4 hours under a nitrogen atmosphere, the resulting mixture was cooled to room temperature, filtered, and concentrated in vacuo to give 4-benzyloxy-6-fluoro-naphthalene-2-carboxylic acid methyl ester (5.85 g, 90%) as a white solid.

(4-Benzyloxy-6-fluoro-naphthalen-2-yl)-methanol

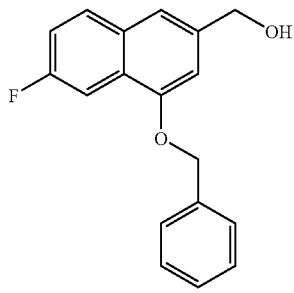

To a slurry of lithium aluminum hydride (1.4 g, 37.4 mmol) in tetrahydrofuran (30 mL) was added a solution of 4-benzyloxy-6-fluoro-naphthalene-2-carboxylic acid methyl ester (5.8 g, 18.7 mmol) in tetrahydrofuran (30 mL) at 0° C. under a nitrogen atmosphere. After being heated at 60° C. for 1 hour under a nitrogen atmosphere, the resulting mixture was cooled to 0° C. and treated with 1 N hydrochloric acid to quench the reaction. The mixture was extracted with diethyl ether (50 mL×4). The combined organic layers were dried over sodium sulfate, filtered, and concentrated in vacuo to give (4-benzyloxy-6-fluoro-naphthalen-2-yl)-methanol (4.9 g, 93%) as a white solid.

1-Benzyloxy-3-chloromethyl-7-fluoro-naphthalene

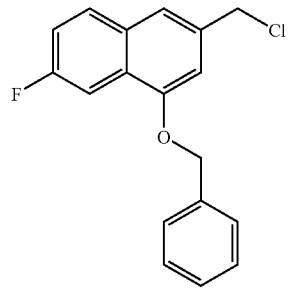

To a solution of triphenylphosphine (2.8 g, 10.6 mmol) in anhydrous tetrahydrofuran (16 mL) was added carbon tetrachloride (5 mL). After the mixture was stirred at room temperature for 10 minutes, (4-benzyloxy-6-fluoro-naphthalen-2-yl)-methanol (1.5 g, 5.3 mmol) was added as a solid under a nitrogen atmosphere. After being stirred at reflux for 2 hours, the resulting mixture was cooled to room temperature, diluted with water, and extracted with ethyl acetate (100 mL). The organic layer was washed with water (50 mL×2). The combined aqueous layers were extracted with ethyl acetate (100 mL). The combined organic layers were dried over sodium sulfate, filtered, and concentrated in vacuo. The residue was purified by column chromatography (elution with 5% ethyl acetate in petroleum ether) to afford 1-benzyloxy-3-chloromethyl-7-fluoro-naphthalene (1.4 g, 87.5%) as a white solid.

(4-Benzyloxy-6-fluoro-naphthalen-2-yl)-acetic acid methyl ester

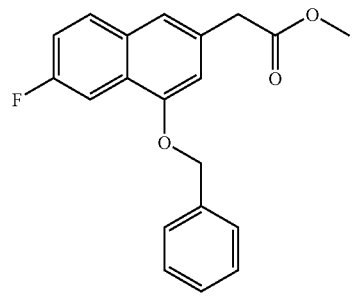

A flask containing 1-benzyloxy-3-chloromethyl-7-fluoro-naphthalene (5.4 g, 18 mmol), bis(triphenylphosphine)dichloropalladium(II) (630 mg, 0.9 mmol) and potassium carbonate (2.6 g, 18.9 mmol) was evacuated and then filled with carbon monoxide (balloon). Methanol (25 mL) and tetrahydrofuran (50 mL) were added by means of a syringe. After being stirred at room temperature under a carbon monoxide atmosphere (balloon) overnight, the reaction mixture was diluted with water (100 mL), and extracted with ethyl acetate (100 mL). The organic layer was washed with water (50 mL×2). The combined aqueous layers were extracted with ethyl acetate (150 mL), and the combined organic layers were dried over sodium sulfate, filtered, and concentrated in vacuo. The residue was purified by column chromatography (elution with 20% ethyl acetate in petroleum ether) to afford (4-benzyloxy-6-fluoro-naphthalen-2-yl)-acetic acid methyl ester (5.3 g, 91%) as a white solid.

(6-Fluoro-4-hydroxy-naphthalen-2-yl)-acetic acid methyl ester

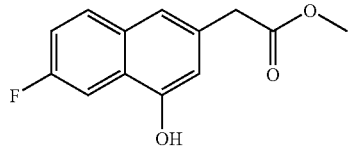

To a solution of (4-benzyloxy-6-fluoro-naphthalen-2-yl)-acetic acid methyl ester (876 mg, 2.7 mmol) in methanol (20 mL) was added 10% palladium on carbon (132 mg). The resulting mixture was stirred vigorously under a hydrogen (balloon) atmosphere overnight and then filtered. The filtrate was concentrated in vacuo to give (6-fluoro-4-hydroxy-naphthalen-2-yl)-acetic acid methyl ester (601 mg, 95%) as a white solid. $^1$H NMR (400 MHz, CDCl$_3$) δ ppm 7.69-7.76 (m, 2H), 7.30 (s, 1H), 7.22-7.26 (m, 1H), 6.82 (s, 1H), 3.74 (s, 3H), 3.72 (s, 2H).

Preparation of (6-fluoro-4-hydroxy-3-methyl-naphthalen-2-yl)-acetic acid methyl ester

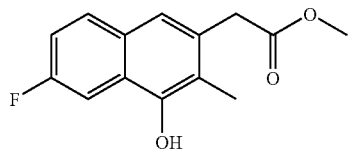

2-(4-Fluoro-benzylidene)-3-methyl-succinic acid 1-methyl ester

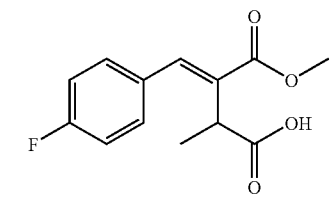

After the careful addition of absolute methanol (0.1 mL) to a suspension of sodium hydride (20 g, 0.5 mol, 60% in mineral oil) in anhydrous toluene (200 mL), a solution of 4-fluoro-benzaldehyde (31 g, 0.25 mol) and dimethyl 2-methyl-succinate (60 g, 0.38 mol) in anhydrous toluene (100 mL) was added at room temperature under a stream of nitrogen. The resulting mixture was stirred at room temperature for 30 minutes and then quenched by the slow addition of water (20 mL). The mixture was acidified to pH 3 by the addition of concentrated hydrochloric acid, and extracted with ethyl acetate (200 mL×3). The combined organic layers were dried over sodium sulfate, filtered, and concentrated in vacuo. The residue was purified by column chromatography (elution with 30% ethyl acetate in petroleum ether) to afford 2-(4-fluoro-benzylidene)-3-methyl-succinic acid 1-methyl ester (20 g, 33%) as a white solid. $^1$H NMR (400 MHz, acetone-d$_6$) δ ppm 7.77 (s, 1H), 7.54 (d, J=8.8 Hz, 2H), 7.25 (d, J=8.8 Hz, 2H), 3.82 (q, 7.2 Hz, 1H), 1.40 (d, J=6.8 Hz, 3H).

6-Fluoro-4-hydroxy-3-methyl-naphthalene-2-carboxylic acid methyl ester

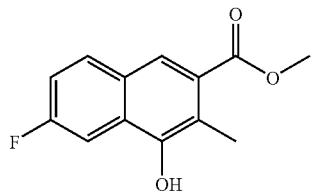

To a solution of 2-(4-fluoro-benzylidene)-3-methyl-succinic acid 1-methyl ester (1 g, 4 mmol) in anhydrous tetrahydrofuran (10 mL), trifluoroacetic anhydride (3.3 g, 15.7 mmol) was added in one portion followed by the addition of triethylamine (3.3 ml, 24 mmol) dropwise. After being stirred at room temperature for 4 hours, the mixture was acidified to pH 3 with 5% aqueous hydrochloric acid and extracted with ethyl acetate (20 mL). The organic layer was concentrated in vacuo. The residue was dissolved in methanol (15 mL). The resulting solution was cooled to 0° C., then treated with sodium borohydride (380 mg, 10 mmol), and stirred for 1 hour. The reaction mixture was diluted with ethyl acetate (20 mL) and 5% aqueous hydrochloric acid (20 mL). The aqueous phase was separated and extracted with ethyl acetate (15 mL×3). The combined organic layers were washed with brine (40 mL), dried over sodium sulfate, filtered, and concentrated in vacuo. The residue was purified by column chromatography (elution with 10% ethyl acetate in hexanes) to afford 6-fluoro-4-hydroxy-3-methyl-naphthalene-2-carboxylic acid methyl ester (740 mg, 80%) as a pale solid.

Alternatively, Starting with 2-(4-fluoro-benzylidene)-3-methyl-succinic acid 1-methyl ester, using a method analogous to the one described above for 6-fluoro-4-hydroxy-naphthalene-2-carboxylic acid methyl ester, 6-fluoro-4-hydroxy-3-methyl-naphthalene-2-carboxylic acid methyl ester was obtained as a pale solid.

4-Benzyloxy-6-fluoro-3-methyl-naphthalene-2-carboxylic acid methyl ester

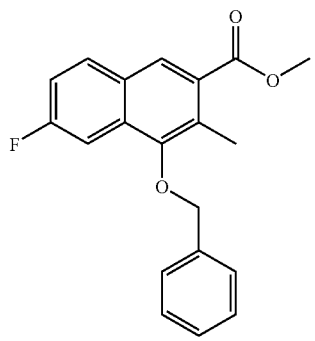

To a mixture of 6-fluoro-4-hydroxy-3-methyl-naphthalene-2-carboxylic acid methyl ester (8.0 g, 34.2 mmol) and potassium carbonate (9.45 g, 68.4 mmol) was added benzyl bromide (4.5 mL, 37.6 mmol) in acetone (100 mL). The resulting mixture was vigorously stirred at reflux for 10 hours under a nitrogen atmosphere. The mixture was cooled, then filtered, and concentrated in vacuo to give 4-benzyloxy-6-fluoro-3-methyl-naphthalene-2-carboxylic acid methyl ester (10.4 g, 94%) as a white solid.

(4-Benzyloxy-6-fluoro-3-methyl-naphthalen-2-yl)-methanol

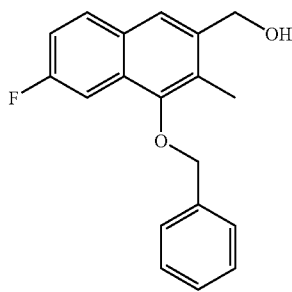

To a slurry of lithium aluminum hydride (1.8 g, 47.5 mmol) in tetrahydrofuran (50 mL) was added a solution of 4-benzyloxy-6-fluoro-3-methyl-naphthalene-2-carboxylic acid methyl ester (10 g, 30.8 mmol) in tetrahydrofuran (50 mL) at 0° C. under a nitrogen atmosphere. After being heated at 60° C. for 2 hours, the resulting mixture was cooled to 0° C. and treated with 1 N hydrochloric acid to quench the reaction. The aqueous layer was extracted with diethyl ether (100 mL×5). The combined organic layers were dried over sodium sulfate, filtered, and concentrated in vacuo to give (4-benzyloxy-6-fluoro-3-methyl-naphthalen-2-yl)-methanol (8.4 g, 92%) as a white solid. $^1$H NMR (400 MHz, CDCl$_3$) δ ppm 7.84 (dd, J=5.6, 9.2 Hz, 1H), 7.70 (dd, J=2.4, 10.0 Hz, 1H), 7.69 (s, 1H), 7.40-7.50 (m, 5H), 7.24 (td, J=2.4, 8.4 Hz, 1H), 4.99 (s, 2H), 4.87 (s, 2H), 2.47 (s, 3H).

1-Benzyloxy-3-chloromethyl-7-fluoro-2-methyl-naphthalene

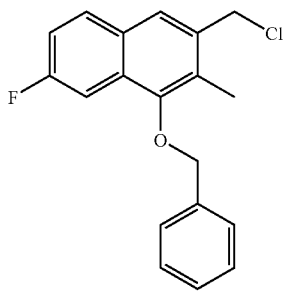

To a solution of triphenylphosphine (7.1 g, 27.2 mmol) in anhydrous tetrahydrofuran (32 mL) was added carbon tetrachloride (10 mL). The mixture was stirred for 10 minutes and 4-benzyloxy-6-fluoro-3-methyl-naphthalen-2-yl)-methanol (4 g, 13.6 mmol) was introduced as a solid under a nitrogen atmosphere. After being stirred at reflux for 2 hours, the resulting mixture was diluted with water, and extracted with ethyl acetate (150 mL). The organic layer was washed with water (50 mL×2). The combined aqueous layers were extracted with ethyl acetate (150 mL), and the combined organic layers were dried over sodium sulfate, filtered, and concentrated in vacuo. The residue was purified by column chromatography (elution with 5% ethyl acetate in petroleum ether) to afford 1-benzyloxy-3-chloromethyl-7-fluoro-2-methyl-naphthalene (3.5 g, 83%) as a white solid. $^1$H NMR (400 MHz, CDCl$_3$) δ ppm 7.83 (dd, J=5.6, 9.3 Hz, 1H), 7.71 (d, J=2.4 Hz, 1H), 7.68 (s, 1H), 7.40-7.58 (m, 5H), 7.25 (td, J=2.4, 8.8 Hz, 1H), 5.01 (s, 2H), 4.79 (s, 2H), 2.54 (s, 3H); MS cald. for C$_{19}$H$_{16}$ClFO 314, obsd. (ESI$^+$) [(M+H)$^+$] 315.

(4-Benzyloxy-6-fluoro-3-methyl-naphthalen-2-yl)-acetic acid methyl ester

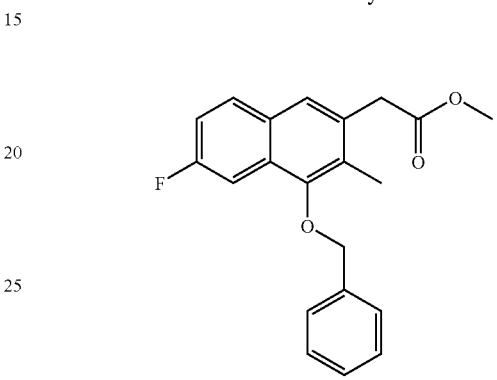

A flask containing 1-benzyloxy-3-chloromethyl-7-fluoro-2-methyl-naphthalene (3.3 g, 10.4 mmol), bis(triphenylphosphine)dichloropalladium(II) (360 mg, 0.5 mmol) and potassium carbonate (1.52 g, 11.0 mmol) was evacuated and then filled with carbon monoxide (balloon). Methanol (18 mL) and tetrahydrofuran (35 mL) were added by means of a syringe. After being stirred at room temperature under a carbon monoxide atmosphere (balloon) overnight, the resulting mixture was diluted with water (50 mL), and extracted with ethyl acetate (100 mL). The organic layer was washed with water (50 mL×2). The combined aqueous layers were extracted with ethyl acetate (150 mL) and the combined organic layers were dried over sodium sulfate, filtered, and concentrated in vacuo. The residue was purified by column chromatography (elution with 20% ethyl acetate in petroleum ether) to afford (4-benzyloxy-6-fluoro-3-methyl-naphthalen-2-yl)-acetic acid methyl ester (3.4 g, 97%) as a white solid. $^1$H NMR (400 MHz, CDCl$_3$) δ ppm 7.80 (dd, J=5.2, 8.4 Hz, 1H), 7.70 (d, J=10.4 Hz, 1H), 7.40-7.59 (m, 6H), 7.25 (td, J=2.0, 8.8 Hz, 1H), 5.00 (s, 2H), 3.84 (s, 2H), 3.75 (s, 3H), 2.42 (s, 3H); MS cald. for C$_{21}$H$_{19}$FO$_3$ 338, obsd. (ESI$^+$) [(M+H)$^+$] 339.

(6-Fluoro-4-hydroxy-3-methyl-naphthalen-2-yl)-acetic acid methyl ester

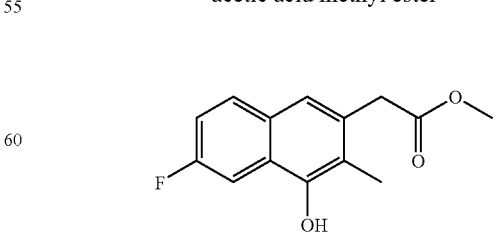

To a solution of (4-benzyloxy-6-fluoro-3-methyl-naphthalen-2-yl)-acetic acid methyl ester (3.4 g, 10.0 mmol) in methanol (50 mL) was added 10% palladium on carbon (0.5 g). The resulting mixture was vigorously stirred under a hydrogen (balloon) atmosphere overnight, and then filtered. The filtrate was concentrated in vacuo to give (6-fluoro-4-hydroxy-3-methyl-naphthalen-2-yl)-acetic acid methyl ester (2.44 g, 98%) as a white solid. $^1$H NMR (400 MHz, CDCl$_3$) δ ppm 7.69-7.74 (m, 2H), 7.34 (s, 1H), 7.21 (td, J=2.4, 8.4 Hz, 1H), 5.16 (s, 1H), 3.82 (s, 2H), 3.74 (s, 3H), 2.35 (s, 3H); MS cald. for C$_{14}$H$_{13}$FO$_3$ 248, obsd. (ESI$^+$) [(M+H)$^+$] 249.

Preparation of 7-fluoro-3-methoxycarbonylmethyl-2-methyl-naphthalene-1-carboxylic acid

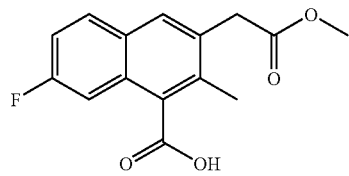

(6-Fluoro-3-methyl-4-trifluoromethanesulfonyloxy-naphthalen-2-yl)-acetic acid methyl ester

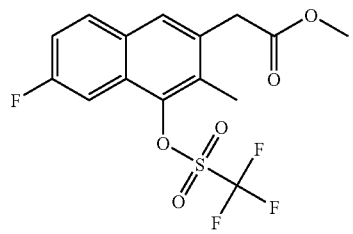

To a cooled (ice-water bath) solution of 6-fluoro-4-hydroxy-3-methyl-naphthalen-2-yl)-acetic acid methyl ester (1.16 g, 4.7 mmol) and pyridine (1.86 mL, 23 mmol) in anhydrous dichloromethane was added trifluoromethanesulfonic anhydride (929 µL, 5.5 mmol) dropwise slowly to maintain the temperature below 5° C. After being stirred at 0° C. for 2 hours, the resulting mixture was concentrated in vacuo to remove the solvent. The residue was dissolved in ethyl acetate (20 mL). The resulting solution was washed with 1N hydrochloric acid (10 mL×2), dried over sodium sulfate, filtered, and concentrated in vacuo. The residue was purified by column chromatography (elution with 20% ethyl acetate in petroleum ether) to afford (6-fluoro-3-methyl-4-trifluoromethanesulfonyloxy-naphthalen-2-yl)-acetic acid methyl ester (1.60 g, 89.5%) as a white solid.

7-Fluoro-3-methoxycarbonylmethyl-2-methyl-naphthalene-1-carboxylic acid

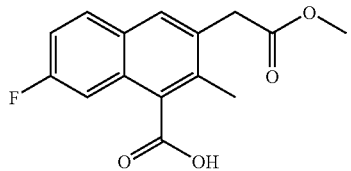

A parr bottle containing (6-fluoro-3-methyl-4-trifluoromethanesulfonyloxy-naphthalen-2-yl)-acetic acid methyl ester (1.0 g, 2.63 mmol), 1,1'-bis(diphenylphosphino)ferrocene (148 mg, 0.27 mmol), and palladium(II) acetate (60 mg, 0.27 mmol) was evacuated and then filled with carbon monoxide. N,N-dimethylformamide (60 mL), water (40 mL) and triethylamine were added by means of a syringe. The reaction mixture was shaken at 60° C. under a carbon monoxide atmosphere (30 psi) for 4 hours. The resulting mixture was diluted with ethyl acetate (60 mL), and then extracted with a saturated aqueous solution of sodium carbonate (50 mL×3). The combined aqueous layers were acidified to pH 3 by the slow addition of 12 N hydrochloric acid in an ice-water bath, and extracted with ethyl acetate (80 mL×3). The combined organic layers were washed with brine (150 mL×2), dried over sodium sulfate, filtered, and concentrated in vacuo to afford 7-fluoro-3-methoxycarbonylmethyl-2-methyl-naphthalene-1-carboxylic acid (680 mg, 94%) as a light brown viscous oil. MS cald. for C$_{15}$H$_{13}$FO$_4$ 276, obsd. (ESI$^+$) [(M+H)$^+$] 277.

Preparation of 7-fluoro-3-methoxycarbonylmethyl-naphthalene-1-carboxylic acid

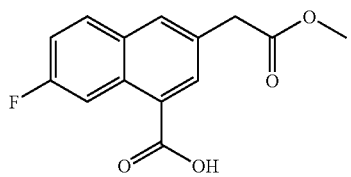

Starting with (6-fluoro-4-hydroxy-naphthalen-2-yl)-acetic acid methyl ester, using the method analogous to the one described for 7-fluoro-3-methoxycarbonylmethyl-2-methyl-naphthalene-1-carboxylic acid, 7-fluoro-3-methoxycarbonylmethyl-naphthalene-1-carboxylic acid (80 mg) was obtained as a light brown viscous oil. MS cald. for C$_{14}$H$_{10}$FO$_4$ 262, obsd. (ESI$^+$) [(M+H)$^+$] 263.

Preparation of 2,6-diaza-spiro[3.3]heptane-2-carboxylic acid tert-butyl ester

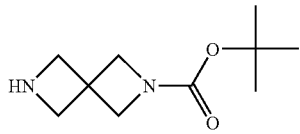

2,6-Bis-(1-phenyl-ethyl)-2,6-diaza-spiro[3.3]heptane dihydrochloride

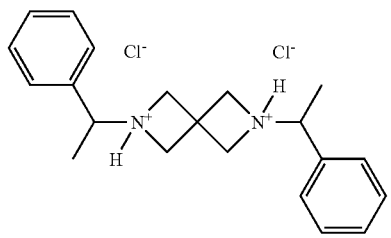

To a solution of 2,2-bis-hydroxymethyl-propane-1,3-diol (40.86 g, 0.3 mol) in anhydrous acetonitrile, which was cooled to −20° C., was slowly added trifluoromethanesulfonic anhydride (212 mL, 1.25 mol) dropwise followed by the dropwise addition of N,N-diisopropylethylamine (267.5 mL, 1.54 mol). Both of the reagents were added at such a rate as to maintain the internal temperature below −10° C. After the mixture was stirred for 30 minutes at a temperature between −20° C. and −10° C., another portion of N,N-diisopropylethylamine (267.5 mL, 1.54 mol) was added, followed by the dropwise addition of 1-phenyl-ethylamine (76.5 mL, 0.60 mol). Both of the reagents were added at such a rate as to maintain the internal temperature below −10° C. The resulting mixture was heated at 70° C. for 2 hours, and then concentrated in vacuo to remove the solvent. The residue was dissolved in ethyl acetate (500 mL), and the solution was washed with brine (500 mL×2), dried over sodium sulfate, filtered, and concentrated in vacuo. The residue was purified by column chromatography (gradient elution with 5% to 10% methanol in dichloromethane) to afford a light brown viscous oil, which was subsequently dissolved in a solution of hydrogen chloride in methanol (150 mL, 4 M) and the solution was concentrated in vacuo. The residue was stirred with dichloromethane (20 mL) and petroleum ether (100 mL), then filtered, and the collected solid was dried in vacuo to afford 2,6-bis-(1-phenyl-ethyl)-2,6-diaza-spiro[3.3]heptane dihydrochloride (43.6 g, 38.2%) as a light brown solid. MS calcd. for $C_{21}H_{26}N_2$ 306, obsd. (ESI$^+$) [(M+H)$^+$] 307.

2-(1-Phenyl-ethyl)-2,6-diaza-spiro[3.3]heptane dihydrochloride

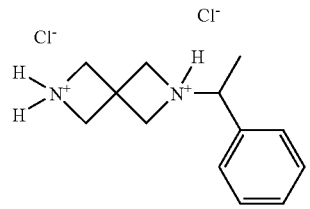

A flask containing a mixture of 2,6-bis-(1-phenyl-ethyl)-2,6-diaza-spiro[3.3]heptane dihydrochloride (900 mg, 2.4 mmol), ammonium formate (7.2 g, 114 mmol), 10% palladium on carbon (180 mg) and methanol (30 mL) was evacuated and filled with argon. The resulting mixture was stirred at 65° C. until the ratio of the amount of the starting material to the amount of the desired product was unchanged by monitoring with TLC and HPLC. The resulting mixture was filtered and concentrated in vacuo to afford a mixture of 2-(1-phenyl-ethyl)-2,6-diaza-spiro[3.3]heptane dihydrochloride and 2,6-bis-(1-phenyl-ethyl)-2,6-diaza-spiro[3.3]heptane dihydrochloride (750 mg) as a light brown solid, which was used for the next step without any purification. MS cald. for $C_{13}H_{18}N_2$ 202, obsd. (ESI$^+$) [(M+H)$^+$] 203.

6-(1-Phenyl-ethyl)-2,6-diaza-spiro[3.3]heptane-2-carboxylic acid tert-butyl ester

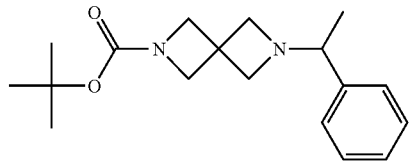

To a mixture of 2-(1-phenyl-ethyl)-2,6-diaza-spiro[3.3]heptane dihydrochloride and 2,6-bis-(1-phenyl-ethyl)-2,6-diaza-spiro[3.3]heptane dihydrochloride (700 mg) in 1,4-dioxane (6 mL) and water (6 mL) was added di-tert-butyl dicarbonate (600 mg, 2.75 mmol) and sodium bicarbonate (700 mg, 8.3 mmol). After being stirred at room temperature overnight, the resulting mixture was concentrated in vacuo to remove the organic solvent, and extracted with dichloromethane (10 mL×3). The combined organic layers were dried over sodium sulfate, filtered, and concentrated in vacuo. The residue was purified by column chromatography (gradient elution with 5% to 10% methanol in dichloromethane) to afford 6-(1-phenyl-ethyl)-2,6-diaza-spiro[3.3]heptane-2-carboxylic acid tert-butyl ester (238 mg, 33%) as a viscous oil and 2,6-bis-(1-phenyl-ethyl)-2,6-diaza-spiro[3.3]heptane (250 mg) as a viscous oil.

2,6-Diaza-spiro[3.3]heptane-2-carboxylic acid tert-butyl ester

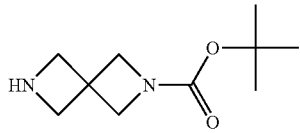

A flask containing 6-(1-phenyl-ethyl)-2,6-diaza-spiro[3.3]heptane-2-carboxylic acid tert-butyl ester (200 mg, 0.66 mmol), ammonium formate (4.22 g, 67 mmol), 10% palladium on carbon (40 mg) and methanol (10 mL) was evacuated and filled with argon. The resulting mixture was stirred at 65° C. for 3 hours, then filtered and concentrated in vacuo to afford 2,6-diaza-spiro[3.3]heptane-2-carboxylic acid tert-butyl ester (130 mg, 99%) as a brown viscous oil which was used for the next step without further purification.

Preparation of (6-fluoro-4-hydroxy-3-methyl-naphthalen-2-yl)-acetic acid tert-butyl ester

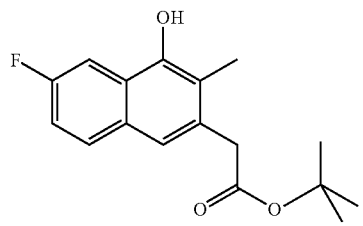

4-(4-Fluoro-phenyl)-2-methyl-buta-2,3-dienoic acid ethyl ester

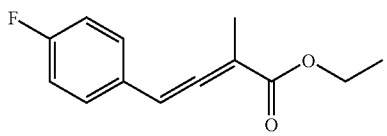

To a solution of (4-fluoro-phenyl)-acetic acid (22.33 g, 144.9 mmol) in 100 mL of methyl tert-butyl ether and 250 µL of DMF was added 13.02 mL (146.3 mmol) of oxalyl chloride at room temperature dropwise over 30 minutes. The resulting mixture was stirred at room temperature for an additional 20 minutes (HPLC indicated completed reaction), and then the entire solution was added dropwise over 1 hour to a solution of N,N-diisopropylethylamine (50.48 mL, 289.8 mmol) and ethyl 2-(triphenylphosphoranylidene)propionate (50.0 g, 138.0 mmol) in 100 mL of methyl tert-butyl ether, while maintaining the internal temperature between 0-15° C. After the addition was complete, the reaction mixture was stirred for an additional 10 minutes at 0-10° C., when HPLC indicated a completed reaction. The reaction mixture was then diluted with 100 mL of heptane, and stirred for 30 minutes at 0-10° C. The resulting solid was filtered and washed with 2×100 mL of 1:1 methyl tert-butyl ether:heptane. The filtrate and the washings were combined and washed with 100 mL of water, 100 mL of 1M citric acid, 2×100 mL of water, then concentrated azeotropically at 25° C./60 mmHg to a total volume of ~40 mL. The residue was diluted with 60 mL of methyl tert-butyl ether. This solution was then directly used for the next step.

2-Ethoxycarbonyl-3-[1-(4-fluoro-phenyl)-meth-(E)-ylidene]-4-methyl-pentanedioic acid 1-tert-butyl ester 5-ethyl ester

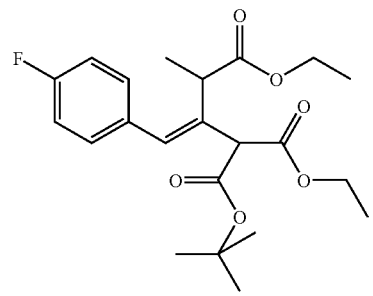

Malonic acid tert-butyl ester ethyl ester (30.08 g, 151.8 mmol) was added to a solution of potassium tert-butoxide (16.30 g, 138.0 mmol) in 200 mL of N,N-dimethyl acetamide, while the reaction temperature was maintained at ~25° C. To the resulting mixture was then added the solution of 4-(4-fluoro-phenyl)-2-methyl-buta-2,3-dienoic acid ethyl ester prepared above, at such a rate that the reaction temperature was maintained between 20-28° C. After the addition was complete, the reaction mixture was stirred at room temperature for 20 minutes, when HPLC indicated completed reaction. The mixture was then treated with 100 mL of 1M citric acid and 150 mL of ice-water, and then extracted with 400 mL of methyl tert-butyl ether. The organic extract was separated and washed with 2×200 mL of water, and then concentrated to produce 56.36 g of a yellow oil, which was used in the next step without further purification.

3-[1-(4-Fluoro-phenyl)-meth-(Z)-ylidene]-2-methyl-pentanedioic acid 5-tert-butyl ester

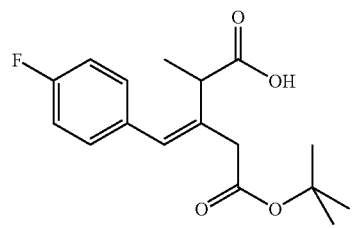

The malonate ester derivative prepared above (56.36 g, 138 mmol) was dissolved in 280 mL of absolute ethanol. Lithium hydroxide (1M solution, 414.0 mL, 414.0 mmol) was added slowly over 15 minutes, and the resulting reaction mixture was stirred at room temperature overnight. The solution was then heated at reflux for 3 hours (HPLC analysis indicated completed decarboxylation). At this time, the solution was concentrated at 30° C./30 mmHg to remove ~350 mL of solvent. The residue was cooled to 10° C., and treated with concentrated hydrochloric acid (32.0 mL, 389.7 mmol) dropwise, in order to adjust the pH to 2.75. The reaction mixture was then extracted with methyl tert-butyl ether (400 mL). The organic phase was separated and washed with 200 mL of water, then treated with 17.00 mL of 1M sodium carbonate in 150 mL of water, washed with an additional 200 mL of water, and then concentrated azeotropically at 30° C./80 mmHg to produce an oil. Methyl tert-butyl ether (200 mL) was added, and the residue was concentrated azeotropically at 30° C./80 mmHg to produce 38.3 g of a yellow oil, which was used in the next step without further purification.

(4-Acetoxy-6-fluoro-3-methyl-naphthalen-2-yl)-acetic acid tert-butyl ester

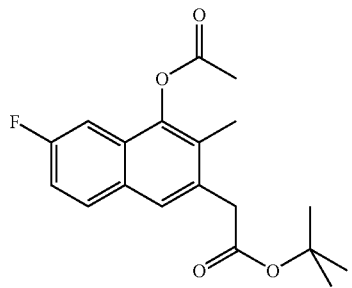

The above prepared 3-[1-(4-fluoro-phenyl)-meth-(Z)-ylidene]-2-methyl-pentanedioic acid 5-tert-butyl ester (38.3 g, 124.2 mmol) was dissolved in acetic anhydride (96.00 mL, 995.3 mmol). To this solution was added potassium acetate (18.66 g, 186.3 mmol), and the reaction mixture was stirred at 85±2° C. for 10 hours, when HPLC analysis showed completed reaction. The reaction mixture was then cooled to room temperature and diluted with 96 mL of heptane. To this solution, 270 mL of water was added over 1 hour, while maintaining the internal temperature at ~23° C. The mixture was then cooled to 0-5° C., and stirred for 2 hours. The solid formed was filtered, and then washed with water (2×40 mL), heptane (2×40 mL), and then dried under vacuum to furnish 28.5 g of a yellow solid, which was used in the next step without further purification.

(6-Fluoro-4-hydroxy-3-methyl-naphthalen-2-yl)-acetic acid tert-butyl ester

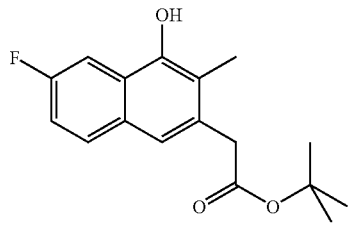

To a mixture of the above prepared (4-acetoxy-6-fluoro-3-methyl-naphthalen-2-yl)-acetic acid tert-butyl ester (28.4 g, 85.44 mmol) in 140 mL of methanol was added sodium methoxide (25% solution in methanol, 23.44 mL, 102.5 mmol) rapidly dropwise. The resulting reaction mixture was stirred at room temperature for 20 minutes, when HPLC analysis indicated a completed reaction. The mixture was cooled to 0° C., and then acidified to pH 2 with 1N hydrochloric acid solution (111.1 mL, 111.1 mmol). The mixture was then stirred at 0-5° C. for an additional 30 minutes. The resulting solid was filtered, and washed with water (2×40 mL), then dried under vacuum overnight (40° C.), to produce 23.7 g of a light yellow solid. $^1$H NMR (300 MHz, DMSO-$d_6$) δ ppm 9.09 (s, 1H), 7.76-7.86 (m, 2H), 7.26-7.35 (m, 2H), 3.71 (s, 2H), 2.23 (s, 3H), 1.41 (s, 9H).

Part II: Preparation of Compounds of Interest

Example 1-1

[4-(4-Ethanesulfonyl-piperazine-1-carbonyl)-6-fluoro-3-methyl-naphthalen-2-yl]-acetic acid

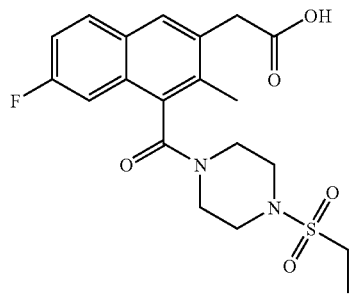

(4-Chlorocarbonyl-6-fluoro-3-methyl-naphthalen-2-yl)-acetic acid methyl ester

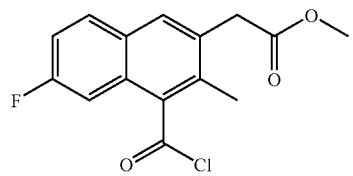

To a solution of 7-fluoro-3-methoxycarbonylmethyl-2-methyl-naphthalene-1-carboxylic acid (500 mg, 1.81 mmol) in anhydrous tetrahydrofuran (10 mL), was added oxalyl chloride (250 μL) and N,N-dimethylformamide (30 μL). The resulting mixture was stirred at 60° C. for 2 hours, and concentrated in vacuo to afford (4-chlorocarbonyl-6-fluoro-3-methyl-naphthalen-2-yl)-acetic acid methyl ester (526 mg, 99%) as a light yellow solid, which was used in the next step without further purification.

4-(7-Fluoro-3-methoxycarbonylmethyl-2-methyl-naphthalene-1-carbonyl)-piperazine-1-carboxylic acid tert-butyl ester

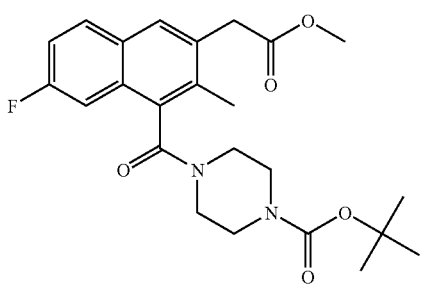

To a solution of (4-chlorocarbonyl-6-fluoro-3-methyl-naphthalen-2-yl)-acetic acid methyl ester (294 mg, 1.0 mmol) and piperazine-1-carboxylic acid tert-butyl ester (279 mg, 1.5 mmol) in dichloromethane was added triethylamine (458 µL, 3.3 mmol). The resulting mixture was stirred at room temperature overnight, and concentrated in vacuo. The residue was purified by column chromatography (gradient elution with 20-40% ethyl acetate in petroleum ether) to afford 4-(7-fluoro-3-methoxycarbonylmethyl-2-methyl-naphthalene-1-carbonyl)-piperazine-1-carboxylic acid tert-butyl ester (410 mg, 92%) as a white solid.

[6-Fluoro-3-methyl-4-(piperazine-1-carbonyl)-naphthalen-2-yl]-acetic acid methyl ester trifluoroacetate

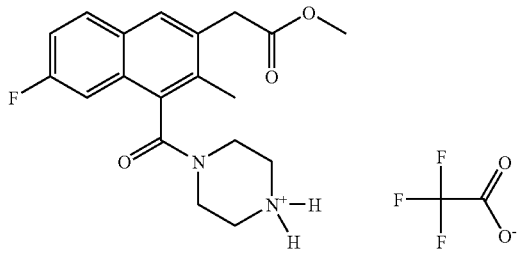

A solution of 4-(7-fluoro-3-methoxycarbonylmethyl-2-methyl-naphthalene-1-carbonyl)-piperazine-1-carboxylic acid tert-butyl ester (410 mg, 0.92 mmol) in dichloromethane (10 mL) was treated with trifluoroacetic acid (2.5 mL) at room temperature, and stirred for 4 hours. The resulting mixture was concentrated in vacuo to afford [6-fluoro-3-methyl-4-(piperazine-1-carbonyl)-naphthalen-2-yl]-acetic acid methyl ester trifluoroacetate as a viscous oil which was used in the next step without further purification.

[4-(4-Ethanesulfonyl-piperazine-1-carbonyl)-6-fluoro-3-methyl-naphthalen-2-yl]-acetic acid methyl ester

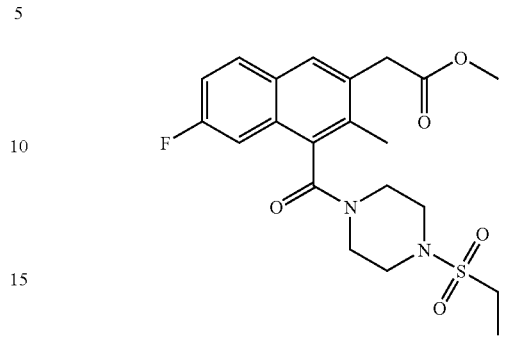

To a solution of [6-fluoro-3-methyl-4-(piperazine-1-carbonyl)-naphthalen-2-yl]-acetic acid methyl ester trifluoroacetate (45.8 mg, 0.10 mmol) and ethanesulfonyl chloride (14 µL, 0.15 mmol) in dichloromethane was added triethylamine (306 µL, 2.2 mmol). The resulting mixture was stirred at room temperature overnight, and concentrated in vacuo. The residue was purified by column chromatography (gradient elution with 20-40% ethyl acetate in petroleum ether) to afford [4-(4-ethanesulfonyl-piperazine-1-carbonyl)-6-fluoro-3-methyl-naphthalen-2-yl]-acetic acid methyl ester (38 mg, 87%) as a white solid.

[4-(4-Ethanesulfonyl-piperazine-1-carbonyl)-6-fluoro-3-methyl-naphthalen-2-yl]-acetic acid

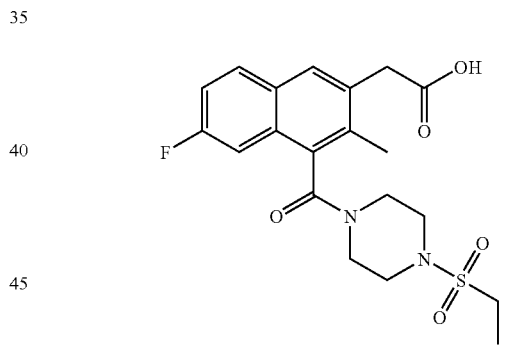

To a solution of [4-(4-ethanesulfonyl-piperazine-1-carbonyl)-6-fluoro-3-methyl-naphthalen-2-yl]-acetic acid methyl ester (36 mg, 0.08 mmol) in tetrahydrofuran (4 mL), was added 5N lithium hydroxide (6 mL). After being stirred at room temperature overnight, the resulting mixture was acidified to pH 3 with 5N hydrochloric acid, and extracted with ethyl acetate (10 mL×2). The organic layers were dried over sodium sulfate and concentrated in vacuo. The residue was purified by preparative HPLC (gradient elution with 30-50% 0.1% trifluoroacetic acid in water in acetonitrile, 8 minutes) to give [4-(4-ethanesulfonyl-piperazine-1-carbonyl)-6-fluoro-3-methyl-naphthalen-2-yl]-acetic acid (16 mg, 46%) as a white solid. $^1$H NMR (400 MHz, CD$_3$OD) δ ppm 7.95 (dd, J=8.97, 5.68 Hz, 1H), 7.87 (s, 1H), 7.26-7.38 (m, 2H), 3.95-4.16 (m, 2H), 3.90 (s, 2H), 3.48-3.55 (m, 2H), 3.20 (br. s, 6H), 2.41 (s, 3H), 1.34 (t, J,=,7.45 Hz, 3H); MS calcd. for C$_{20}$H$_{23}$FN$_2$O$_5$S 422, obsd. (ESI$^+$) [(M+H)$^+$] 423.

Examples 1-2 to 1-17

The following examples 1-2 to 1-19 were prepared in an analogous manner to example 1-1, starting with 4-fluoro-benzaldehyde, 4-fluoro-benzaldehyde, 4-trifluoromethyl-benzaldehyde and 4-trifluoromethoxy-benzaldehyde, to derive 7-fluoro-3-methoxycarbonylmethyl-naphthalene-1-carboxylic acid, 7-fluoro-3-methoxycarbonylmethyl-2-methyl-naphthalene-1-carboxylic acid, 3-methoxycarbonylmethyl-7-trifluoromethyl-naphthalene-1-carboxylic acid, or 3-methoxycarbonylmethyl-7-trifluoromethoxy-naphthalene-1-carboxylic acid respectively, which were then treated with piperazine-1-carboxylic acid tert-butyl ester, or 2,6-diaza-spiro[3.3]heptane-2-carboxylic acid tert-butyl ester, trifluoroacetic acid, and commercially available sulfonyl chlorides derivatives, in accordance with the procedure described for example 1-1.

| Example No. | Systematic Name | $^1$H NMR (400 MHz, CD$_3$OD) δ ppm | MS (ESI$^+$, [(M + H)$^+$] | Structure |
|---|---|---|---|---|
| 1-2* | [4-(4-Ethanesulfonyl-piperazine-1-carbonyl)-6-fluoro-naphthalen-2-yl]-acetic acid | 7.86 (dd, J = 8.97, 5.68 Hz, 1H), 7.80 (s, 1H), 7.41-7.48 (m, 2H), 7.30-7.36 (m, 1H), 4.03 (br. s, 2H), 3.81 (s, 2H), 3.44-3.53 (m, 2H), 3.33 (br. s, 2H), 3.18 (br. s, 2H), 2.99 (q, J = 7.33 Hz, 2H), 1.39 (t, J = 7.45 Hz, 3H) | 409 | 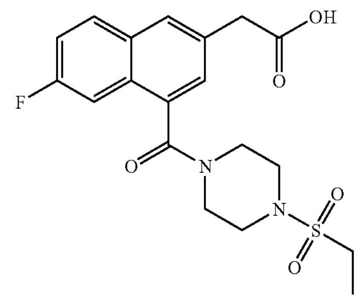 |
| 1-3 | [6-Fluoro-4-(4-methanesulfonyl-piperazine-1-carbonyl)-3-methyl-naphthalen-2-yl]-acetic acid | 7.94 (dd, J = 8.72, 5.68 Hz, 1H), 7.85 (s, 1H), 7.24-7.36 (m, 2H), 3.97-4.16 (m, 2H), 3.88 (s, 2H), 3.39-3.47 (m, 2H), 3.19-3.27 (m, 2H), 3.00-3.17 (m, 2H), 2.87 (s, 3H), 2.38 (s, 3H) | 409 | 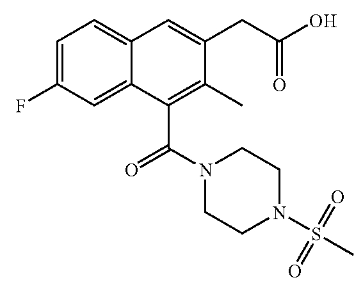 |
| 1-4 | {6-Fluoro-3-methyl-4-[4-(propane-2-sulfonyl)-piperazine-1-carbonyl]-naphthalen-2-yl}-acetic acid | 7.95 (dd, J = 8.97, 5.68 Hz, 1H), 7.86 (s, 1H), 7.25-7.37 (m, 2H), 3.93-4.13 (m, 2H), 3.89 (s, 2H), 3.58 (t, J = 5.18 Hz, 2H), 3.35-3.38 (m, 1H), 3.13-3.30 (m, 4H), 2.41 (s, 3H), 1.33 (dd, J = 6.82, 2.02 Hz, 6H) | 437 | 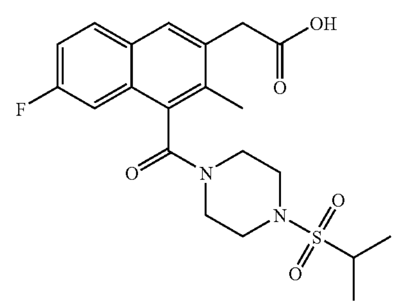 |
| 1-5 | [6-Fluoro-3-methyl-4-(4-trifluoromethanesulfonyl-piperazine-1-carbonyl)-naphthalen-2-yl]-acetic acid | 7.93 (dd, J = 8.97, 5.68 Hz, 1H), 7.85 (s, 1H), 7.24-7.38 (m, 2H), 3.92-4.34 (m, 2H), 3.85-3.91 (m, 2H), 3.63-3.84 (m, 2H), 3.34-3.52 (m, 2H), 3.21-3.29 (m, 2H), 2.36 (s, 3H) | 463 | 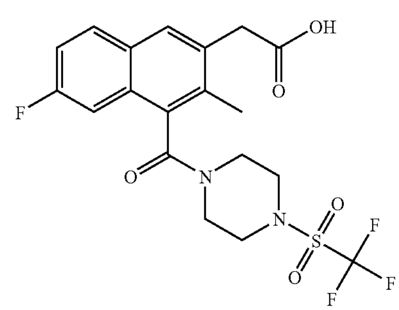 |

| Example No. | Systematic Name | ¹H NMR (400 MHz, CD₃OD) δ ppm | MS (ESI⁺, [(M + H)⁺] | Structure |
|---|---|---|---|---|
| 1-6 | [4-(4-Cyclopropanesulfonyl-piperazine-1-carbonyl)-6-fluoro-3-methyl-naphthalen-2-yl]-acetic acid | 7.94 (dd, J = 8.72, 5.94 Hz, 1H), 7.85 (s, 1H), 7.24-7.37 (m, 2H), 3.96-4.17 (m, 2H), 3.89 (s, 2H), 3.51 (t, J = 5.18 Hz, 2H), 3.06-3.29 (m, 4H), 2.49-2.57 (m, 1H), 2.40 (s, 3H), 0.96-1.12 (m, 4H) | 435 | 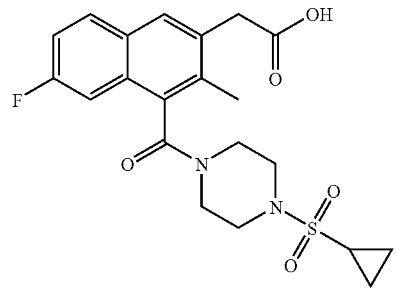 |
| 1-7* | {6-Fluoro-4-[4-(propane-1-sulfonyl)-piperazine-1-carbonyl]-naphthalen-2-yl}-acetic acid | 7.86 (dd, 1H), 7.80 (s, 1H), 7.43 (br. s, 2H), 7.30-7.36 (m, 1H), 4.02 (br. s, 2H), 3.79 (br. s, 2H), 3.46 (br. s, 2H), 3.32 (br. s, 2H), 3.16 (br. s, 2H), 2.91 (br. s, 2H), 1.86 (br. s, 2H), 1.04-1.11 (m, 3H) | 423 | 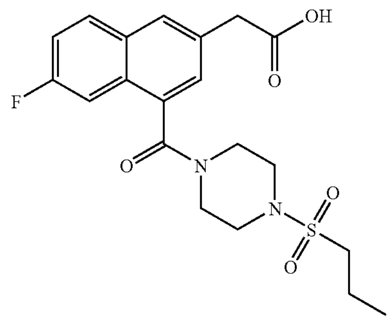 |
| 1-8 | [4-(4-Cyclopentanesulfonyl-piperazine-1-carbonyl)-6-fluoro-3-methyl-naphthalen-2-yl]-acetic acid | 7.93 (dd, J = 8.84, 5.81 Hz, 1H), 7.85 (s, 1H), 7.23-7.37 (m, 2H), 3.91-4.12 (m, 2H), 3.88 (s, 2H), 3.59-3.68 (m, 1H), 3.52 (t, J = 5.18 Hz, 2H), 3.08-3.28 (m, 4H), 2.39 (s, 3H), 1.86-2.05 (m, 4H), 1.59-1.81 (m, 4H) | 463 | 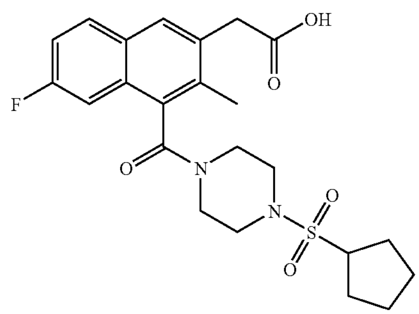 |
| 1-9 | [4-(4-Benzenesulfonyl-piperazine-1-carbonyl)-6-fluoro-3-methyl-naphthalen-2-yl]-acetic acid | 7.90 (dd, J = 8.84, 5.81 Hz, 1H), 7.69-7.83 (m, 4H), 7.64 (t, J = 7.58 Hz, 2H), 7.28 (td, J = 8.72, 2.27 Hz, 1H), 7.05 (dd, J = 10.48, 2.65 Hz, 1H), 3.91-4.15 (m, 2H), 3.84 (s, 2H), 3.12-3.28 (m, 4H), 2.72-2.95 (m, 2H), 2.24 (s, 3H) | 471 | 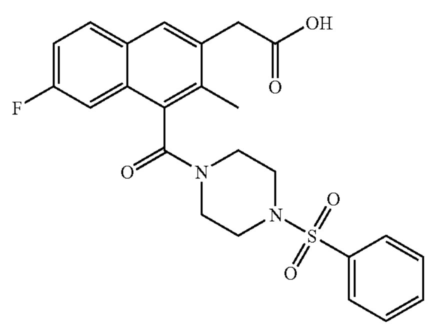 |
| 1-10 | [4-(6-Benzenesulfonyl-2,6-diaza-spiro[3.3]heptane-2-carbonyl)-6-fluoro-3-methyl-naphthalen-2-yl]-acetic acid | 7.77-7.92 (m, 4H), 7.59-7.73 (m, 3H), 7.21-7.32 (m, 2H), 4.14-4.27 (m, 2H), 3.99 (dd, J = 9.60, 1.52 Hz, 2H), 3.83-3.93 (m, 2H), 3.80 (s, 2H), 3.74 (d, J = 10.86 Hz, 1H), 3.56 (d, J = 9.85 Hz, 1H), 2.35 (s, 3H) | 483 | 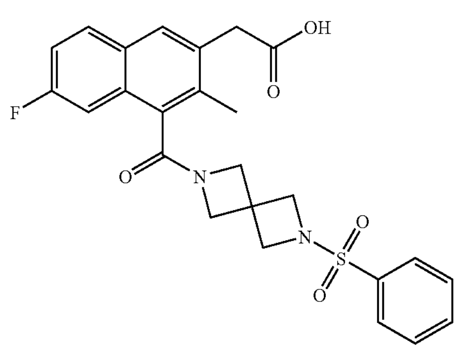 |

-continued

| Example No. | Systematic Name | ¹H NMR (400 MHz, CD₃OD) δ ppm | MS (ESI⁺, [(M + H)⁺] | Structure |
|---|---|---|---|---|
| 1-11 | [6-Fluoro-3-methyl-4-(6-phenylmethanesulfonyl-2,6-diaza-spiro[3.3]heptane-2-carbonyl)-naphthalen-2-yl]-acetic acid | 7.91 (dd, J = 9.85, 5.81 Hz, 1H), 7.83 (s, 1H), 7.38-7.45 (m, 2H), 7.27-7.38 (m, 5H), 4.35-4.46 (m, 2H), 4.34 (s, 2H), 4.02 (t, J = 8.08 Hz, 2H), 3.82-3.92 (m, 5H), 3.73 (dd, J = 9.85, 1.01 Hz, 1H), 2.39 (s, 3H) | 497 | 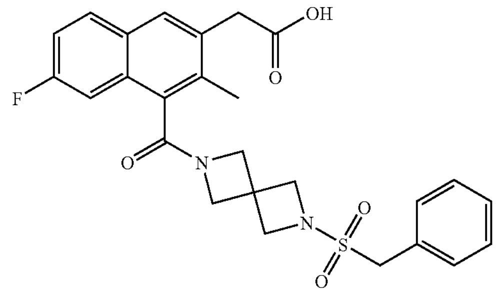 |
| 1-12 | {6-Fluoro-4-[4-(4-fluoro-benzenesulfonyl)-piperazine-1-carbonyl]-3-methyl-naphthalen-2-yl}-acetic acid | 7.80-7.93 (m, 4H), 7.37 (t, J = 8.59 Hz, 2H), 7.28 (td, J = 8.78, 2.40 Hz, 1H), 7.06 (dd, J = 10.48, 2.15 Hz, 1H), 3.88-4.19 (m, 2H), 3.84 (s, 2H), 3.10-3.29 (m, 4H), 2.69-2.98 (m, 2H), 2.22-2.31 (m, 3H) | 489 | 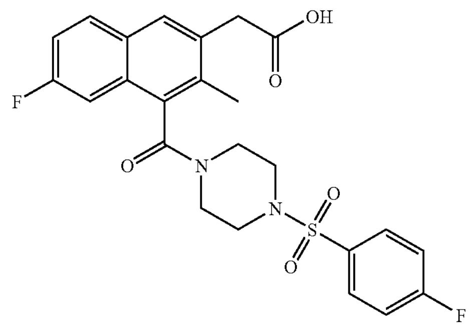 |
| 1-13 | [6-Fluoro-3-methyl-4-(4-phenylmethanesulfonyl-piperazine-1-carbonyl)-naphthalen-2-yl]-acetic acid | 7.93 (dd, J = 8.97, 5.68 Hz, 1H), 7.83 (s, 1H), 7.44-7.49 (m, 2H), 7.37-7.43 (m, 3H), 7.30-7.37 (m, 1H), 7.20 (dd, J = 10.74, 1.89 Hz, 1H), 4.41 (s, 2H), 3.87 (s, 2H), 3.77-4.05 (m, 2H), 3.33-3.41 (m, 2H), 2.83-3.16 (m, 4H), 2.34 (s, 3H) | 485 | 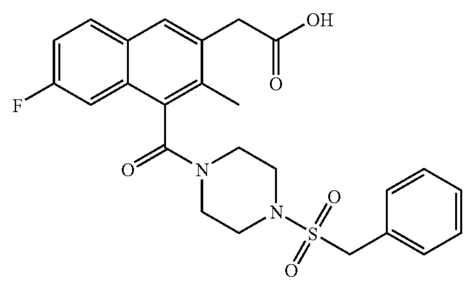 |
| 1-14 | {6-Fluoro-4-[4-(2-fluoro-benzenesulfonyl)-piperazine-1-carbonyl]-3-methyl-naphthalen-2-yl}-acetic acid | 7.91 (dd, J = 8.97, 5.68 Hz, 1H), 7.81-7.86 (m, 2H), 7.70-7.77 (m, 1H), 7.35-7.42 (m, 2H), 7.26-7.33 (m, 1H), 7.14 (dd, J = 10.61, 2.02 Hz, 1H), 3.93-4.15 (m, 2H), 3.85 (s, 2H), 3.35-3.44 (m, 2H), 3.17-3.29 (m, 2H), 2.93-3.13 (m, 2H), 2.31 (s, 3H) | 489 | 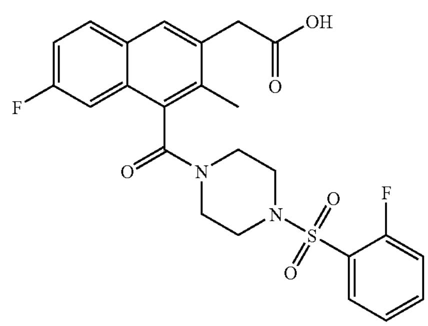 |
| 1-15 | {4-[4-(3,4-Difluoro-benzenesulfonyl)-piperazine-1-carbonyl]-6-fluoro-3-methyl-naphthalen-2-yl}-acetic acid | 7.90 (dd, J = 8.97, 5.94 Hz, 1H), 7.82 (s, 1H), 7.73-7.79 (m, 1H), 7.61-7.66 (m, 1H), 7.57 (dd, J = 9.85, 7.58 Hz, 1H), 7.29 (td, J = 8.72, 2.53 Hz, 1H), 7.08 (dd, J = 10.36, 2.02 Hz, 1H), 3.87-4.22 (m, 2H), 3.85 (s, 2H), 3.12-3.28 (m, 4H), 2.71-3.02 (m, 2H), 2.28 (s, 3H) | 507 | 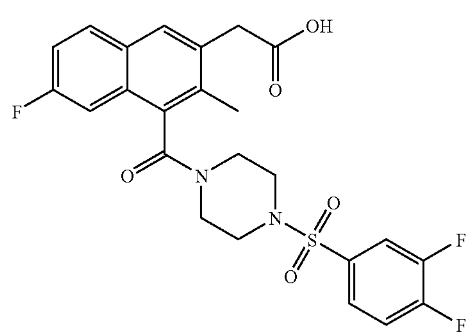 |

| Example No. | Systematic Name | ¹H NMR (400 MHz, CD₃OD) δ ppm | MS (ESI⁺, [(M + H)⁺] | Structure |
| --- | --- | --- | --- | --- |
| 1-16 | {6-Fluoro-4-[4-(3-fluoro-benzenesulfonyl)-piperazine-1-carbonyl]-3-methyl-naphthalen-2-yl}-acetic acid | 7.90 (dd, J = 9.09, 5.81 Hz, 1H), 7.82 (s, 1H), 7.65-7.71 (m, 1H), 7.58-7.63 (m, 1H), 7.46-7.57 (m, 2H), 7.28 (td, J = 8.72, 2.27 Hz, 1H), 7.08 (dd, J = 10.36, 2.02 Hz, 1H), 3.91-4.18 (m, 2H), 3.84 (s, 2H), 3.12-3.29 (m, 4H), 2.73-3.00 (m, 2H), 2.27 (s, 3H) | 489 | 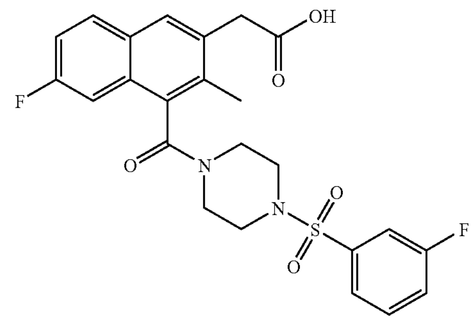 |
| 1-17 | {4-[4-(2,4-Difluoro-benzenesulfonyl)-piperazine-1-carbonyl]-6-fluoro-3-methyl-naphthalen-2-yl}-acetic acid | 7.90 (dd, J = 8.97, 5.68 Hz, 1H), 7.83 (s, 1H), 7.36-7.47 (m, 3H), , 7.29 (td, J = 8.78, 2.15 Hz, 1H), 7.11 (dd, J = 10.48, 2.40 Hz, 1H), 3.90-4.21 (m, 2H), 3.84 (s, 2H), 3.12-3.29 (m, 4H), 2.78-3.05 (m, 2H), 2.30 (s, 3H) | 507 | 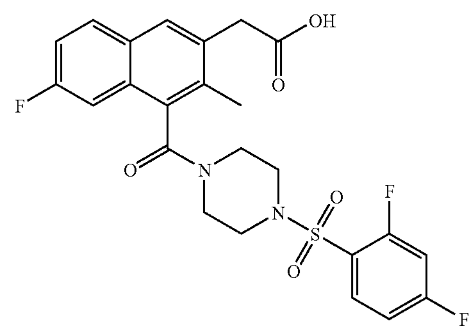 |
| 1-18 | [4-(4-Benzenesulfonyl-piperazine-1-carbonyl)-6-trifluoromethyl-naphthalen-2-yl]-acetic acid | 8.12 (d, J = 8.84 Hz, 2H), 7.99 (s, 1H), 7.96 (s, 1H), 7.81 (s, 1H), 7.79 (s, 1H), 7.71-7.78 (m, 2H), 7.63-7.69 (m, 2H), 7.55 (s, 1H), 3.90-4.17 (m, 2H), 3.87 (s, 2H), 3.35-3.50 (m, 2H), 2.71-3.32 (m, 4H) | 507 | 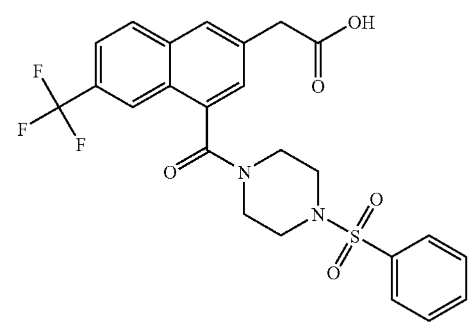 |
| 1-19 | [4-(4-Benzenesulfonyl-piperazine-1-carbonyl)-6-trifluoromethoxy-naphthalen-2-yl]-acetic acid | 8.04 (d, J = 8.84 Hz, 1H), 7.94 (s, 1H), 7.80 (d, J = 8.08 Hz, 2H), 7.71-7.77 (m, 1H), 7.61-7.69 (m, 2H), 7.49 (s, 2H), 7.45 (d, J = 9.60 Hz, 1H), 3.86-4.20 (m, 2H), 3.83 (s, 2H), 3.36-3.49 (m, 2H), 2.65-3.30 (m, 4H) | 523 | 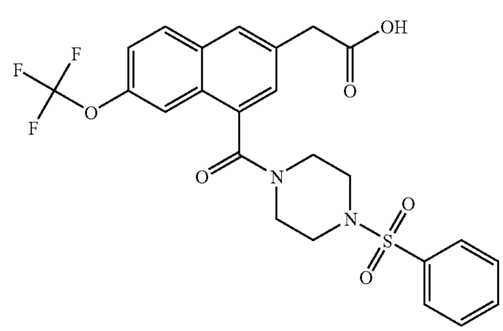 |

*CDCl₃ was used as the solvent.

Example 2-1

{6-Fluoro-4-[4-(4-fluoro-phenyl)-piperazine-1-carbonyl]-3-methyl-naphthalen-2-yl}-acetic acid

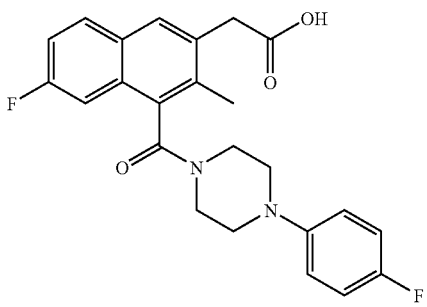

{6-Fluoro-4-[4-(4-fluoro-phenyl)-piperazine-1-carbonyl]-3-methyl-naphthalen-2-yl}-acetic acid methyl ester

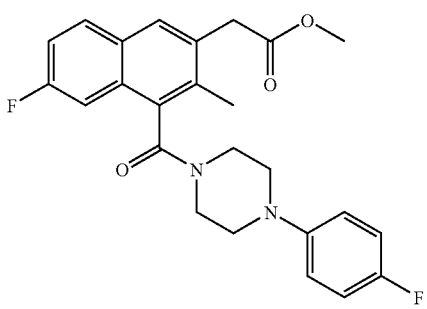

To a solution of 7-fluoro-3-methoxycarbonylmethyl-2-methyl-naphthalene-1-carboxylic acid (27.6 mg, 0.10 mmol) and 1-(4-fluoro-phenyl)-piperazine (19.8 mg, 0.11 mmol) in N,N-dimethylformamide (2 mL) was added bromo-tris-pyrrolidino phosphonium hexafluorophosphate (46.6 mg, 0.10 mmol) and N,N-diisopropylethylamine (34.7 μL, 0.20 mmol). After being stirred at room temperature for 24 hours, the resulting mixture was diluted with ethyl acetate (10 mL), and washed with 1N hydrochloric acid (10 mL), a saturated aqueous solution of sodium carbonate (10 mL), and brine (10 mL). The resulting organic phase was dried over sodium sulfate, filtered, and concentrated in vacuo. The residue was purified by column chromatography (gradient elution with 20-40% ethyl acetate in petroleum ether) to afford {6-fluoro-4-[4-(4-fluoro-phenyl)-piperazine-1-carbonyl]-3-methyl-naphthalen-2-yl}-acetic acid methyl ester (36.2 mg, 83%) as a white solid.

{6-Fluoro-4-[4-(4-fluoro-phenyl)-piperazine-1-carbonyl]-3-methyl-naphthalen-2-yl}-acetic acid

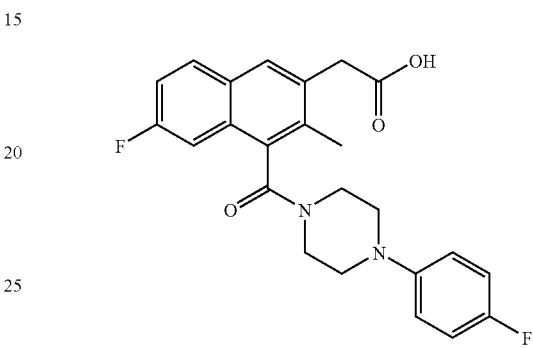

Starting with {6-fluoro-4-[4-(4-fluoro-phenyl)-piperazine-1-carbonyl]-3-methyl-naphthalen-2-yl}-acetic acid methyl ester (36.2 mg, 0.08 mmol), using a method analogous to the one described above for example 1-1, {6-fluoro-4-[4-(4-fluoro-phenyl)-piperazine-1-carbonyl]-3-methyl-naphthalen-2-yl}-acetic acid was obtained (15 mg, 43%) as a white solid. $^1$H NMR (400 MHz, CD$_3$OD) δ ppm 7.91 (dd, 1H), 7.83 (s, 1H), 7.22-7.33 (m, 2H), 6.97 (d, 4H), 4.03-4.16 (m, 2H), 3.81 (d, 2H), 3.22-3.30 (m, 4H), 2.87-3.02 (m, 2H), 2.41 (s, 3H); MS cald. for C$_{24}$H$_{22}$F$_2$N$_2$O$_3$ 424, obsd. (ESI$^+$) [(M+H)$^+$] 425.

Examples 2-2 to 2-24

The following examples 2-2 to 2-24 were prepared in an analogous manner to example 2-1 starting with 7-fluoro-3-methoxycarbonylmethyl-2-methyl-naphthalene-1-carboxylic acid, and commercially available 1-aryl-piperazines.

| Example No. | Systematic Name | $^1$H NMR (400 MHz, CD$_3$OD) δ ppm | MS (ESI$^+$), [(M + H)$^+$] | Structure |
|---|---|---|---|---|
| 2-2 | [6-Fluoro-3-methyl-4-(4-pyridin-2-yl-piperazine-1-carbonyl)-naphthalen-2-yl]-acetic acid | 8.07-8.11 (m, 1H), 7.89-7.94 (m, 1H), 7.83 (s, 1H), 7.53-7.59 (m, 1H), 7.22-7.33 (m, 2H), 6.83 (d, 1H), 6.68-6.72 (m, 1H), 4.00-4.12 (m, 2H), 3.81 (d, 1H), 3.73-3.77 (m, 2H), 3.32-3.53 (m, 4H), 2.42 (s, 3H) | 408 | 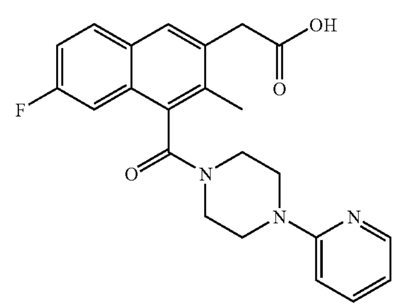 |

-continued

| Example No. | Systematic Name | ¹H NMR (400 MHz, CD₃OD) δ ppm | MS (ESI⁺, [(M + H)⁺] | Structure |
|---|---|---|---|---|
| 2-3 | {6-Fluoro-4-[4-(2-fluoro-phenyl)-piperazine-1-carbonyl]-3-methyl-naphthalen-2-yl}-acetic acid | 7.91 (dd, J = 8.84, 5.81 Hz, 1H), 7.82 (s, 1H), 7.23-7.32 (m, 2H), 6.95-7.12 (m, 4H), 4.04-4.18 (m, 2H), 3.79 (d, J = 5.56-Hz, 2H), 3.19-3.28 (m, 4H), 2.85-3.00 (m, 2H), 2.44 (s, 3H) | 425 | 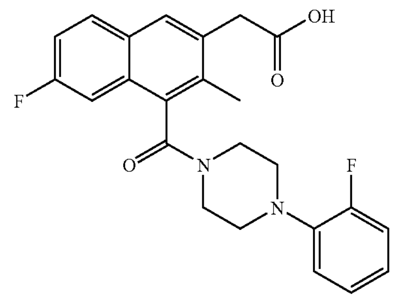 |
| 2-4 | [6-Fluoro-3-methyl-4-(4-phenyl-piperazine-1-carbonyl)-naphthalen-2-yl]-acetic acid | 7.92 (dd, J = 9.09, 5.81 Hz, 1H), 7.84 (s, 1H), 7.19-7.34 (m, 4H), 6.97 (d, J = 8.08 Hz, 2H), 6.86 (t, J = 7.20 Hz, 1H), 4.03-4.17 (m, 2H), 3.85 (d, J = 2.02 Hz, 3H), 3.33-3.39 (m, 4H), 2.94-3.08 (m, 2H), 2.42 (s, 3H) | 407 | 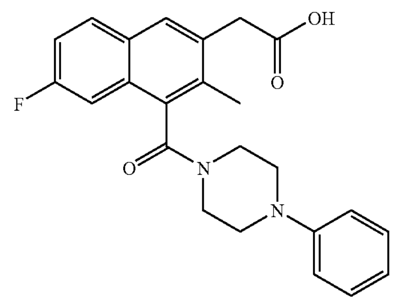 |
| 2-5 | [6-Fluoro-3-methyl-4-(4-pyrimidin-2-yl-piperazine-1-carbonyl)-naphthalen-2-yl]-acetic acid | 8.33 (d, J = 4.80 Hz, 2H), 7.92 (dd, J = 8.84, 5.56 Hz, 1H), 7.84 (s, 1H), 7.23-7.33 (m, 2H), 6.62 (t, J = 4.80 Hz, 1H), 3.95-4.10 (m, 4H), 3.83 (s, 2H), 3.61-3.78 (m, 2H), 3.18-3.28 (m, 2H), 2.42 (s, 3H) | 409 | 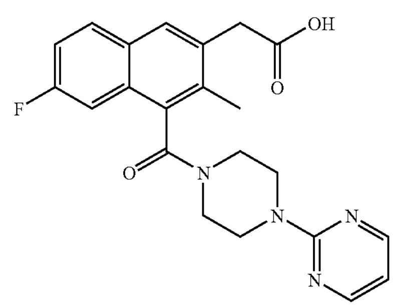 |
| 2-6 | [6-Fluoro-3-methyl-4-(4-m-tolyl-piperazine-1-carbonyl)-naphthalen-2-yl]-acetic acid | 7.96 (dd, J = 9.09, 5.81 Hz, 1H), 7.87 (s, 1H), 7.28-7.38 (m, 2H), 7.16 (t, J = 7.83 Hz, 1H), 6.88 (s, 1H), 6.84 (d, J = 7.58 Hz, 1H), 6.78 (d, J = 7.33 Hz, 1H), 4.09-4.19 (m, 2H), 3.91 (s, 2H), 3.35-3.51 (m, 4H), 2.98-3.13 (m, 2H), 2.44 (s, 3H), 2.31 (s, 3H) | 421 | 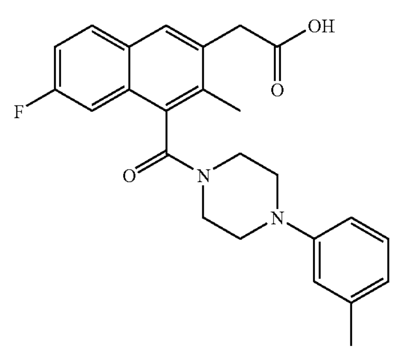 |

-continued

| Example No. | Systematic Name | $^1$H NMR (400 MHz, CD$_3$OD) δ ppm | MS (ESI$^+$, [(M + H)$^+$] | Structure |
|---|---|---|---|---|
| 2-7 | {6-Fluoro-3-methyl-4-[4-(3-trifluoromethyl-phenyl)-piperazine-1-carbonyl]-naphthalen-2-yl}-acetic acid | 7.94-7.98 (m, 1H), 7.87 (s, 1H), 7.42 (t, J = 8.34 Hz, 1H), 7.26-7.37 (m, 2H), 7.19-7.25 (m, 2H), 7.13 (d, J = 7.58 Hz, 1H), 4.14 (t, J = 5.18 Hz, 2H), 3.90 (s, 2H), 3.34-3.53 (m, 4H), 3.05-3.19 (m, 2H), 2.44 (s, 3H) | 475 | 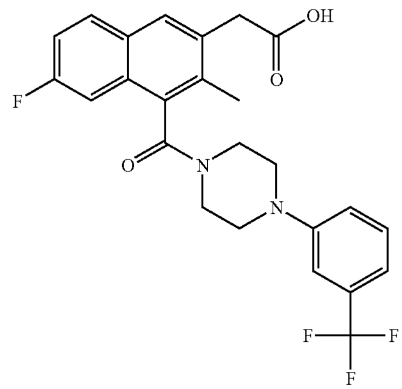 |
| 2-8 | {6-Fluoro-4-[4-(2-methoxy-phenyl)-piperazine-1-carbonyl]-3-methyl-naphthalen-2-yl}-acetic acid | 7.96 (dd, J = 9.09, 5.81 Hz, 1H), 7.88 (s, 1H), 7.30-7.39 (m, 2H), 7.15-7.22 (m, 2H), 7.07 (d, J = 7.33 Hz, 1H), 7.00 (t, J = 7.71 Hz, 1H), 4.10-4.31 (m, 2H), 3.92 (s, 5H), 3.37-3.51 (m, 4H), 3.01-3.17 (m, 2H), 2.45 (s, 3H) | 437 | 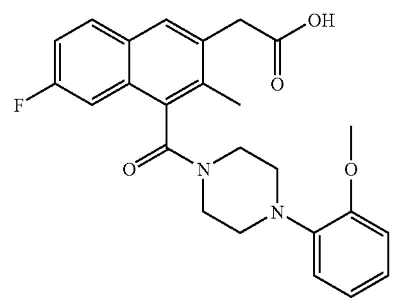 |
| 2-9 | {6-Fluoro-4-[4-(3-methoxy-phenyl)-piperazine-1-carbonyl]-3-methyl-naphthalen-2-yl}-acetic acid | 7.95 (dd, J = 9.09, 5,81 Hz, 1H), 7.87 (s, 1H), 7.28-7.37 (m, 2H), 7.17 (t, J = 8.21 Hz, 1H), 6.61 (dd, J = 8.21, 1.89 Hz, 1H), 6.55 (s, 1H), 6.50 (dd, J = 8.08, 1.77 Hz, 1H), 4.06-4.19 (m, 2H), 3.90 (s, 2H), 3.77 (s, 3H), 3.34-3.45 (m, 4H), 2.98-3.12 (m, 2H), 2.43 (s, 3H) | 437 | 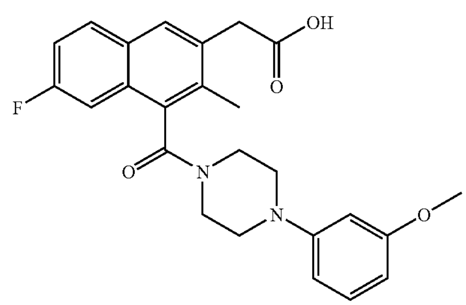 |
| 2-10** | {4-[4-(2-Ethyl-phenyl)-piperazine-1-carbonyl]-6-fluoro-3-methyl-naphthalen-2-yl}-acetic acid | 7.99 (dd, J = 8.84, 6.06 Hz, 1H), 7.84 (s, 1H), 7.42 (td, J = 8.91, 2.40 Hz, 1H), 7.28 (dd, J = 10.74, 2.15 Hz, 1H), 7.21 (d, J = 7.33 Hz, 1H), 7.12-7.18 (m, 1H), 7.01-7.10 (m, 2H), 4.00-4.07 (m, 4H), 3.80 (s, 2H), 2.88-3.03 (m, 2H), 2.65 (q, J = 7.66 Hz, 4H), 2.32 (s, 3H), 1.17 (t, J = 7.45 Hz, 3H) | 435 | 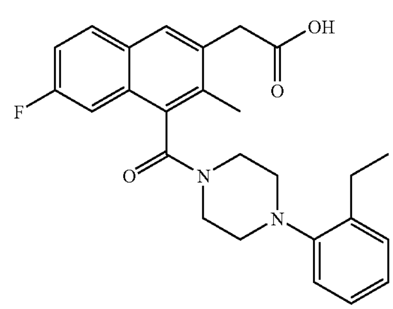 |

| Example No. | Systematic Name | $^1$H NMR (400 MHz, CD$_3$OD) δ ppm | MS (ESI$^+$, [(M + H)$^+$] | Structure |
|---|---|---|---|---|
| 2-11 | {4-[4-(3,5-Bis-trifluoromethyl-phenyl)-piperazine-1-carbonyl]-6-fluoro-3-methyl-naphthalen-2-yl}-acetic acid | 7.95-7.98 (m, 1H), 7.88 (s, 1H), 7.46 (s, 1H), 7.28-7.37 (m, 3H), 4.12-4.18 (m, 2H), 3.91 (s, 2H), 3.50-3.67 (m, 2H), 3.35-3.44 (m, 2H), 3.18-3.28 (m, 2H), 2.44 (s, 3H) | 543 | 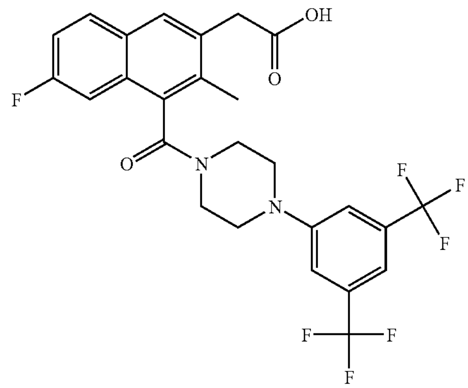 |
| 2-12 | {6-Fluoro-4-[4-(4-methoxy-phenyl)-piperazine-1-carbonyl]-3-methyl-naphthalen-2-yl}-acetic acid | 7.93 (dd, J = 8.59, 6.06 Hz, 1H), 7.85 (s, 1H), 7.24-7.37 (m, 2H), 7.02-7.10 (m, 2H), 6.83-6.92 (m, 2H), 4.07-4.20 (m, 2H), 3.89 (s, 2H), 3.74 (s, 3H), 3.33-3.45 (m, 4H), 2.92-3.07 (m, 2H), 2.40 (s, 3H) | 437 | 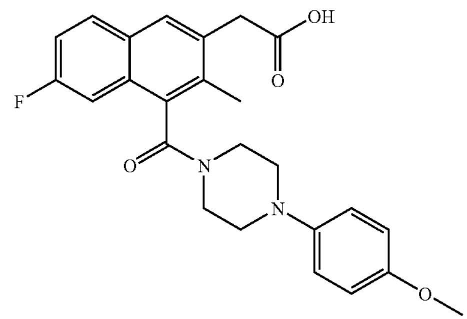 |
| 2-13 | {4-[4-(2,4-Difluoro-phenyl)-piperazine-1-carbonyl]-6-fluoro-3-methyl-naphthalen-2-yl}-acetic acid | 7.95 (dd, J = 9.22, 5.68 Hz, 1H), 7.87 (s, 1H), 7.28-7.39 (m, 2H), 7.05-7.14 (m, 1H), 6.85-6.99 (m, 2H), 4.04-4.23 (m, 2H), 3.91 (s, 2H), 3.34-3.38 (m, 2H), 3.20-3.26 (m, 2H), 2.83-2.96 (m, 2H), 2.43 (s, 3H) | 443 | 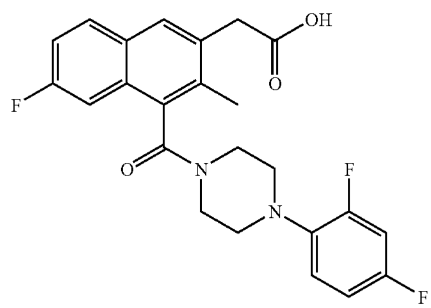 |
| 2-14** | {4-[4-(3,5-Dimethoxy-phenyl)-piperazine-1-carbonyl]-6-fluoro-3-methyl-naphthalen-2-yl}-acetic acid | 8.00 (dd, J = 9.35, 6.06 Hz, 1H), 7.87 (s, 1H), 7.39-7.46 (m, 1H), 7.25 (dd, J = 10.48, 1.89 Hz, 1H), 6.07 (d, J = 1.77 Hz, 2H), 5.99 (s, 1H), 3.79-4.04 (m, 4H), 3.68 (s, 6H), 3.26-3.38 (m, 2H), 3.07-3.17 (m, 2H), 2.87-3.05 (m, 2H), 2.24-2.34 (m, 3H) | 467 | 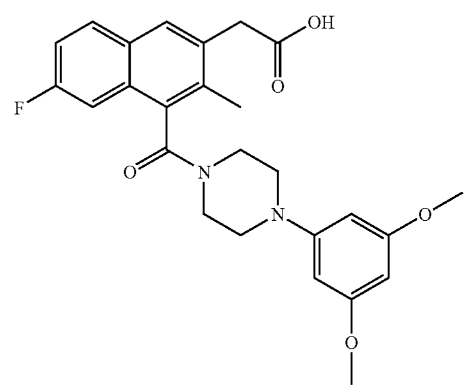 |

| Example No. | Systematic Name | $^{1}$H NMR (400 MHz, CD$_3$OD) δ ppm | MS (ESI$^+$, [(M + H)$^+$] | Structure |
| --- | --- | --- | --- | --- |
| 2-15 | {6-Fluoro-3-methyl-4-[4-(2-trifluoromethyl-phenyl)-piperazine-1-carbonyl]-naphthalen-2-yl}-acetic acid | 7.92-7.98 (m, 1H), 7.86 (s, 1H), 7.66 (t, 1H), 7.51-7.55 (m, 1H), 7.25-7.41 (m, 3H), 3.98-4.24 (m, 2H), 3.90 (s, 2H), 3.30-3.31 (m, 2H), 3.11-3.17 (m, 2H), 2.74-2.87 (m, 2H), 2.46 (s, 3H) | 475 | 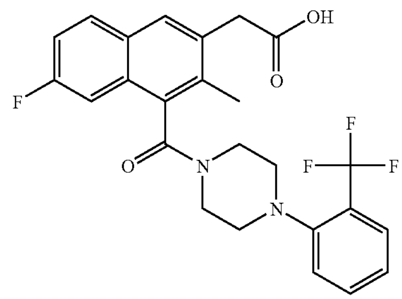 |
| 2-16 | [6-Fluoro-3-methyl-4-(4-p-tolyl-piperazine-1-carbonyl)-naphthalen-2-yl]-acetic acid | 7.94 (dd, J = 8.84, 5.56 Hz, 1H), 7.85 (s, 1H), 7.27-7.36 (m, 2H), 7.13 (d, J = 8.34 Hz, 2H), 7.01 (d, J = 8.59 Hz, 2H), 4.12-4.23 (m, 2H), 3.89 (s, 2H), 3.32-3.49 (m, 4H), 2.98-3.14 (m, 2H), 2.42 (s, 3H), 2.26 (s, 3H) | 421 | 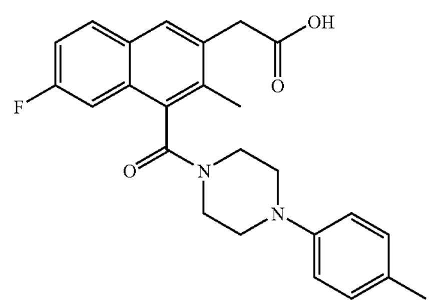 |
| 2-17 | {4-[4-(3,5-Dichloro-phenyl)-piperazine-1-carbonyl]-6-fluoro-3-methyl-naphthalen-2-yl}-acetic acid | 7.93 (dd, J = 8.97, 5.68 Hz, 1H), 7.85 (s, 1H), 7.24-7.36 (m, 2H), 6.90 (d, J = 1.77 Hz, 2H), 6.83 (s, 1H), 4.06-4.12 (m, 2H), 3.88 (s, 2H), 3.37-3.51 (m, 2H), 3.23-3.29 (m, 2H), 3.02-3.17 (m, 2H), 2.41 (s, 3H) | 475 | 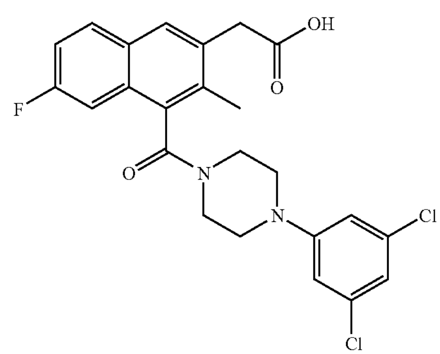 |
| 2-18 | {4-[4-(4-Chloro-phenyl)-piperazine-1-carbonyl]-6-fluoro-3-methyl-naphthalen-2-yl}-acetic acid | 7.93 (dd, J = 9.09, 5.81 Hz, 1H), 7.85 (s, 1H), 7.27-7.35 (m, 2H), 7.20 (d, J = 9.09 Hz, 2H), 6.94 (d, J = 9.09 Hz, 2H), 4.10-4.17 (m, 2H), 3.88 (s, 2H), 3.32-3.41 (m, 4H), 2.91-3.10 (m, 2H), 2.41 (s, 3H) | 441 | 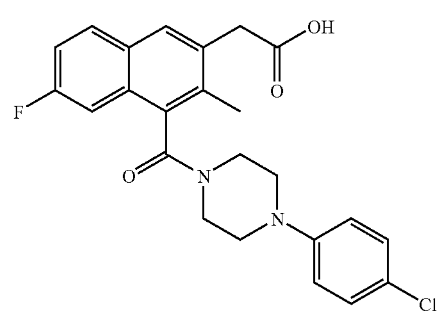 |

| Example No. | Systematic Name | ¹H NMR (400 MHz, CD$_3$OD) δ ppm | MS (ESI⁺, [(M + H)⁺] | Structure |
|---|---|---|---|---|
| 2-19 | {6-Fluoro-3-methyl-4-[4-(4-trifluoromethyl-phenyl)-piperazine-1-carbonyl]-naphthalen-2-yl}-acetic acid | 7.94 (dd, J = 8.84, 5.81 Hz, 1H), 7.86 (s, 1H), 7.49 (d, J = 8.59 Hz, 2H), 7.25-7.35 (m, 2H), 7.06 (d, J = 8.59 Hz, 2H), 4.04-4.19 (m, 2H), 3.89 (s, 2H), 3.52 (t, J = 5.05 Hz, 2H), 3.32-3.39 (m, 2H), 3.08-3.25 (m, 2H), 2.14 (s, 3H) | 475 | 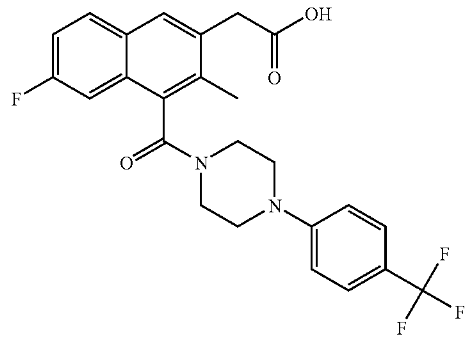 |
| 2-20 | {4-[4-(2-Chloro-phenyl)-piperazine-1-carbonyl]-6-fluoro-3-methyl-naphthalen-2-yl}-acetic acid | 7.93 (dd, J = 8.84, 5.81 Hz, 1H), 7.84 (s, 1H), 7.23-7.39 (m, 4H), 7.14 (d, J = 6.82 Hz, 1H), 7.00-7.06 (m, 1H), 4.04-4.23 (m, 2H) 3.88 (s, 2H), 3.33-3.40 (m, 2H), 3.23 (t, J = 5.18 Hz, 2H), 2.81-2.98 (m, 2H), 2.41-2.46 (m, 3H) | 441 | 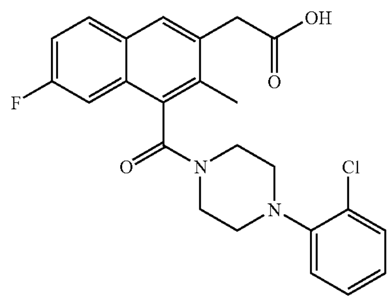 |
| 2-21 | {4-[4-(3-Chloro-phenyl)-piperazine-1-carbonyl]-6-fluoro-3-methyl-naphthalen-2-yl}-acetic acid | 7.95 (dd, J = 8.84, 5.81 Hz, 1H), 7.87 (s, 1H), 7.26-7.38 (m, 2H), 7.21 (d, J = 8.08 Hz, 1H), 6.97-7.00 (m, 1H), 6.91 (d, J = 8.34 Hz, 1H), 6.85 (d, J = 7.58 Hz, 1H), 4.08-4.16 (m, 2H), 3.89 (s, 2H), 3.35-3.51 (m, 4H), 3.00-3.14 (m, 2H), 2.42 (s, 3H) | 441 | 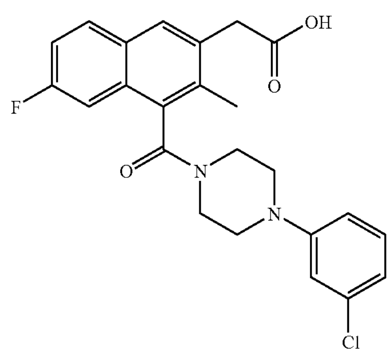 |
| 2-22 | {6-Fluoro-3-methyl-4-[4-(5-trifluoromethyl-pyridin-2-yl)-piperazine-1-carbonyl]-naphthalen-2-yl}-acetic acid | 8.36 (s, 1H), 7.94 (dd, J = 8.84, 5.56 Hz, 1H), 7.86 (s, 1H), 7.76 (d, J = 8.59 Hz, 1H), 7.26-7.36 (m, 2H), 6.92 (d, J = 9.35 Hz, 1H), 4.02-4.12 (m, 2H), 3.91-3.95 (m, 2H), 3.89 (s, 2H), 3.53-3.64 (m, 2H), 3.20-3.27 (m, 2H), 2.41 (s, 3H) | 476 | 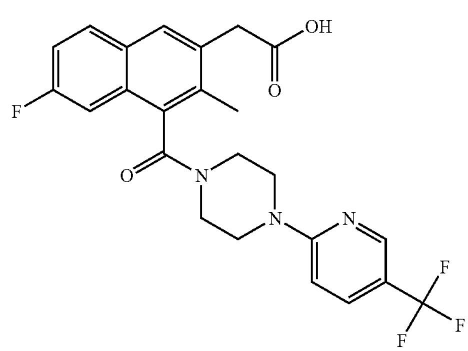 |

-continued

| Example No. | Systematic Name | $^1$H NMR (400 MHz, CD$_3$OD) δ ppm | MS (ESI$^+$, [(M + H)$^+$] | Structure |
|---|---|---|---|---|
| 2-23 | {4-[4-(3,5-Dichloro-pyridin-4-yl)-piperazine-1-carbonyl]-6-fluoro-3-methyl-naphthalen-2-yl}-acetic acid | 8.40 (s, 1H), 7.94 (d, J = 7.07 Hz, 1H), 7.85 (s, 1H), 7.29-7.36 (m, 2H), 4.03-4.24 (m, 2H), 3.89 (s, 2H), 3.53-3.64 (m, 2H), 3.33-3.40 (m, 2H), 3.21-3.27 (m, 2H), 2.44 (s, 3H) | 476 | 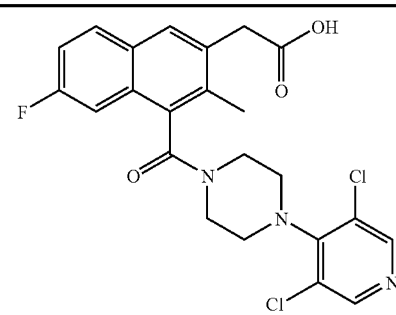 |
| 2-24 | {4-[4-(4-Cyano-phenyl)-piperazine-1-carbonyl]-6-fluoro-3-methyl-naphthalen-2-yl}-acetic acid | 7.94 (dd, J = 9.09, 5.81 Hz, 1H), 7.85 (s, 1H), 7.53 (d, J = 9.09 Hz, 2H), 7.24-7.35 (m, 2H), 7.01 (d, J = 8.84 Hz, 2H), 4.03-4.16 (m, 2H), 3.88 (s, 2H), 3.60 (t, J = 5.56 Hz, 2H), 3.19-3.27 (m, 4H), 2.39 (s, 3H) | 432 | 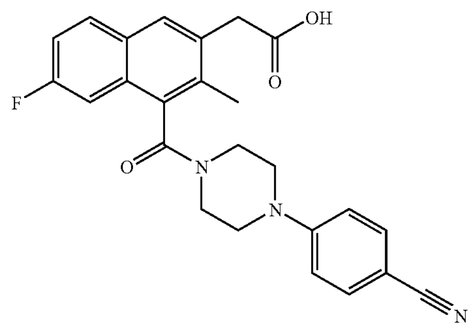 |

**DMSO-d$_6$ was used as the solvent.

Example 3-1

4-(3-Carboxymethyl-7-fluoro-naphthalen-1-yloxy)-piperidine-1-carboxylic acid tert-butyl ester

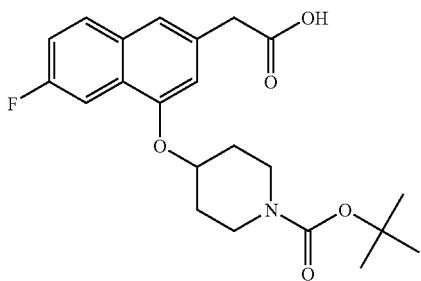

4-(7-Fluoro-3-methoxycarbonylmethyl-naphthalen-1-yloxy)-piperidine-1-carboxylic acid tert-butyl ester

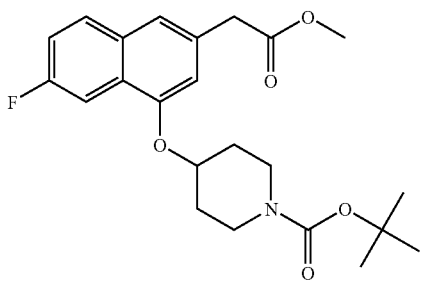

To a solution of (6-fluoro-4-hydroxy-naphthalen-2-yl)-acetic acid methyl ester (500 mg, 2.1 mmol), 4-hydroxy-piperidine-1-carboxylic acid tert-butyl ester (640 mg, 3.2 mmol) and triphenylphosphine (840 mg, 3.2 mmol) in anhydrous tetrahydrofuran (20 ml) was added diethyl azodicarboxylate (0.5 ml, 3.2 mmol) dropwise. After being stirred under an argon atmosphere at room temperature for 4 hours, the mixture was diluted with water (15 mL), and extracted with ethyl acetate (20 mL×2). The combined organic layers were washed with brine (20 mL), dried over sodium sulfate, filtered, and concentrated in vacuo. The residue was purified by column chromatography (elution with 20% ethyl acetate in hexanes) to give 4-(7-fluoro-3-methoxycarbonylmethyl-naphthalen-1-yloxy)-piperidine-1-carboxylic acid tert-butyl ester (740 mg, 84%) as a pale yellow solid.

4-(3-Carboxymethyl-7-fluoro-naphthalen-1-yloxy)-piperidine-1-carboxylic acid tert-butyl ester

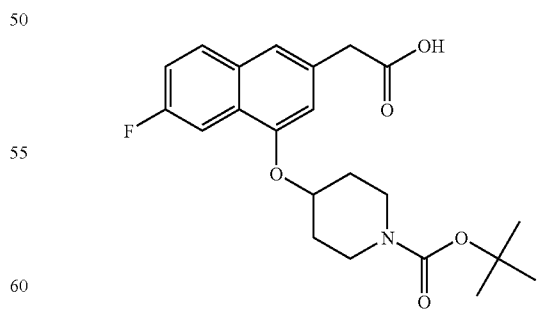

Starting with 4-(7-fluoro-3-methoxycarbonylmethyl-naphthalen-1-yloxy)-piperidine-1-carboxylic acid tert-butyl ester (30 mg, 0.07 mmol), using a method analogous to the one described above for example 1-1, 4-(3-carboxymethyl-7-fluoro-naphthalen-1-yloxy)-piperidine-1-carboxylic acid tert-butyl ester (16 mg, 55%) was obtained as a white solid. $^1$H NMR (400 MHz, CD$_3$OD) δ ppm 7.81 (dd, J=8.97, 5.43 Hz, 1H), 7.77 (dd, J=10.86, 2.53 Hz, 1H), 7.35 (s, 1H), 7.28 (td, J=8.78, 2.65 Hz, 1H), 6.99 (s, 1H), 4.77-4.83 (m, 1H), 3.71-3.81 (m, 4H), 3.39-3.52 (m, 2H) 2.00-2.11 (m, 2H), 1.80-1.90 (m, 2H), 1.47 (s, 9H); MS cald. for C$_{22}$H$_{26}$FNO$_5$ 403, obsd. (ESI$^+$) [(M+H)$^+$] 404.

Example 4-1

[6-Fluoro-4-(1-methanesulfonyl-piperidin-4-yloxy)-naphthalen-2-yl]-acetic acid

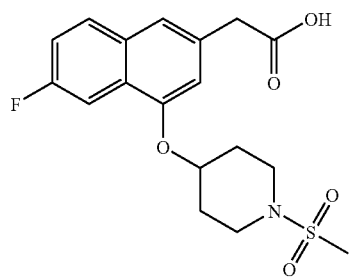

[6-Fluoro-4-(piperidin-4-yloxy)-naphthalen-2-yl] acetic acid methyl ester

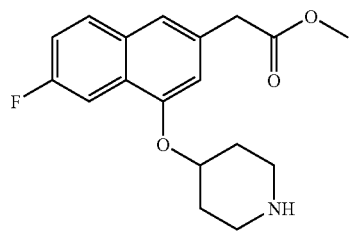

To a solution of 4-(7-fluoro-3-methoxycarbonylmethyl-naphthalen-1-yloxy)-piperidine-1-carboxylic acid tert-butyl ester (prepared as described above, 400 mg, 0.99 mmol) in methanol (4 mL) was added a 5N solution of hydrogen chloride in methanol (4 mL). After being stirred at room temperature for 3 hours, the mixture was concentrated in vacuo. The residue was dissolved in dichloromethane (10 mL), and treated with a saturated aqueous sodium bicarbonate solution (10 mL). The aqueous layer was separated and extracted with dichloromethane (10 mL×2). The combined organic layers were dried over sodium sulfate and concentrated in vacuo. The residue was purified by column chromatography (elution with 10% methanol in dichloromethane) to afford [6-fluoro-4-(piperidin-4-yloxy)-naphthalen-2-yl]-acetic acid methyl ester (260 mg, 85%) as a pale yellow solid.

[6-Fluoro-4-(1-methanesulfonyl-piperidin-4-yloxy)-naphthalen-2-yl]-acetic acid methyl ester

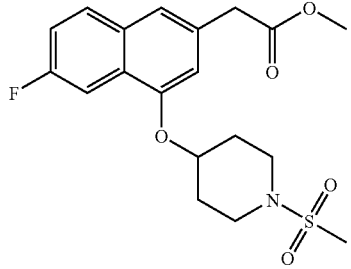

To a solution of [6-fluoro-4-(piperidin-4-yloxy)-naphthalen-2-yl]-acetic acid methyl ester (80 mg, 0.25 mmol) and methanesulfonyl chloride (58 mg, 0.5 mmol) in tetrahydrofuran (2 mL) was added triethylamine (63.6 mg, 0.63 mmol). After being stirred at room temperature overnight, the mixture was concentrated in vacuo. The residue was purified by column chromatography (gradient elution with 10-50% ethyl acetate in petroleum ether) to afford [6-fluoro-4-(1-methanesulfonyl-piperidin-4-yloxy)-naphthalen-2-yl]-acetic acid methyl ester (82 mg, 83%) as a white solid.

[6-Fluoro-4-(1-methanesulfonyl-piperidin-4-yloxy)-naphthalen-2-yl]-acetic acid

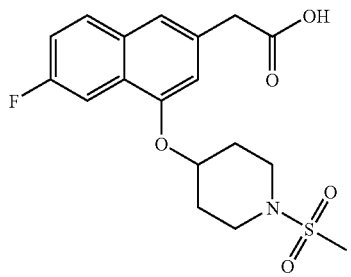

Starting with [6-fluoro-4-(1-methanesulfonyl-piperidin-4-yloxy)-naphthalen-2-yl]-acetic acid methyl ester (20 mg, 0.05 mmol), using a method analogous to the one described above for example 1-1, [6-fluoro-4-(1-methanesulfonyl-piperidin-4-yloxy)-naphthalen-2-yl]-acetic acid (8 mg, 42%) was obtained as a white solid. $^1$H NMR (400 MHz, CDCl$_3$) δ ppm 8.28 (dd, J=9.35, 5.31 Hz, 1H), 7.73-7.84 (m, 1H), 7.35 (s, 1H), 7.28-7.31 (m, 1H), 6.81 (s, 1H), 4.77-4.83 (m, 1H), 3.78 (s, 2H), 3.46-3.53 (m, 2H), 3.35-3.43 (m, 2H), 2.86 (s, 3H), 2.77-2.91 (m, 3H), 2.06-2.21 (m, 4H); MS cald. for C$_{18}$H$_{20}$FNO$_5$S 381, obsd. (ESI$^+$) [(M+H)$^+$] 382.

Examples 4-2 to 4-10

The following examples 4-2 and 4-10 were prepared in an analogous manner to the one described for example 4-1, starting with (6-fluoro-4-hydroxy-naphthalen-2-yl)-acetic acid methyl ester, 4-hydroxy-piperidine-1-carboxylic acid tert-butyl ester, and commercially available sulfonyl chlorides.

| Example No. | Systematic Name | ¹H NMR (400 MHz, CD₃OD) δ ppm | MS (ESI⁺, [(M + H)⁺] | Structure |
|---|---|---|---|---|
| 4-2 | [4-(1-Ethanesulfonyl-piperidin-4-yloxy)-6-fluoro-naphthalen-2-yl]-acetic acid | 7.74-7.83 (m, 2H), 7.36 (s, 1H), 7.26 (td, J = 8.72, 2.53 Hz, 1H), 7.03 (s, 1H), 4.80-4.85 (m, 1H), 3.68 (s, 2H), 3.54-3.62 (m, 2H), 3.10 (q, J = 7.33 Hz, 2H), 2.11-2.21 (m, 2H), 1.99-2.07 (m, 2H), 1.35 (t, J = 7.45 Hz, 3H) | 396 | 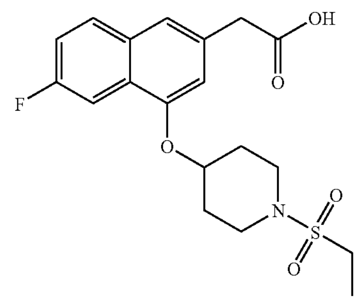 |
| 4-3 | {6-Fluoro-4-[1-(propane-2-sulfonyl)-piperidin-4-yloxy]-naphthalen-2-yl}-acetic acid | 7.81 (dd, J = 8.97, 5.43 Hz, 1H), 7.77 (dd, J = 10.86, 2.53 Hz, 1H), 7.36 (s, 1H), 7.27 (s, 1H), 4.79-4.84 (m, 1H), 3.70 (s, 2H), 3.61-3.69 (m, 2H), 3.39-3.50 (m, 2H), 2.09-2.19 (m, 2H), 1.94-2.04 (m, 2H), 1.34 (d, J = 6.82 Hz, 6H) | 410 | 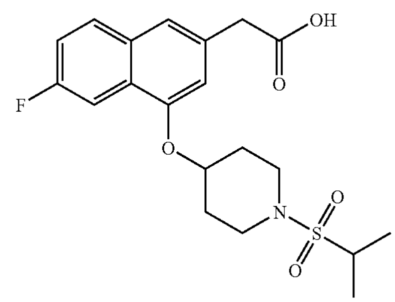 |
| 4-4 | [4-(1-Cyclopropanesulfonyl-piperidin-4-yloxy)-6-fluoro-naphthalen-2-yl]-acetic acid | 7.75-7.86 (m, 2H), 7.37 (s, 1H), 7.29 (td, J = 8.78, 2.65 Hz, 1H), 7.01 (s, 1H), 3.55-3.64 (m, 2H), 3.37-3.46 (m, 2H), 2.52-2.61 (m, 1H), 2.01-2.22 (m, 5H), 1.01-1.14 (m, 3H) | 408 | 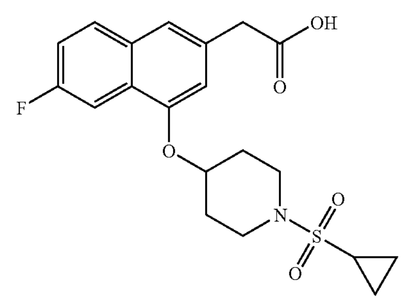 |
| 4-5 | [4-(1-Cyclopentanesulfonyl-piperidin-4-yloxy)-6-fluoro-naphthalen-2-yl]-acetic acid | 7.78-7.86 (m, 2H), 7.31 (td, J = 8.78, 2.65 Hz, 1H), 7.38 (s, 1H), 7.02 (s, 1H), 3.76 (s, 2H), 3.58-3.74 (m, 3H), 3.43 (ddd, J = 12.06, 7.39, 3.79 Hz, 2H), 2.11-2.21 (m, 2H), 1.93-2.11 (m, 7H), 1.75-1.86 (m, 2H), 1.63-1.74 (m, 2H) | 436 | 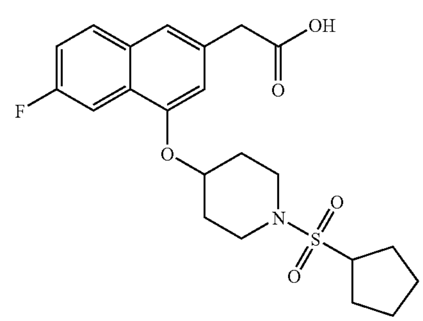 |
| 4-6 | [4-(1-Benzenesulfonyl-piperidin-4-yloxy)-6-fluoro-naphthalen-2-yl]-acetic acid | 7.83 (d, J = 1.52 Hz, 2H), 7.70-7.81 (m, 2H), 7.63-7.70 (m, 2H), 7.39 (dd, J = 10.48, 2.65 Hz, 1H), 7.34 (s, 1H), 7.25 (td, J = 8.72, 2.78 Hz, 1H), 6.94 (s, 1H), 4.71-4.80 (m, 1H), 3.71 (s, 2H), 3.11-3.29 (m, 4H), 1.97-2.24 (m, 4H) | 444 | 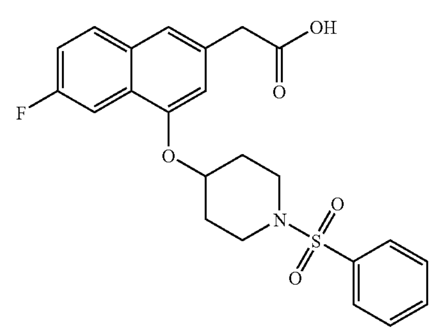 |

| Example No. | Systematic Name | ¹H NMR (400 MHz, CD₃OD) δ ppm | MS (ESI⁺, [(M + H)⁺] | Structure |
|---|---|---|---|---|
| 4-7 | {6-Fluoro-4-[1-(3-fluoro-benzenesulfonyl)-piperidin-4-yloxy]-naphthalen-2-yl}-acetic acid | 7.80 (dd, J = 9.09, 5.56 Hz, 1H), 7.64-7.74 (m, 2H), 7.59 (d, J = 6.32 Hz, 1H), 7.46-7.53 (m, 1H), 7.42 (dd, J = 10.48, 2.65 Hz, 1H), 7.34 (s, 1H), 7.26 (td, J = 8.78, 2.40 Hz, 1H), 6.95 (s, 1H), 4.74-4.81 (m, 1H), 3.72 (s, 2H), 3.14-3.31 (m, 4H), 2.00-2.19 (m, 4H), | 462 | 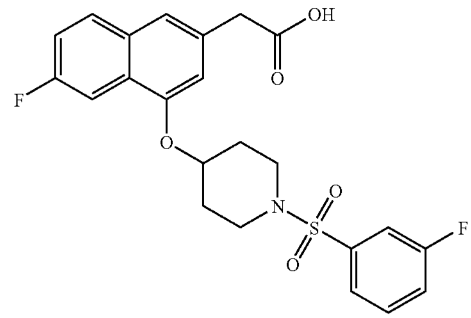 |
| 4-8 | {6-Fluoro-4-[1-(4-fluoro-benzenesulfonyl)-piperidin-4-yloxy]-naphthalen-2-yl}-acetic acid | 7.89 (dd, J = 8.84, 5.05 Hz, 2H), 7.79 (dd, J = 8.97, 5.68 Hz, 1H), 7.37-7.42 (m, 3H), 7.34 (s, 1H), 7.26 (td, J = 8.84, 2.53 Hz, 1H), 6.95 (s, 1H), 4.76-4.81 (m, 1H), 3.71 (s, 2H), 3.14-3.30 (m, 4H), 2.06-2.17 (m, 4H) | 462 | 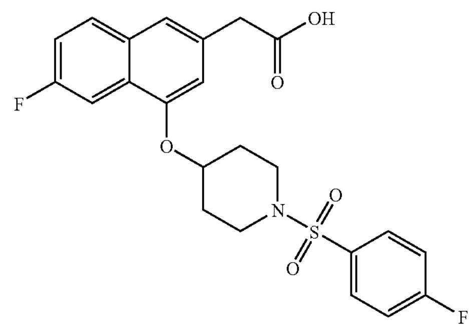 |
| 4-9 | {6-Fluoro-4-[1-(pyridine-3-sulfonyl)-piperidin-4-yloxy]-naphthalen-2-yl}-acetic acid | 8.97 (d, J = 2.02 Hz, 1H), 8.86 (dd, J = 4.93, 1.39 Hz, 1H), 8.22-8.27 (m, 1H), 7.78 (dd, J = 8.84, 5.31 Hz, 1H), 7.70 (dd, J = 8.21, 4.67 Hz, 1H), 7.40 (dd, J = 10.48, 2.91 Hz, 1H), 7.33 (s, 1H), 7.24 (td, J = 8.78, 2.65 Hz, 1H), 6.93 (s, 1H), 4.74-4.80 (m, 1H), 3.71 (s, 2H), 3.14-3.29 (m, 4H), 2.01-2.18 (m, 4H) | 445 | 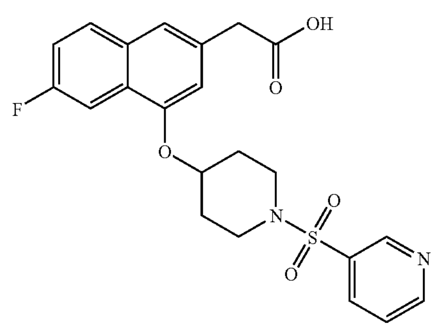 |
| 4-10 | [6-Fluoro-4-(1-phenylmethanesulfonyl-piperidin-4-yloxy)-naphthalen-2-yl]-acetic acid | 7.83 (dd, J = 8.97, 5.94 Hz, 1H), 7.77 (dd, J = 10.48, 2.15 Hz, 1H), 7.50 (d, J = 7.07 Hz, 2H), 7.25-7.45 (m, 5H), 6.94 (s, 1H), 4.78-4.83 (m, 1H), 4.42 (s, 2H), 3.73 (s, 2H), 3.31-3.35 (m, 4H), 1.88-2.02 (m, 4H) | 458 | 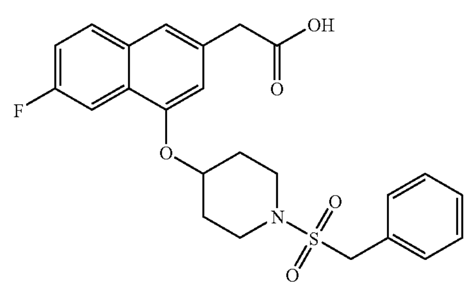 |

Example 5-1

[4-(1-Acetyl-piperidin-4-yloxy)-6-fluoro-naphthalen-2-yl]-acetic acid

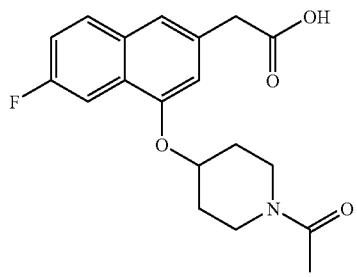

[4-(1-Acetyl-piperidin-4-yloxy)-6-fluoro-naphthalen-2-yl]-acetic acid

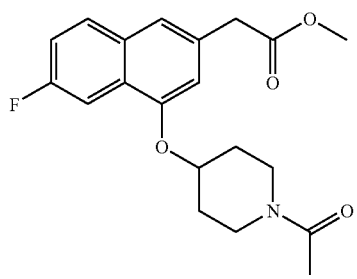

To a solution of [6-fluoro-4-(piperidin-4-yloxy)-naphthalen-2-yl]-acetic acid methyl ester (the intermediate for example 4-1, 1$^{st}$ step, 80 mg, 0.25 mmol) and acetyl chloride (39 mg, 0.5 mmol) in tetrahydrofuran (2 mL) was added a solution of 4-dimethylaminopyridine (76 mg, 0.63 mmol) in tetrahydrofuran (1 mL) dropwise. After being stirred at room temperature overnight, the mixture was concentrated in vacuo. The residue was purified by column chromatography (gradient elution with 10-50% ethyl acetate in petroleum ether) to afford [4-(1-acetyl-piperidin-4-yloxy)-6-fluoro-naphthalen-2-yl]-acetic acid methyl ester (72 mg, 79%) as a white solid.

[4-(1-Acetyl-piperidin-4-yloxy)-6-fluoro-naphthalen-2-yl]-acetic acid

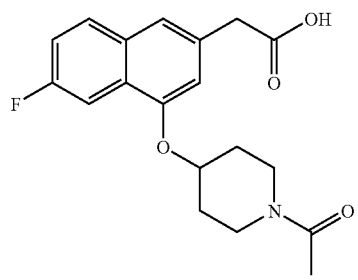

Starting with [4-(1-acetyl-piperidin-4-yloxy)-6-fluoro-naphthalen-2-yl]-acetic acid methyl ester (72 mg, 0.2 mmol), using a method analogous to the one described above for example 1-1, final step, [4-(1-acetyl-piperidin-4-yloxy)-6-fluoro-naphthalen-2-yl]-acetic acid (10.9 mg, 16%) was obtained as a white solid. $^1$H NMR (400 MHz, CD$_3$OD) δ ppm 7.81 (dd, J=8.97, 5.43 Hz, 1H), 7.77 (dd, J=10.86, 2.53 Hz, 1H), 7.27 (td, J=8.78, 2.65 Hz, 1H), 7.03 (s, 1H), 3.77-3.92 (m, 2H), 3.70 (s, 2H), 3.52-3.68 (m, 2H), 2.15 (s, 3H), 2.01-2.14 (m, 2H), 1.83-2.02 (m, 2H); MS cald. for C$_{19}$H$_{20}$FNO$_4$ 345, obsd. (ESI$^+$) [(M+H)$^+$] 346.

Examples 5-2 to 5-10

The following examples 5-2 and 5-10 were prepared in an analogous manner to the one described for example 5-1, starting with [6-fluoro-4-(piperidin-4-yloxy)-naphthalen-2-yl]-acetic acid methyl ester (the intermediate for example 4-1, 1$^{st}$ step) and commercially available sulfonyl chlorides.

| Example No. | Systematic Name | $^1$H NMR (400 MHz, CD$_3$OD) δ ppm | MS (ESI$^+$, [(M + H)$^+$] | Structure |
|---|---|---|---|---|
| 5-2 | [6-Fluoro-4-(1-propionyl-piperidin-4-yloxy)-naphthalen-2-yl]-acetic acid | 7.75-7.84 (m, 2H), 7.36 (s, 1H), 7.28 (td, J = 8.72, 2.78 Hz, 1H), 7.01 (s, 1H), 4.87-4.91 (m, 1H), 3.77-3.92 (m, 2H), 3.75 (s, 2H), 3.53-3.71 (m, 2H), 2.46 (q, J = 7.49 Hz, 2H), 1.82-2.17 (m, 4H), 1.14 (t, J = 7.45 Hz, 3H) | 360 | 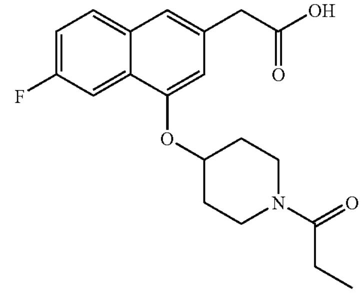 |

-continued

| Example No. | Systematic Name | ¹H NMR (400 MHz, CD$_3$OD) δ ppm | MS (ESI⁺, [(M + H)⁺] | Structure |
|---|---|---|---|---|
| 5-3 | [6-Fluoro-4-(1-isobutyryl-piperidin-4-yloxy)-naphthalen-2-yl]-acetic acid | 7.75-7.84 (m, 2H), 7.36 (s, 1H), 7.28 (td, J = 8.72, 2.78 Hz, 1H), 7.01 (s, 1H), 4.88-4.93 (m, 1H), 3.83-3.92 (m, 2H), 3.75 (s, 2H), 3.58-3.70 (m, 2H), 3.00 (ddd, J = 13.52, 6.69, 6.57 Hz, 1H), 1.81-2.18 (m, 4H), 1.12 (d, J = 6.57 Hz, 6H) | 374 | 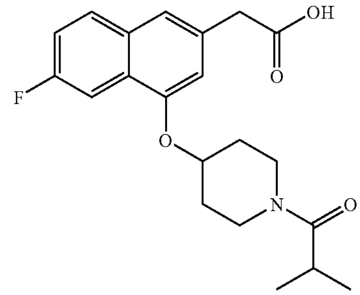 |
| 5-4 | [4-(1-Cyclopropanecarbonyl-piperidin-4-yloxy)-6-fluoro-naphthalen-2-yl]-acetic acid | 7.79-7.86 (m, 2H), 7.38 (s, 1H), 7.30 (td, J = 8.72, 2.53 Hz, 1H), 7.04 (s, 1H), 4.92 (dt, J = 7.01, 3.44 Hz, 1H), 3.79-4.14 (m, 3H), 3.77 (s, 2H), 3.61-3.73 (m, 1H), 1.83-2.25 (m, 5H), 0.69-0.99 (m, 4H) | 372 | 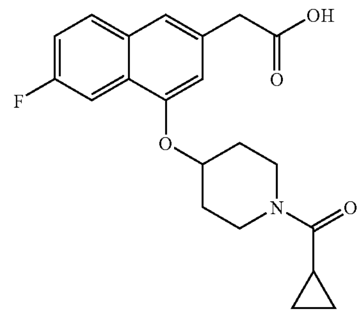 |
| 5-5 | [4-(1-Cyclopentanecarbonyl-piperidin-4-yloxy)-6-fluoro-naphthalen-2-yl]-acetic acid | 7.75-7.84 (m, 2H), 7.36 (s, 1H), 7.28 (td, J = 8.72, 2.78 Hz, 1H), 7.01 (s, 1H), 4.87-4.92 (m, 1H), 3.84-3.94 (m, 2H), 3.75 (s, 2H), 3.60-3.71 (m, 2H), 3.04-3.16 (m, 1H), 1.55-2.18 (m, 12H) | 400 | 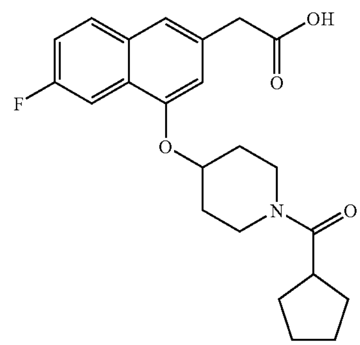 |
| 5-6 | [4-(1-Benzoyl-piperidin-4-yloxy)-6-fluoro-naphthalen-2-yl]-acetic acid | 7.80-7.85 (m, 2H), 7.45-7.52 (m, 5H), 7.38 (s, 1H), 7.30 (td, J = 8.65, 2.65 Hz, 1H), 7.02 (s, 1H), 4.91-4.97 (m, 1H), 3.41-4.11 (m, 6H), 1.84-2.26 (m, 4H) | 408 | 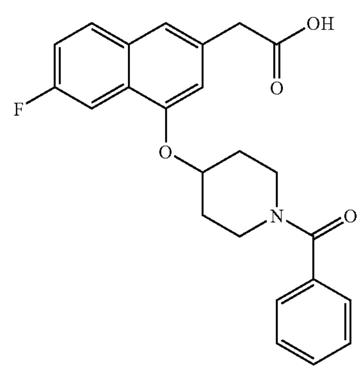 |

| Example No. | Systematic Name | ¹H NMR (400 MHz, CD₃OD) δ ppm | MS (ESI⁺, [(M + H)⁺] | Structure |
|---|---|---|---|---|
| 5-7 | {6-Fluoro-4-[1-(2-fluoro-benzoyl)-piperidin-4-yloxy]-naphthalen-2-yl}-acetic acid | 7.75-7.84 (m, 2H), 7.46-7.54 (m, 1H), 7.40-7.46 (m, 1H), 7.36 (s, 1H), 7.18-7.32 (m, 3H), 7.01 (s, 1H), 4.89-4.96 (m, 1H), 3.82-4.09 (m, 2H), 3.74 (s, 2H), 3.35-3.69 (m, 2H), 1.81-2.24 (m, 4H) | 426 | 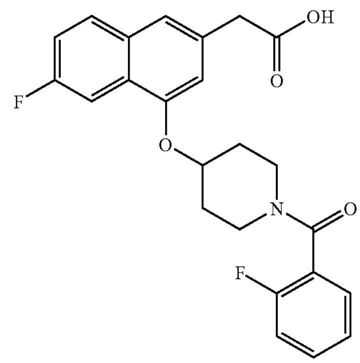 |
| 5-8 | {6-Fluoro-4-[1-(3-fluoro-benzoyl)-piperidin-4-yloxy]-naphthalen-2-yl}-acetic acid | 7.79-7.86 (m, 2H), 7.48-7.55 (m, 1H), 7.38 (s, 1H), 7.21-7.33 (m, 4H), 7.02 (s, 1H), 4.94 (td, J = 6.76, 3.41 Hz, 1H), 3.82-4.06 (m, 2H), 3.67-3.79 (m, 3H), 3.40-3.58 (m, 2H), 1.84-2.30 (m, 4H) | 426 | 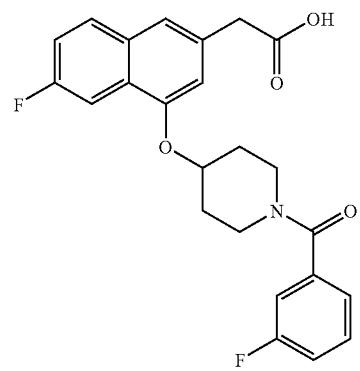 |
| 5-9 | {6-Fluoro-4-[1-(4-fluoro-benzoyl)-piperidin-4-yloxy]-naphthalen-2-yl}-acetic acid | 7.80-7.86 (m, 2H), 7.52-7.57 (m, 2H), 7.38 (s, 1H), 7.30 (td, J = 8.72, 2.53 Hz, 1H), 7.19-7.26 (m, 2H), 7.03 (s, 1H), 3.42-4.12 (m, 6H), 1.84-2.29 (m, 4H) | 426 | 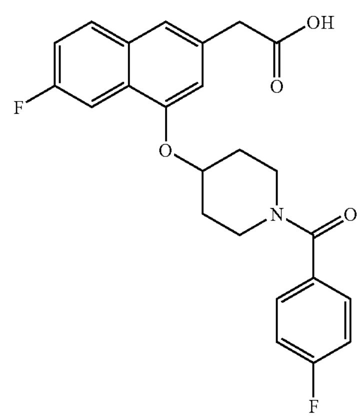 |
| 5-10 | [6-Fluoro-4-(1-phenylacetyl-piperidin-4-yloxy)-naphthalen-2-yl]-acetic acid | 7.82 (dd, J = 8.97, 5.68 Hz, 1H), 7.75 (dd, J = 10.74, 2.65 Hz, 1H), 7.23-7.39 (m, 7H), 6.97 (s, 1H), 4.79-4.84 (m, 1H), 3.78-3.94 (m, 4H), 3.74 (s, 2H), 3.53-3.73 (m, 2H), 1.63-2.10 (m, 4H) | 422 | 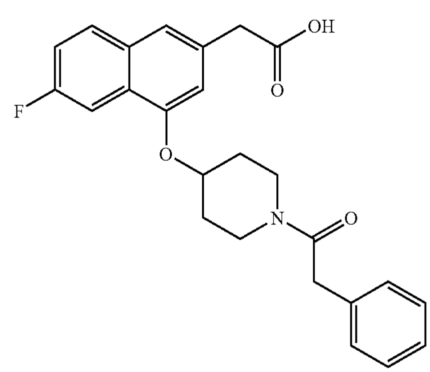 |

Example 6-1

[4-(1-Ethylcarbamoyl-piperidin-4-yloxy)-6-fluoro-naphthalen-2-yl]-acetic acid

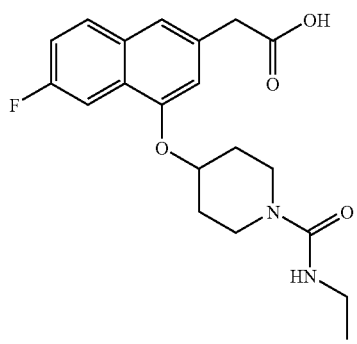

[4-(1-Ethylcarbamoyl-piperidin-4-yloxy)-6-fluoro-naphthalen-2-yl]-acetic acid methyl ester

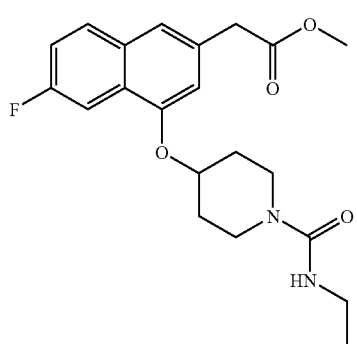

A mixture of [6-fluoro-4-(piperidin-4-yloxy)-naphthalen-2-yl]-acetic acid methyl ester (the intermediate for example 4-1, 1$^{st}$ step, 20 mg, 0.063 mmol) and isocyanato-ethane (0.05 mL) and dichloromethane was stirred at room temperature for 4 hours. The resulting mixture was concentrated in vacuo. The residue was purified by flash column (gradient elution with 0-30% ethyl acetate in petroleum ether) to afford [4-(1-ethylcarbamoyl-piperidin-4-yloxy)-6-fluoro-naphthalen-2-yl]-acetic acid methyl ester (21.0 mg, 85%) as a viscous oil.

[4-(1-Ethylcarbamoyl-piperidin-4-yloxy)-6-fluoro-naphthalen-2-yl]-acetic acid

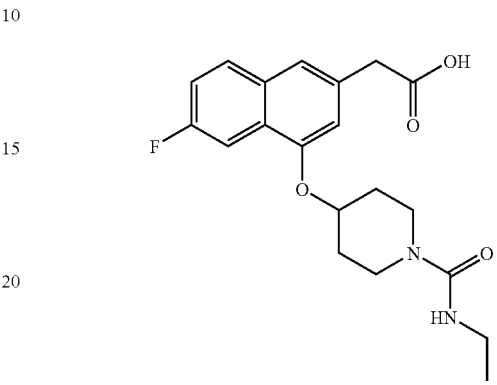

Starting with [4-(1-ethylcarbamoyl-piperidin-4-yloxy)-6-fluoro-naphthalen-2-yl]-acetic acid methyl ester (21 mg, 0.054 mmol), using a method analogous to the one described above for example 1-1, final step, [4-(1-ethylcarbamoyl-piperidin-4-yloxy)-6-fluoro-naphthalen-2-yl]-acetic acid (1.2 mg) was obtained as a light-brown powder. $^1$H NMR (400 MHz, CD$_3$OD) δ ppm 7.83 (dd, J=9.09, 5.81 Hz, 1H), 7.79 (dd, J=10.74, 2.65 Hz, 1H), 7.37 (s, 1H), 7.30 (td, J=8.72, 2.78 Hz, 1H), 7.02 (s, 1H), 4.83-4.85 (m, 1H), 3.70-3.79 (m, 4H), 3.38-3.46 (m, 2H), 3.23 (q, J=7.07 Hz, 2H), 2.05-2.14 (m, 2H), 1.83-1.93 (m, 2H), 1.15 (t, J=7.20 Hz, 3H); MS cald. for C$_{20}$H$_{23}$FN$_2$O$_4$ 374, obsd. (ESI$^+$) [(M+H)$^+$] 375.

Examples 6-2 to 6-5

The following examples 6-2 and 6-5 were prepared in an analogous manner to the one described for example 6-1, starting with [6-fluoro-4-(piperidin-4-yloxy)-naphthalen-2-yl]-acetic acid methyl ester (the intermediate for example 4-1, 1$^{st}$ step) and commercially available isocyanates.

| Example No. | Systematic Name | $^1$H NMR (400 MHz, CD$_3$OD) δ ppm | MS (ESI$^+$, [(M + H)$^+$] | Structure |
| --- | --- | --- | --- | --- |
| 6-2 | {6-Fluoro-4-[1-(2-fluoro-phenylcarbomoyl)-piperidin-4-yloxy]-naphthalen-2-yl}-acetic acid | 7.77-7.84 (m, 2H), 7.43-7.49 (m, 1H), 7.37 (s, 1H), 7.28 (td, J = 8.72, 2.53 Hz, 1H), 7.09-7.15 (m, 3H), 7.04 (s, 1H), 4.87-4.94 (m, 1H), 3.83-3.92 (m, 2H), 3.73 (s, 2H), 3.54-3.64 (m, 2H), 2.11-2.21 (m, 2H), 1.91-2.04 (m, 2H) | 441 | 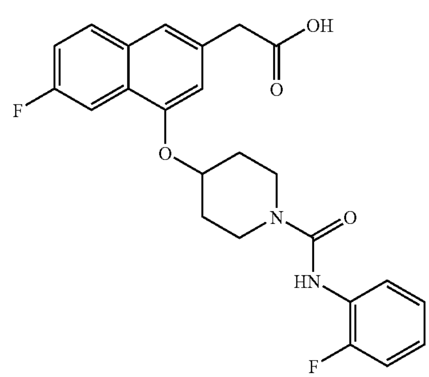 |

-continued

| Example No. | Systematic Name | $^1$H NMR (400 MHz, CD$_3$OD) δ ppm | MS (ESI$^+$, [(M + H)$^+$] | Structure |
| --- | --- | --- | --- | --- |
| 6-3 | {6-Fluoro-4-[1-(3-fluoro-phenylcarbamoyl)-piperidin-4-yloxy]-naphthalen-2-yl}-acetic acid | 7.76-7.85 (m, 2H), 7.37 (s, 1H), 7.20-7.32 (m, 3H), 7.16 (d, J = 1.01 Hz, 1H), 7.03 (s, 1H), 6.72 (td, J = 8.53, 1.89 Hz, 1H), 4.87-4.91 (m, 1H), 3.83-3.91 (m, 2H), 3.72 (s, 0H), 3.54-3.63 (m, 2H), 1.89-2.23 (m, 4H) | 441 | 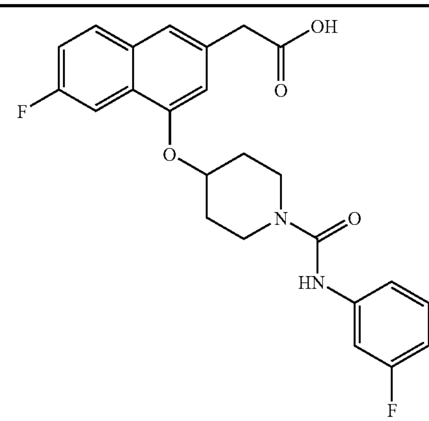 |
| 6-4 | {6-Fluoro-4-[1-(4-fluoro-phenylcarbamoyl)-piperidin-4-yloxy]-naphthalen-2-yl}-acetic acid | 6.27-6.36 (m, 2H), 5.83-5.88 (m, 3H), 5.79 (td, J = 8.78, 2.15 Hz, 1H), 5.47-5.55 (m, 3H), 3.39-3.44 (m, 1H), 2.32-2.41 (m, 2H), 2.25 (s, 2H), 2.03-2.12 (m, 2H), 0.39-0.71 (m, 4H), | 441 | 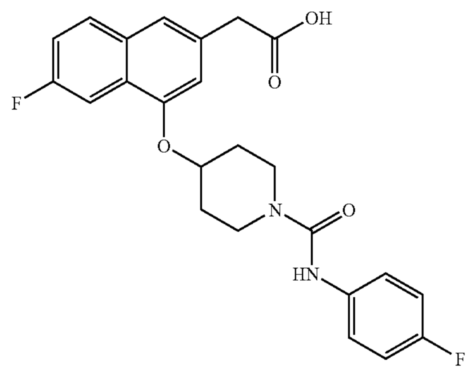 |
| 6-5 | [6-Fluoro-4-(1-phenethylcarbamoyl-piperidin-4-yloxy)-naphthalen-2-yl]-acetic acid | 6.32 (dd, J = 8.97, 5.68 Hz, 1H), 6.27 (dd, J = 10.74, 2.65 Hz, 1H), 5.86 (s, 1H), 5.65-5.82 (m, 6H), 5.50 (s, 1H), 3.28-3.33 (m, 1H), 2.25 (s, 2H), 2.17-2.24 (m, 2H), 1.84-1.92 (m, 4H), 1.32 (t, J = 7.33 Hz, 2H), 0.49-0.61 (m, 2H), 0.25-0.40 (m, 2H) | 451 | 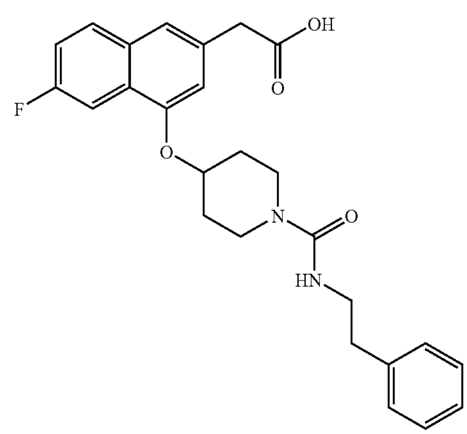 |

Activity and Use of the Compounds

The compounds of formula I and Z possess valuable pharmacological properties. It has been found that said compounds are antagonists or partial agonists at the CRTH2 receptor and may be useful in treating diseases and disorders associated with that receptor such as asthma. The activity of the present compounds as CRTH2 receptor antagonists or partial agonists is demonstrated by the following biological assays.

Human CRTH2 Receptor Binding Assay

A whole cell receptor binding assay using [$^3$H]ramatroban as the competing radioactive ligand was employed to evaluate the compound binding activity to human CRTH2. The radioactive ligand [$^3$H]ramatroban was synthesized according to Sugimoto et. al. (*Eur. J. Pharmacol.* 524, 30-37, 2005) to a specific activity of 42 Ci/mmol.

A cell line stably expressing human CRTH2 was established by transfecting CHO-K1 cells with two mammalian expression vectors that harbored human CRTH2 and G-alpha16 cDNAs, respectively, using FuGene® 6 transfection reagent (from Roche). Stable clones expressing CRTH2 were selected by staining each clone with BM16 (BD Pharmingen™ from BD Biosciences, a division of Becton, Dickinson and Company), which is a rat monoclonal antibody to human CRTH2. The cells were maintained as monolayer cultures in Ham's F-12 medium containing 10% fetal bovine serum, 100 units/mL penicillin, 100 µg/mL streptomycin, 2 mM glutamine, 0.5 mg/mL G418 (geneticin) for CRTH2, and 0.2 mg/mL hygromycin-B (for G-alpha 16). For whole cell receptor binding assay, the monolayer cells were rinsed once with PBS (phosphate buffered saline), dissociated using ethylenediaminetetraacetate (Versene™ EDTA from Lonza Inc.), and suspended in PBS containing 10 mM $MgCl_2$ and 0.06% BSA (bovine serum albumin) at $1.5 \times 10^6$ cells/mL.

The binding reactions (0.2 mL) were performed in 96-well plates at room temperature in PBS containing $1.5 \times 10^5$ cells, 10 mM $MgCl_2$, 0.06% BSA, 20 nM [$^3$H]ramatroban, and test compound at various concentrations. After 1 hour of binding reactions, the cells were harvested on GF™/B filter microplates (microtiter plates with embedded glass fiber from PerkinElmer, Inc.) and washed 5 times with PBS using a Filtermate™ Harvester (a cell harvester that harvests and washes cells from microplates from PerkinElmer, Inc.). The radioactivities bound to the cells were determined using a microplate scintillation counter (TopCount® NXT, from PerkinElmer, Inc.) after adding 50 µL of Microscint™ 20 scintillation fluid (from PerkinElmer, Inc.) to each well of the filter plates. The radioactivity from non-specific binding was determined by replacing compound with 10 µM of 15(R)-15-methyl $PGD_2$ (from Cayman Chemical Company) in the reaction mixtures. The radioactivity bound to the cells in the absence of compound (total binding) was determined by replacing compound with 0.25% of DMSO (dimethyl sulfoxide) in the reaction mixture. Specific binding data were obtained by subtracting the radioactivity of non-specific binding from each binding data.

The $IC_{50}$ value is defined as the concentration of the tested compound that is required for 50% inhibition of total specific binding. In order to calculate the $IC_{50}$ value, the percent inhibition data were determined for 7 concentrations for each compound. The percent inhibition for a compound at each concentration was calculated according to the following formula, [1−(specific binding in the presence of compound)/(total specific binding)]×100. The $IC_{50}$ value was then obtained by fitting the percent inhibition data to a sigmoidal dose-response (4 parameter logistic) model in the XLfit® software Excel add-in program [from ID Business Solutions Ltd., model 205, where $F(x)=(A+(B-A)/(1+((C/x)^D)))$].

Certain compounds of the foregoing examples were tested using the above Human CRTH2 Receptor Binding Assay. The results of the assay showed that all of the compounds tested have binding activity exhibiting $IC_{50}$ values ranging from 0.0017 µM to 0.4575 µM as shown below:

| Example No. | Human CRTH2 Binding $IC_{50}$ (µM) |
|---|---|
| Example 1-1 | 0.0192 |
| Example 1-2 | 0.0072 |
| Example 1-3 | 0.0212 |
| Example 1-4 | 0.0155 |
| Example 1-5 | 0.0076 |
| Example 1-6 | 0.0091 |
| Example 1-7 | 0.0065 |
| Example 1-8 | 0.0069 |
| Example 1-9 | 0.0037 |
| Example 1-10 | 0.2072 |
| Example 1-11 | 0.0883 |
| Example 1-12 | 0.0083 |
| Example 1-13 | 0.0054 |
| Example 1-14 | 0.0048 |
| Example 1-15 | 0.0026 |
| Example 1-16 | 0.0031 |
| Example 1-17 | 0.0037 |

-continued

| Example No. | Human CRTH2 Binding $IC_{50}$ (µM) |
|---|---|
| Example 1-18 | 0.006 |
| Example 1-19 | 0.0017 |
| Example 2-1 | 0.0182 |
| Example 2-2 | 0.0026 |
| Example 2-3 | 0.1506 |
| Example 2-4 | 0.0591 |
| Example 2-5 | 0.2765 |
| Example 2-6 | 0.0815 |
| Example 2-7 | 0.0571 |
| Example 2-8 | 0.4575 |
| Example 2-9 | 0.0631 |
| Example 2-10 | 0.4503 |
| Example 2-11 | 0.2009 |
| Example 2-12 | 0.1061 |
| Example 2-13 | 0.139 |
| Example 2-14 | 0.0657 |
| Example 2-15 | 0.2527 |
| Example 2-16 | 0.0268 |
| Example 2-17 | 0.0219 |
| Example 2-18 | 0.0094 |
| Example 2-19 | 0.01 |
| Example 2-20 | 0.1268 |
| Example 2-21 | 0.0189 |
| Example 2-22 | 0.0112 |
| Example 2-23 | 0.0635 |
| Example 2-24 | 0.022 |
| Example 3-1 | 0.0451 |
| Example 4-1 | 0.0093 |
| Example 4-2 | 0.0203 |
| Example 4-3 | 0.0305 |
| Example 4-4 | 0.0254 |
| Example 4-5 | 0.0099 |
| Example 4-6 | 0.0032 |
| Example 4-7 | 0.005 |
| Example 4-8 | 0.0024 |
| Example 4-9 | N/A |
| Example 4-10 | 0.0027 |
| Example 5-1 | 0.1632 |
| Example 5-2 | 0.1205 |
| Example 5-3 | 0.141 |
| Example 5-4 | 0.0678 |
| Example 5-5 | 0.0533 |
| Example 5-6 | 0.0134 |
| Example 5-7 | 0.0194 |
| Example 5-8 | 0.0298 |
| Example 5-9 | 0.0313 |
| Example 5-10 | 0.0029 |
| Example 6-1 | 0.0245 |
| Example 6-2 | 0.0043 |
| Example 6-3 | 0.003 |
| Example 6-4 | 0.005 |
| Example 6-5 | 0.004 |

Calcium Flux Assay Using Fluorometric Imaging Plate Reader

Cell Culture Conditions:

CHO-K1 cells previously transfected with G-alpha 16 were subsequently transfected with the human CRTH2 receptor and the neomycin resistance gene. Following selection in 800 µg/mL G418 (geneticin), individual clones were assayed for their receptor expression based on staining with an anti human CRTH2 IgG, followed by assaying for their response to 13,14-dihydro-15-keto Prostaglandin $D_2$ (DK-$PDG_2$) (ligand) in the $Ca^{2+}$Flux assay. Positive clones were then cloned by limiting dilution cloning. The transfected cells were cultured in Ham's F-12 medium supplemented with 10% fetal bovine serum, 2 mM glutamine, 100 U/mL penicillin/100 µg/mL streptomycin, 200 µg/mL hygromycin B, and 800 µg/mL G418 (geneticin). Cells were harvested with trypsin-EDTA (trypsin-ethylenediaminetetraacetic acid) and counted using ViaCount® reagent (from Guava Technologies, Inc. which contains two DNA-binding dyes that enable the reagent user to distinguish between viable and non-viable cells). The cell suspension volume was adjusted to $2.5\times10^5$ cells/mL with complete growth media. Aliquots of 50 μL were dispensed into BD Falcon™ 384 well black/clear microplates (from BD Biosciences, a division of Becton, Dickinson and Company) and the microplates were placed in a 37° C. $CO_2$ incubator overnight. The following day, the microplates were used in the assay.

Dye Loading and Assay:

Loading Buffer containing dye (from the FLIPR® Calcium 3 Assay Kit from Molecular Devices, a division of MDS Analytical Technologies and MDS Inc.) was prepared by dissolving the contents of one bottle into 200 mL Hank's Balanced Salt Solution containing 20 mM HEPES (4-(2-hydroxyethyl)-1-piperazineethanesulfonic acid) and 2.5 mM probenecid. Growth media was removed from the cell plates and 25 μL of Hank's Balanced Salt Solution (HBSS) containing 20 mM HEPES, 0.05% BSA and 2.5 mM probenecid was added to each well followed by 25 μL of diluted dye using a Multidrop dispenser. The plates were then incubated for 1 hour at 37° C.

During the incubation, test compound plates were prepared by adding 90 μL of HBSS/20 mM HEPES/0.005% BSA buffer to the 2 μL of serial diluted compounds. To prepare serial diluted compounds, 20 mM stocks of compounds were dissolved in 100% DMSO. The compound dilution plate was set up as follows: well #1 received 5 μL of compound plus 10 μL of DMSO. Wells 2-10 received 10 μL of DMSO. 5 μL was mixed and transferred from well #1 into well #2. 1:3 serial dilutions were continued out 10 steps. 2 μL of diluted compound was transferred into duplicate wells of a 384 well "assay plate" and then 90 μL of buffer was added.

After incubation, both the cell and "assay plate" plates were brought to the fluorometric imaging plate reader (FLIPR®) and 20 μL of the diluted compounds were transferred to the cell plates by the FLIPR®. Plates were then incubated for 1 hour at room temperature. After the 1 hour incubation, plates were returned to the FLIPR® and 20 μL of 4.5× concentrated ligand was added to the cell plates. During the assay, fluorescence readings were taken simultaneously from all 384 wells of the cell plate every 1.5 seconds. Five readings were taken to establish a stable baseline, then 20 μL of sample was rapidly (30 μL/sec) and simultaneously added to each well of the cell plate. The fluorescence was continuously monitored before, during and after sample addition for a total elapsed time of 100 seconds. Responses (increase in peak fluorescence) in each well following agonist addition were determined. The initial fluorescence reading from each well, prior to ligand stimulation, was used as a zero baseline value for the data from that well. The responses were expressed as % inhibition of the buffer control. The $IC_{50}$ value, defined as the concentration of a compound that was required for 50% inhibition of the buffer control, was calculated by fitting the percent inhibition data for 10 concentrations to a sigmoidal dose-response (4 parameter logistic) model using Genedata Screener® Condoseo software program [from Genedata AG, model 205, where $F(x)=(A+(B-A)/(1+((C/x)^D)))$].

Representative compounds tested in the binding assay were tested using the above FLIPR® assay (specifically examples 1-1 to 1-19, 2-1 to 2-24, 3-1, 4-1, 4-2, 4-4, 4-6 to 4-10, 5-1, and 5-3 to 5-10 were tested). The results of the FLIPR® assay showed that (with the exception of examples 2-8, 2-10, 2-15, 4-2 and 5-1 which exhibited $IC_{50}$ values of >5 μM, these compounds exhibited $IC_{50}$ values ranging from 0.0002 μM to 3.770 μM.

$DK-PGD_2$-Induced IL-13 Production Assay in Th2 Cells

Inhibition of 13,14-dihydro-15-keto Prostaglandin $D_2$ ($DK-PGD_2$)-induced IL-13 production in T helper type 2 (Th2) cells was applied to evaluate compound cellular potency.

Cultures of Th2 cells were established from blood of healthy human volunteers according to the following procedure. Peripheral blood mononuclear cells (PBMC) were first isolated from 50 mL of fresh blood by Ficoll-Hypaque density gradient centrifugation, followed by $CD4^+$ cell purification using a $CD4^+$ T Cell Isolation Kit II (from Miltenyi Biotec Inc.). The $CD4^+$ T cells were then differentiated to Th2 cells by culturing the cells in X-VIVO 15® medium (from Cambrex BioScience Walkersville Inc.) containing 10% human AB serum (serum of blood type AB from Invitrogen Corporation), 50 U/mL of recombinant human interleukin-2 (rhIL-2) (from PeproTech Inc.) and 100 ng/mL of recombinant human interleukin-4 (rhIL-4) (from PeproTech Inc.) for 7 days. The Th2 cells were isolated using a CD294 (CRTH2) MicroBead Kit (from Miltenyi Biotec Inc.) and amplified in X-VIVO 15® medium containing 10% human AB serum and 50 U/mL of rhIL-2 for 2 to 5 weeks. In general, 70% to 80% of the Th2 cells used in the assay are CRTH2-positive when analyzed by fluorescence-activated cell sorting using the BM16 antibody (as previously described) conjugated to phycoerythrin (PE).

To determine cellular inhibitory potency, compounds at various concentrations were incubated with $2.5\times10^4$ Th2 cells and 500 nM $DK-PGD_2$ for 4 hrs at 37° C. in 200 μL of X-VIVO 15® medium containing 10% human AB serum. IL-13 production to the medium was detected by ELISA (enzyme-linked immunosorbent assay) using an "Instant ELISA™" kit (from Bender MedSystems Inc.) according to the procedure suggested by the vendor. The spontaneous production of IL-13 by Th2 cells was determined in the absence of DK-PGD2 stimulation and the value was subtracted from that in the presence of each compound for percent inhibition and $IC_{50}$ calculations.

The percent inhibition of interleukin 13 (IL-13) production for a compound at various concentrations was calculated according to the following formula, [1-(IL-13 production in the presence of compound)/(IL-13 production in the presence of 0.15% DMSO)]×100. The $IC_{50}$ value, defined as the concentration of a compound that is required for 50% inhibition of IL-13 production, was calculated by fitting the percent inhibition data for 7 concentrations to a sigmoidal dose-response (4 parameter logistic) model in the XLfit® software Excel add-in program [ID Business Solutions Ltd., model 205, where $F(x)=(A+(B-A)/(1+((C/x)^D)))$].

Representative compounds tested in the binding assay were tested using the foregoing $DK-PGD_2$-induced IL-13 production assay (specifically examples 1-1, 1-2, 1-4 to 1-9, 1-12 to 1-17, 2-2, 2-18, 2-19, 2-22, 4-1 to 4-3, 4-6 to 4-8, 4-10, 5-1, and 5-10 were tested). The results of the $DK-PGD_2$-induced IL-13 production assay showed that these compounds exhibited activity in inhibiting IL-13 production, with $IC_{50}$ values ranging from 0.0024 μM to 3.6007 μM.

Thus, the compounds of the present invention are useful since the compounds tested show some activity in at least one of the above three assays (i.e., binding at the CRTH2 receptor), and therefore may be useful as antagonists or partial agonists in treating diseases and disorders associated with this receptor such as asthma.

In one embodiment, the present invention relates to a method for the treatment and/or prevention of diseases and disorders which are associated with the modulation of CRTH2 receptors, which method comprises administering a therapeutically effective amount of a compound of formula I or Z to a human being or animal. A method for the treatment and/or prevention of an inflammatory or allergic disease or disorder is preferred. Such diseases or disorders may include (but are not limited to) asthma, chronic obstructive pulmonary disease (COPD), allergic rhinitis, allergic inflammation, and atopic dermatitis.

The present invention is also directed to the administration of a therapeutically effective amount of a compound of formula I or Z in combination or association with other drugs or active agents for the treatment of inflammatory or allergic diseases and disorders. In one embodiment, the present invention relates to a method for the treatment and/or prevention of such diseases or disorders comprising administering to a human or animal simultaneously, sequentially, or separately, a therapeutically effective amount of a compound of formula I or Z and another drug or active agent (such as another anti-inflammatory or anti-allergic drug or agent). These other drugs or active agents may have the same, similar, or a completely different mode of action. Suitable other drugs or active agents may include, but are not limited to: Beta2-adrenergic agonists such as albuterol or salmeterol; corticosteroids such as dexamethasone or fluticasone; antihistamines such as loratidine; leukotriene antagonists such as montelukast or zafirlukast; anti-IgE antibody therapies such as omalizumab; anti-infectives such as fusidic acid (particularly for the treatment of atopic dermatitis); anti-fungals such as clotrimazole (particularly for the treatment of atopic dermatitis); immunosuppressants such as tacrolimus and pimecrolimus; other antagonists of PGD2 acting at other receptors such as DP antagonists; inhibitors of phosphodiesterase type 4 such as cilomilast; drugs that modulate cytokine production such as inhibitors of TNF-alpha converting enzyme (TACE); drugs that modulate the activity of Th2 cytokines IL-4 and IL-5 such as blocking monoclonal antibodies and soluble receptors; PPAR-gamma agonists such as rosiglitazone; and 5-lipoxygenase inhibitors such as zileuton.

Unless stated to the contrary, all compounds in the examples were prepared and characterized as described. All patents and publications cited herein are hereby incorporated by reference in their entirety.

The invention claimed is:
1. A compound of formula I:

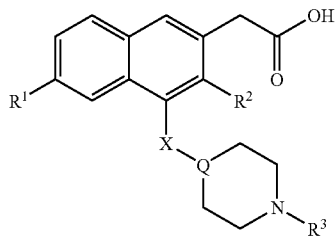

I or a pharmaceutically acceptable salt or ester thereof, wherein:
X is O and Q is C(H); or alternatively, X is C(O) and Q is N;
$R^1$ is selected from the group consisting of:
 (a) hydrogen,
 (b) halogen,
 (c) lower alkyl optionally substituted by fluoro,
 (d) lower alkoxy optionally substituted by fluoro,
 (e) lower alkylsulfonyl, and
 (f) cyano;
$R^2$ is hydrogen or lower alkyl; and
$R^3$ is selected from the group consisting of:
 (a) phenyl, pyridinyl, or pyrimidinyl, wherein said phenyl, pyridinyl, or pyrimidinyl is optionally substituted by one or more substituents independently selected from the group consisting of: (1) halogen, (2) lower alkyl optionally substituted by fluoro; (3) lower alkoxy optionally substituted by fluoro, and (4) cyano;
 (b) lower alkoxycarbonyl; and
 (c) $S(O)_2$—$R^4$, $C(O)$—$R^4$, or $C(O)$—N(H)—$R^4$ wherein $R^4$ is selected from the group consisting of:
  (1) lower alkyl optionally substituted by fluoro,
  (2) lower cycloalkyl,
  (3) phenyl optionally substituted by: (i) halogen or (ii) lower alkyl optionally substituted by fluoro,
  (4) benzyl or phenylethyl, and
  (5) pyridinyl.

2. A compound of claim 1 wherein X is O and Q is C(H).
3. A compound of claim 1 wherein X is C(O) and Q is N.
4. A compound of claim 1 wherein $R^1$ is hydrogen, halogen, or methyl.
5. A compound of claim 1 wherein $R^1$ is fluoro.
6. A compound of claim 1 wherein $R^2$ is hydrogen.
7. A compound of claim 1 wherein $R^2$ is methyl.
8. A compound of claim 1 wherein $R^3$ is phenyl, pyridinyl, or pyrimidinyl.
9. A compound of claim 1 wherein $R^3$ is phenyl.
10. A compound of claim 1 wherein $R^3$ is phenyl substituted with one or two substituents independently selected from the group consisting of chloro, fluoro, methyl, trifluoromethyl, and methoxy.
11. A compound of claim 1 wherein $R^3$ is phenyl substituted at the 4 position on the phenyl ring with chloro, fluoro, methyl, trifluoromethyl, or methoxy.
12. A compound of claim 1 wherein $R^3$ is —$S(O)_2$—$R^4$ and $R^4$ is methyl, ethyl, propyl, isopropyl, cyclopropyl, cyclopentyl, or trifluoromethyl.
13. A compound of claim 1 wherein $R^3$ is —$S(O)_2$—$R^4$ and $R^4$ is phenyl optionally substituted by halogen or lower alkyl optionally substituted with fluoro.
14. A compound of claim 1 wherein $R^3$ is —$S(O)_2$—$R^4$ and $R^4$ is phenyl optionally substituted once or twice by fluoro.
15. A compound of claim 1 wherein $R^3$ is —$C(O)$—$R^4$ and $R^4$ is methyl, ethyl, propyl, isopropyl, cyclopropyl, cyclopentyl, or trifluoromethyl.
16. A compound of claim 1 wherein $R^3$ is —$C(O)$—$R^4$ and $R^4$ is phenyl optionally substituted by halogen or lower alkyl.
17. A compound of claim 1 wherein $R^3$ is —$C(O)$—$R^4$ and $R^4$ is phenyl optionally substituted once or twice by fluoro.
18. A compound of claim 1 wherein $R^3$ is —$C(O)$—N(H)—$R^4$ and $R^4$ is methyl, ethyl, propyl, isopropyl, cyclopropyl, cyclopentyl, or trifluoromethyl.
19. A compound of claim 1 wherein $R^3$—$C(O)$—N(H)—$R^4$ and $R^4$ is methyl, ethyl, propyl, isopropyl, cyclopropyl, cyclopentyl, or trifluoromethyl.
20. A compound of claim 1 wherein $R^3$ is —$C(O)$—N(H)—$R^4$ and $R^4$ is phenyl optionally substituted by halogen or lower alkyl.
21. A compound of claim 1 wherein $R^3$ is —$C(O)$—N(H)—$R^4$ and $R^4$ is phenyl optionally substituted once or twice by fluoro.
22. A compound of claim 1 wherein $R^3$ is pyridinyl.
23. A compound of claim 1 selected from the group consisting of:
[4-(4-Ethanesulfonyl-piperazine-1-carbonyl)-6-fluoro-3-methyl-naphthalen-2-yl]-acetic acid;
[4-(4-Ethanesulfonyl-piperazine-1-carbonyl)-6-fluoro-naphthalen-2-yl]-acetic acid;
[6-Fluoro-4-(4-methanesulfonyl-piperazine-1-carbonyl)-3-methyl-naphthalen-2-yl]-acetic acid;
{6-Fluoro-3-methyl-4-[4-(propane-2-sulfonyl)-piperazine-1-carbonyl]-naphthalen-2-yl}-acetic acid;
[6-Fluoro-3-methyl-4-(4-trifluoromethanesulfonyl-piperazine-1-carbonyl)-naphthalen-2-yl]-acetic acid;

[4-(4-Cyclopropanesulfonyl-piperazine-1-carbonyl)-6-fluoro-3-methyl-naphthalen-2-yl]-acetic acid;
{6-Fluoro-4-[4-(propane-1-sulfonyl)-piperazine-1-carbonyl]-naphthalen-2-yl}-acetic acid;
[4-(4-Cyclopentanesulfonyl-piperazine-1-carbonyl)-6-fluoro-3-methyl-naphthalen-2-yl]-acetic acid;
[4-(4-Benzenesulfonyl-piperazine-1-carbonyl)-6-fluoro-3-methyl-naphthalen-2-yl]-acetic acid;
{6-Fluoro-4-[4-(4-fluoro-benzenesulfonyl)-piperazine-1-carbonyl]-3-methyl-naphthalen-2-yl}-acetic acid;
[6-Fluoro-3-methyl-4-(4-phenylmethanesulfonyl-piperazine-1-carbonyl)-naphthalen-2-yl]-acetic acid;
{6-Fluoro-4-[4-(2-fluoro-benzenesulfonyl)-piperazine-1-carbonyl]-3-methyl-naphthalen-2-yl}-acetic acid;
{4-[4-(3,4-Difluoro-benzenesulfonyl)-piperazine-1-carbonyl]-6-fluoro-3-methyl-naphthalen-2-yl}-acetic acid;
{6-Fluoro-4-[4-(3-fluoro-benzenesulfonyl)-piperazine-1-carbonyl]-3-methyl-naphthalen-2-yl}-acetic acid;
{4-[4-(2,4-Difluoro-benzenesulfonyl)-piperazine-1-carbonyl]-6-fluoro-3-methyl-naphthalen-2-yl}-acetic acid;
[4-(4-Benzenesulfonyl-piperazine-1-carbonyl)-6-trifluoromethyl-naphthalen-2-yl]-acetic acid;
[4-(4-Benzenesulfonyl-piperazine-1-carbonyl)-6-trifluoromethoxy-naphthalen-2-yl]-acetic acid;
{6-Fluoro-4-[4-(4-fluoro-phenyl)-piperazine-1-carbonyl]-3-methyl-naphthalen-2-yl}-acetic acid;
[6-Fluoro-3-methyl-4-(4-pyridin-2-yl-piperazine-1-carbonyl)-naphthalen-2-yl]-acetic acid;
{6-Fluoro-4-[4-(2-fluoro-phenyl)-piperazine-1-carbonyl]-3-methyl-naphthalen-2-yl}-acetic acid;
[6-Fluoro-3-methyl-4-(4-phenyl-piperazine-1-carbonyl)-naphthalen-2-yl]-acetic acid;
[6-Fluoro-3-methyl-4-(4-pyrimidin-2-yl-piperazine-1-carbonyl)-naphthalen-2-yl]-acetic acid;
[6-Fluoro-3-methyl-4-(4-m-tolyl-piperazine-1-carbonyl)-naphthalen-2-yl]-acetic acid;
{6-Fluoro-3-methyl-4-[4-(3-trifluoromethyl-phenyl)-piperazine-1-carbonyl]-naphthalen-2-yl}-acetic acid;
{6-Fluoro-4-[4-(2-methoxy-phenyl)-piperazine-1-carbonyl]-3-methyl-naphthalen-2-yl}-acetic acid;
{6-Fluoro-4-[4-(3-methoxy-phenyl)-piperazine-1-carbonyl]-3-methyl-naphthalen-2-yl}-acetic acid;
{4-[4-(2-Ethyl-phenyl)-piperazine-1-carbonyl]-6-fluoro-3-methyl-naphthalen-2-yl}-acetic acid;
{4-[4-(3,5-Bis-trifluoromethyl-phenyl)-piperazine-1-carbonyl]-6-fluoro-3-methyl-naphthalen-2-yl}-acetic acid;
{6-Fluoro-4-[4-(4-methoxy-phenyl)-piperazine-1-carbonyl]-3-methyl-naphthalen-2-yl}-acetic acid;
{4-[4-(2,4-Difluoro-phenyl)-piperazine-1-carbonyl]-6-fluoro-3-methyl-naphthalen-2-yl}-acetic acid;
{4-[4-(3,5-Dimethoxy-phenyl)-piperazine-1-carbonyl]-6-fluoro-3-methyl-naphthalen-2-yl}-acetic acid;
{6-Fluoro-3-methyl-4-[4-(2-trifluoromethyl-phenyl)-piperazine-1-carbonyl]-naphthalen-2-yl}-acetic acid;
[6-Fluoro-3-methyl-4-(4-p-tolyl-piperazine-1-carbonyl)-naphthalen-2-yl]-acetic acid;
{4-[4-(3,5-Dichloro-phenyl)-piperazine-1-carbonyl]-6-fluoro-3-methyl-naphthalen-2-yl}-acetic acid;
{4-[4-(4-Chloro-phenyl)-piperazine-1-carbonyl]-6-fluoro-3-methyl-naphthalen-2-yl}-acetic acid;
{6-Fluoro-3-methyl-4-[4-(4-trifluoromethyl-phenyl)-piperazine-1-carbonyl]-naphthalen-2-yl}-acetic acid;
{4-[4-(2-Chloro-phenyl)-piperazine-1-carbonyl]-6-fluoro-3-methyl-naphthalen-2-yl}-acetic acid;
{4-[4-(3-Chloro-phenyl)-piperazine-1-carbonyl]-6-fluoro-3-methyl-naphthalen-2-yl}-acetic acid;
{6-Fluoro-3-methyl-4-[4-(5-trifluoromethyl-pyridin-2-yl)-piperazine-1-carbonyl]-naphthalen-2-yl}-acetic acid;
{4-[4-(3,5-Dichloro-pyridin-4-yl)-piperazine-1-carbonyl]-6-fluoro-3-methyl-naphthalen-2-yl}-acetic acid;
{4-[4-(4-Cyano-phenyl)-piperazine-1-carbonyl]-6-fluoro-3-methyl-naphthalen-2-yl}-acetic acid;
4-(3-Carboxymethyl-7-fluoro-naphthalen-1-yloxy)-piperidine-1-carboxylic acid tert-butyl ester;
[6-Fluoro-4-(1-methanesulfonyl-piperidin-4-yloxy)-naphthalen-2-yl]-acetic acid;
[4-(1-Ethanesulfonyl-piperidin-4-yloxy)-6-fluoro-naphthalen-2-yl]-acetic acid;
{6-Fluoro-4-[1-(propane-2-sulfonyl)-piperidin-4-yloxy]-naphthalen-2-yl}-acetic acid;
[4-(1-Cyclopropanesulfonyl-piperidin-4-yloxy)-6-fluoro-naphthalen-2-yl]-acetic acid;
[4-(1-Cyclopentanesulfonyl-piperidin-4-yloxy)-6-fluoro-naphthalen-2-yl]-acetic acid;
[4-(1-Benzenesulfonyl-piperidin-4-yloxy)-6-fluoro-naphthalen-2-yl]-acetic acid;
{6-Fluoro-4-[1-(3-fluoro-benzenesulfonyl)-piperidin-4-yloxy]-naphthalen-2-yl}-acetic acid;
{6-Fluoro-4-[1-(4-fluoro-benzenesulfonyl)-piperidin-4-yloxy]-naphthalen-2-yl}-acetic acid;
{6-Fluoro-4-[1-(pyridine-3-sulfonyl)-piperidin-4-yloxy]-naphthalen-2-yl}-acetic acid;
[6-Fluoro-4-(1-phenylmethanesulfonyl-piperidin-4-yloxy)-naphthalen-2-yl]-acetic acid;
[4-(1-Acetyl-piperidin-4-yloxy)-6-fluoro-naphthalen-2-yl]-acetic acid;
[6-Fluoro-4-(1-propionyl-piperidin-4-yloxy)-naphthalen-2-yl]-acetic acid;
[6-Fluoro-4-(1-isobutyryl-piperidin-4-yloxy)-naphthalen-2-yl]-acetic acid;
[4-(1-Cyclopropanecarbonyl-piperidin-4-yloxy)-6-fluoro-naphthalen-2-yl]-acetic acid;
[4-(1-Cyclopentanecarbonyl-piperidin-4-yloxy)-6-fluoro-naphthalen-2-yl]-acetic acid;
[4-(1-Benzoyl-piperidin-4-yloxy)-6-fluoro-naphthalen-2-yl]-acetic acid;
{6-Fluoro-4-[1-(2-fluoro-benzoyl)-piperidin-4-yloxy]-naphthalen-2-yl}-acetic acid;
{6-Fluoro-4-[1-(3-fluoro-benzoyl)-piperidin-4-yloxy]-naphthalen-2-yl}-acetic acid;
{6-Fluoro-4-[1-(4-fluoro-benzoyl)-piperidin-4-yloxy]-naphthalen-2-yl}-acetic acid;
[6-Fluoro-4-(1-phenylacetyl-piperidin-4-yloxy)-naphthalen-2-yl]-acetic acid;
[4-(1-Ethylcarbamoyl-piperidin-4-yloxy)-6-fluoro-naphthalen-2-yl]-acetic acid;
{6-Fluoro-4-[1-(2-fluoro-phenylcarbamoyl)-piperidin-4-yloxy]-naphthalen-2-yl}-acetic acid;
{6-Fluoro-4-[1-(3-fluoro-phenylcarbamoyl)-piperidin-4-yloxy]-naphthalen-2-yl}-acetic acid;
{6-Fluoro-4-[1-(4-fluoro-phenylcarbamoyl)-piperidin-4-yloxy]-naphthalen-2-yl}-acetic acid;
[6-Fluoro-4-(1-phenethylcarbamoyl-piperidin-4-yloxy)-naphthalen-2-yl]-acetic acid and any pharmaceutically acceptable salt or ester thereof.

24. A pharmaceutically acceptable salt of a compound of claim 20.

25. A pharmaceutically acceptable ester of a compound of claim 20.

26. A compound of claim 1 which is [4-(4-Benzenesulfonyl-piperazine-1-carbonyl)-6-fluoro-3-methyl-naphthalen-2-yl]-acetic acid.

27. A compound of claim 1 which is {4-[4-(4-Chloro-phenyl)-piperazine-1-carbonyl]-6-fluoro-3-methyl-naphthalen-2-yl}-acetic acid.

28. A compound of claim 1 which is [4-(1-Benzenesulfonyl-piperidin-4-yloxy)-6-fluoro-naphthalen-2-yl]-acetic acid.

29. A compound of claim 1 which is [6-Fluoro-4-(1-phenylmethanesulfonyl-piperidin-4-yloxy)-naphthalen-2-yl]-acetic acid.

30. A compound of claim 1 which is [6-Fluoro-4-(1-phenylacetyl-piperidin-4-yloxy)-naphthalen-2-yl]-acetic acid.

31. A compound of claim 1 which is {6-Fluoro-4-[1-(4-fluoro-phenylcarbamoyl)-piperidin-4-yloxy]-naphthalen-2-yl}-acetic acid.

32. A pharmaceutical composition comprising a therapeutically effective amount of a compound according to claim 1 and a pharmaceutically acceptable carrier.

33. A compound of formula Z:

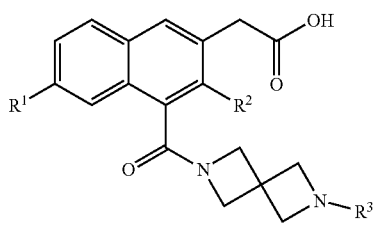

or a pharmaceutically acceptable salt or ester thereof, wherein:

$R^1$ is selected from the group consisting of:
  (a) hydrogen,
  (b) halogen,
  (c) lower alkyl optionally substituted by fluoro,
  (d) lower alkoxy optionally substituted by fluoro,
  (e) lower alkylsulfonyl, and
  (f) cyano;

$R^2$ is hydrogen or lower alkyl; and $R^3$ is $S(O)_2$—$R^4$ wherein $R^4$ is selected from the group consisting of:
  (a) phenyl or benzyl, wherein said phenyl or benzyl is optionally substituted by one or more substituents of: (1) halogen or (2) lower alkyl optionally substituted by fluoro; and
  (b) lower alkyl optionally substituted by fluoro.

34. A compound of claim 33 selected from the group consisting of:
  [4-(6-Benzenesulfonyl-2,6-diaza-spiro[3.3]heptane-2-carbonyl)-6-fluoro-3-methyl-naphthalen-2-yl]-acetic acid;
  [6-Fluoro-3-methyl-4-(6-phenylmethanesulfonyl-2,6-diaza-spiro[3.3]heptane-2-carbonyl)-naphthalen-2-yl]-acetic acid; and
  any pharmaceutically acceptable salt or ester thereof.

* * * * *

UNITED STATES PATENT AND TRADEMARK OFFICE
CERTIFICATE OF CORRECTION

PATENT NO. : 8,188,090 B2
APPLICATION NO. : 12/614497
DATED : May 29, 2012
INVENTOR(S) : Firooznia et al.

It is certified that error appears in the above-identified patent and that said Letters Patent is hereby corrected as shown below:

Title page, column 1, under (73) Assignee

Delete "Hoffman-La Roche Inc." and insert -- Hoffmann-La Roche Inc. --

Signed and Sealed this
Seventh Day of August, 2012

David J. Kappos
*Director of the United States Patent and Trademark Office*